(12) United States Patent
Jozefiak et al.

(10) Patent No.: US 7,119,120 B2
(45) Date of Patent: Oct. 10, 2006

(54) PHOSPHATE TRANSPORT INHIBITORS

(75) Inventors: Thomas H. Jozefiak, Watertown, MA (US); Cecilia M. Bastos, South Grafton, MA (US); Andrew T. Papoulis, Cunton, MA (US); Stephen Randall Holmes-Farley, Arlington, MA (US)

(73) Assignee: Genzyme Corporation, Cambridge, MA (US)

( * ) Notice: Subject to any disclaimer, the term of this patent is extended or adjusted under 35 U.S.C. 154(b) by 225 days.

(21) Appl. No.: 10/327,627

(22) Filed: Dec. 20, 2002

(65) Prior Publication Data

US 2004/0019113 A1    Jan. 29, 2004

Related U.S. Application Data

(60) Provisional application No. 60/371,649, filed on Apr. 10, 2002, provisional application No. 60/344,660, filed on Dec. 26, 2001.

(51) Int. Cl.
*A61K 31/18* (2006.01)
*A61K 31/16* (2006.01)
*A61K 37/18* (2006.01)

(52) U.S. Cl. .................. 514/602; 514/613; 514/617
(58) Field of Classification Search ............... 514/602, 514/613, 617
See application file for complete search history.

(56) References Cited

U.S. PATENT DOCUMENTS

| 5,496,545 | A |   | 3/1996 | Holmes-Farley et al. |
| 5,667,775 | A |   | 9/1997 | Holmes-Farley et al. |
| 5,716,993 | A | * | 2/1998 | Ozaki et al. ............... 514/619 |
| 6,083,495 | A |   | 7/2000 | Holmes-Farley et al. |
| 2003/0187033 | A1 | * | 10/2003 | Brendel et al. ............ 514/357 |

FOREIGN PATENT DOCUMENTS

| EP | 0 686 625 A | 12/1995 |
| EP | 0 947 500 A | 10/1999 |
| WO | WO 01 05398 A | 1/2001 |
| WO | WO 01 82924 A | 11/2001 |
| WO | WO 01 87294 A | 11/2001 |

OTHER PUBLICATIONS

Database Chemcats 'Online!; 2002:269117, Nov. 15, 2001, "Enamine Product Listing", XP002240447, abstract.
Database Chemcats 'Online!; 2002:269451, Nov. 15, 2001, "Enamine Product Listing", XP002240448, abstract.
Database Chemcats 'Online!; 2002:277993, Nov. 15, 2001, "Enamine Product Listing", XP002240449, abstract.
Crane, R.K., and Mandelstam, P., "The Active Transport of Sugars by Various Preparations of Hamster Intestine," *Biochim. Biophys. Acta*, 45: 460-476 (1960).
Feild, J.A., et al., "Cloning and Functional Characterization of a Sodium-Dependent Phosphate Transporter Expressed in Human Lung and Small Intestine," *Biochem. Biophys. Res. Commun.*, 258: 578-582 (1999).

* cited by examiner

*Primary Examiner*—Shengjun Wang
(74) *Attorney, Agent, or Firm*—Hamilton, Brook, Smith & Reynolds, P.C.

(57) ABSTRACT

Disclosed are compounds which have been identified as inhibitors of phosphate transport. Many of the compounds are represented by Structural Formula (I):

$$Ar_1-W-X-Y-Ar_2;$$

or a pharmaceutically acceptable salt thereof. $Ar_1$ and $Ar_2$ are independently a substituted or unsubstituted aryl group or an optionally substituted five membered or six membered non-aromatic heterocylic group fused to an optionally substituted monocylic aryl group. W and Y are independently a covalent bond or a C1–C3 substituted or unsubstituted alkylene group. X is a heteroatom-containing functional group, an aromatic heterocyclic group, substituted aromatic heterocyclic group, non-aromatic heterocyclic group, substituted non-aromatic heterocyclic group, an olefin group or a substituted olefin group. Also disclosed are methods of treating a subject with a disease associated with hyperphosphatemia, as well as a disease mediated by phosphate-transport function. The methods comprise the step of administering an effective amount of the one of the compounds described above.

10 Claims, No Drawings

PHOSPHATE TRANSPORT INHIBITORS

RELATED APPLICATIONS

This application claims the benefit of U.S. Provisional Application Nos. 60/344,660, filed on Dec. 26, 2001 and 60/371,649, filed on Apr. 10, 2002. The entire teachings of the above applications are incorporated herein by reference.

BACKGROUND OF THE INVENTION

People with inadequate renal function, hypoparathyroidism, or certain other medical conditions often have hyperphosphatemia, or elevated serum phosphate levels (over 6 mg/dL). Hyperphosphatemia, especially if present over extended periods of time, leads to severe abnormalities in calcium and phosphorus metabolism, often manifested by hyperparathyroidism, bone disease and calcification in joints, lungs, eyes and vasculature. For patients who exhibit renal insufficiency, elevation of serum phosphorus within the normal range has been associated with progression of renal failure and increased risk of cardiovascular events. The progression of kidney disease can be slowed by reducing phosphate retention. Thus, for renal failure patients who are hyperphosphatemic and for chronic kidney disease patients whose serum phosphate is within the normal range or is only slightly elevated, therapy to reduce phosphate retention is beneficial.

For patients who experience hyperphosphatemia, calcium salts have been widely used to bind intestinal phosphate and prevent its absorption. Different types of calcium salts including calcium carbonate, acetate, citrate, alginate, and ketoacid salts have been utilized for phosphate binding. The major problem with all of these therapeutics is the hypercalcemia which often results from absorption of high amounts of ingested calcium. Hypercalcemia causes serious side effects such as cardiac arrhythmias, renal failure, and skin and visceral calcification. Frequent monitoring of serum calcium levels is required during therapy with calcium-based phosphate binders. Other, calcium and aluminum-free phosphate binders have drawbacks including the amount and frequency of dosing required to be therapeutically active.

An alternative approach to the prevention of phosphate absorption from the intestine in patients with elevated phosphate serum levels is through inhibition of the intestinal transport system which mediates phosphate uptake in the intestine. It is understood that phosphate absorption in the upper intestine is mediated at least in part by a carrier-mediated mechanism which couples the absorption of phosphate to that of sodium in an energy-dependent fashion. Inhibition of intestinal phosphate transport will reduce serum phosphate levels. This would be particularly advantageous in patients susceptible to hyperphosphatemia as a result of renal insufficiency or in patients that have a disease that is treatable by inhibiting the uptake of phosphate from the intestines. Inhibition of phosphate absorption from the urine by the kidneys would also be advantageous for treating chronic renal failure. Furthermore, inhibition of phosphate transport may slow the progression of renal failure and reduce risk of cardiovascular events.

SUMMARY OF THE INVENTION

It has now been found that certain bis-aryl and other bis-cyclic compounds are effective inhibitors of phosphate transport proteins. For example, many bis-phenyl sulfonamides shown in Tables 1, 2 and 3, bis-phenyl ureas shown in Tables 4 and 5 and bis-aryl oxazolidines and bis-aryl pyrazoles shown in Tables 6 and 7 inhibit phosphate transport with an $IC_{50}$ below 50 µM or a percent inhibition greater than 80% at 100 µM in an in vitro assay. In addition, Table 14 in Example 91 shows that a number of bis-phenyl amides, guanidines and ureas, as well a number of benzaminocarbonyl-substituted bis-phenyl sulfonamides and phenyl cycloalkyl ureas, inhibit phosphate transport with an $IC_{50}$ of 40 µM or below in an in vitro assay. An ex vivo assay with the same compounds, the results of which are also presented in Table 14, further showed that they were effective in inhibiting phosphate uptake by the intestine. Based on this discovery, methods of treating a subject with chronic kidney disease, a disease associated with disorders of phosphate metabolism or a disease mediated by impaired phosphate-transport function are disclosed.

One embodiment of the present invention is a method of inhibiting phosphate transport in a subject in need of such treatment, which comprises the step of administering an effective amount of a bis-aryl compound represented by Structural Formula (I):

$$Ar_1\text{—}W\text{—}X\text{—}Y\text{—}Ar_2 \quad (I),$$

or a pharmaceutically acceptable salt thereof. $Ar_1$ and $Ar_2$ are independently substituted or unsubstituted aryl groups or an optionally substituted five membered or six membered non-aromatic heterocyclic group fused to an optionally substituted monocyclic aryl group (e.g., phenyl group). W and Y are independently a covalent bond or a C1–C3 substituted or unsubstituted alkylene group, (preferably a covalent bond or —CH$_2$—; more preferably a covalent bond). X is a heteroatom-containing functional group, an aromatic heterocyclic group, substituted aromatic heterocyclic group, non-aromatic heterocyclic group, substituted non-aromatic heterocyclic group, an olefin group or a substituted olefin group, examples of which are shown below.

In one aspect, the invention is a method of inhibiting phosphate transport in a subject in need of phosphate transport inhibition, where the method comprises the step of administering an effective amount of a compound represented by Structural Formula (II):

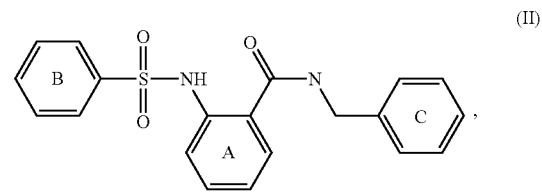

where Rings A, B and C are optionally substituted.

In another aspect, the present invention is a method of inhibiting phosphate transport in a subject in need of phosphate transport inhibition, where the method comprises the step of administering an effective amount of a compound represented by Structural Formula (III) or (IV):

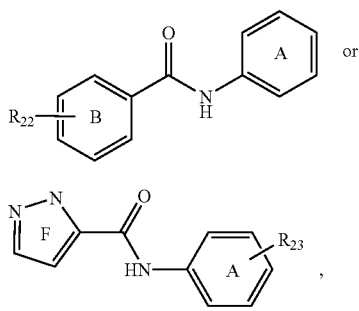

where $R_{22}$ and $R_{23}$ are a halogen, a lower alkyl group, a substituted lower alkyl group, an alkoxy group, a substituted alkoxy group or —$NO_2$; and Rings A, B and F are optionally substituted with one or more groups other than $R_{22}$ or $R_{23}$.

In a second embodiment, the present invention is a method of inhibiting phosphate transport in a subject in need of phosphate transport inhibition, where the method comprises the step of administering an effective amount of a compound represented by Structural Formula (V):

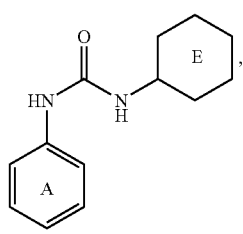

where Rings A and E are optionally substituted.

The invention is also directed to novel compounds represented by the following structural formula:

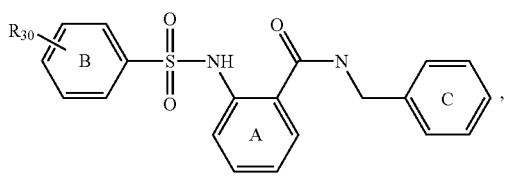

where $R_{30}$ is a substituted alkoxy group, preferably a haloalkyl or a haloalkoxy group such as trifluoromethyl or trifluoromethoxy; Rings A and C are optionally substituted; and Ring B optionally comprises one or more substituents other than $R_{30}$. Pharmaceutical compositions of the these compounds comprising a carrier or diluent and methods of use thereof for phosphate transport inhibition are also included in the present invention.

The phosphate transport inhibitors disclosed herein can be used for the manufacture of a medicament for inhibiting phosphate transport in a subject in need of such treatment, e.g., for treating or preventing disorders of phosphate metabolism or impaired phosphate transport function such as hyperphosphatemia, hyperparathyroidism, uremic bone disease, soft tissue calcification (e.g., cardiovascular calcification), progression of renal failure, cardiovascular events and osteoperosis. The invention also relates to the use of the compounds disclosed herein for inhibiting phosphate transport in a subject in need of such treatment, e.g., for treating or for preventing chronic renal failure or a disease associated with hyperphosphatemia.

Another embodiment of the present invention includes a pharmaceutical composition comprising one or more of the compounds disclosed herein, which have been identified as phosphate transport inhibitors and a pharmaceutically acceptable carrier, diluent or excipient. Similarly, the invention includes the use of one of the compounds disclosed herein in the treatment of one or more of the conditions or diseases disclosed herein. The invention also includes novel compounds disclosed herein.

Another embodiment of the present invention is the use of a compound represented by Structural Formulas (I)–(V) in combination with a pharmaceutically acceptable compound which binds phosphate (a "phosphate sequesterant"). The pharmaceutically acceptable phosphate binder can be a calcium, aluminum or lanthanum-containing phosphate binder or a phosphate-binding polymer such as those disclosed in U.S. Pat. Nos. 5,496,545, 5,667,775 and 6,083,495; the contents of which are incorporated herein by reference in their entirety. Preferably, the phosphate-binding polymer is a polyallylamine.

The compounds disclosed herein are effective inhibitors of phosphate transport and thus are useful for treatment of hyperphosphatemia, chronic renal failure, diseases associated with disorders of phosphate metabolism and impaired phosphate transport function. The beneficial aspects on chronic renal failure, disorders of phosphate metabolism or impaired phosphate transport function, e.g., hyperparathyroidism, uremic bone disease, renal bone disease, soft tissue calcification (e.g., cardiovascular calcification), cardiovascular events, and osteoporosis, could be mediated by either an effect on the intestinal transporters or on transporters in other tissues, such as those present in bone, kidney or vasculature.

DETAILED DESCRIPTION OF THE INVENTION

Disclosed herein are small molecule compounds which are inhibitors of phosphate transport. These small molecule compounds are preferably used to inhibit (i.e., reduce or prevent, in whole or in part) phosphate transport in the gastrointestinal tract and are therefore useful in treating conditions and diseases characterized by elevated phosphate levels, for example, hyperphosphatemia, renal failure and hypoparathyroidism. Many of the small molecule inhibitors are expected to be absorbed by the gastrointestinal tract and are therefore available systemically. As a consequence, they can inhibit phosphate transport in other organs such as the kidneys and can advantageously be used to treat chronic renal failure. Many of these phosphate transport inhibitors are bis-aryl compounds in which two aryl groups are separated by a heterocyclic ring, a heteroatom containing functional group or an olefin, represented by "X" in Structural Formula (I). Optionally, one or both aryl groups can be replaced with an optionally substituted monocyclic five or six membered non-aromatic heterocyclic group fused to an optionally substituted monocyclic aryl group. Other of the phosphate transport inhibitions have a central urea moiety, where one nitrogen is substituted with an aryl group and the other nitrogen atom is substituted with a cycloalkyl (e.g., cyclohexyl) group.

Optionally, one or both aryl or cycloalkyl groups are separated from X by an alkylene group, but preferably the aryl or cycloalkyl groups are connected directly to X.

Preferably X in Structural formula (I) is —S(O)$_2$—, —S(O)$_2$CR$_1$R$_2$—, —S(O)$_2$NR$_1$S(O)$_2$—, —C(O)NR$_1$C(O)—, —NR$_1$C(O)NR$_2$—, —NR$_1$C(NR$_3$)NR$_2$—, —(CH$_2$)$_n$—, —P(O)(OH)—, —C(O)—, —NR$_1$—, —N$^+$R$_1$R$_2$—, or a group represented by a structural formula selected from:

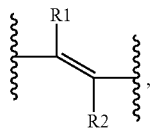
(VII)

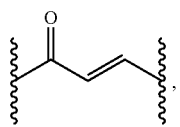
(VIII)

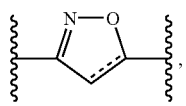
(IX)

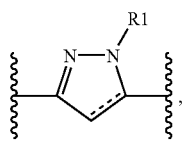
(X)

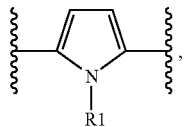
(XI)

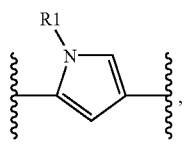
(XII)

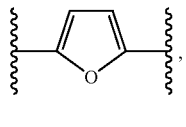
(XIII)

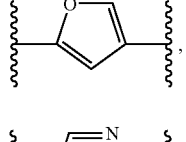
(XIV)

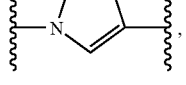
(XV)

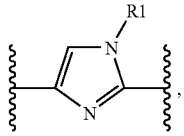
(XVI)

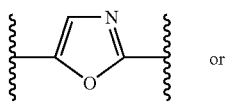
(XVII)

or

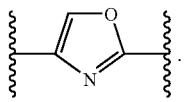
(XVIII)

$R_1$, $R_2$ and $R_3$ are independently a hydrogen, lower alkyl group, substituted lower alkyl group, heteroalkyl group, substituted heteroalkyl group, cycloalkyl group, substituted cycloalkyl group, aralkyl group, substituted aralkyl, heteroaralkyl group, or substituted heteroaralkyl.

Preferably, $Ar_1$ and $Ar_2$ are independently a phenyl group, a substituted phenyl group, a furyl group, a substituted furyl group, a thienyl group, a substituted thienyl group, a thiazolyl group, a substituted thiazolyl group, a triazinyl group, a substituted triazinyl group, a pyridyl group, a substituted pyridyl group, a pyrrolyl group, a substituted pyrrolyl group, an imidazolyl group, a substituted imidazolyl group, a pyrimidyl group, a substituted pyrimidyl group, a pyrazolyl group or a substituted pyrazolyl group. More preferably, $Ar_1$, and $Ar_2$ are independently a phenyl group, a substituted phenyl group, a furyl group or a substituted furyl group. Even more preferably, $Ar_1$ and $Ar_2$ are independently a phenyl group substituted with one or more substituents selected from the group consisting of: a hydrogen, a halogen, a lower alkyl group, a substituted lower alkyl group, a cycloalkyl group, a substituted cycloalkyl group, an alkoxy group, a substituted alkoxy group, an aryloxy group, a substituted aryloxy group, —C(O)NR$_4$R$_5$, —C(O)OR$_6$, —P(O)(OR$_6$)$_2$, —NR$_4$R$_5$, —N$_3$, —CN, —NO$_2$, —NR$_4$SO$_2$R$_5$, —N=N—$_4$, —SO$_3$, —S(O)$_2$R$_6$, —S(O)$_2$NR$_4$R$_5$, —SR$_4$, —C(O)R$_7$, —CR$_7$=NR$_4$ or —N=C=S.

$R_4$, $R_5$ and $R_6$ are independently a hydrogen, lower alkyl group, substituted lower alkyl group, heteroalkyl group, substituted heteroalkyl group, cycloalkyl group, substituted cycloalkyl group, aralkyl group, substituted aralkyl, heteroaralkyl group, or substituted heteroaralkyl group, or $R_4$ and $R_5$ taken together with the atom to which they are bonded, form an aromatic heterocyclic group, substituted aromatic heterocyclic group, non-aromatic heterocyclic group, or substituted non-aromatic heterocyclic group.

$R_7$ is a hydrogen, lower alkyl group, substituted lower alkyl group, heteroalkyl group, substituted heteroalkyl group, cycloalkyl group, substituted cycloalkyl group, an aryl group, a substituted aryl group, a heteroaryl group, a substituted heteroaryl group, substituted aralkyl, heteroaralkyl group, substituted heteroaralkyl, —OR$_6$ or —NR$_4$R$_5$.

In a preferred embodiment of the invention, phosphate transport inhibitors represented by Structural Formula (II) are represented by the structural formula:

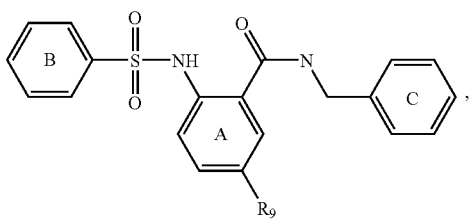

(XIX)

where $R_9$ is hydrogen or an electron-withdrawing group; and Ring A is optionally substituted with one or more substituents other than $R_9$. Preferably, $R_9$ is hydrogen or a halogen.

Even more preferably, a compound represented by Structural Formula (II) is represented by the following structural formula:

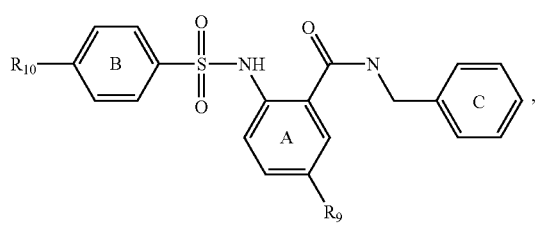

(XX)

where $R_{10}$ is hydrogen, a halogen, a substituted alkyl group, an alkoxy group, a substituted alkoxy group or —$NO_2$; Ring B is optionally substituted with one or more substituents other than $R_{10}$; Ring A is optionally substituted with one or more substituents other than $R_9$; and Ring C is optionally substituted. Preferably, $R_{10}$ is hydrogen, a halogen, an alkoxy group, a substituted alkoxy group or —$NO_2$. Even more preferably, $R_{10}$ is a halogen or a substituted alkoxy group, such as a halogen-substituted alkoxy group. An especially preferred substituted alkoxy group is a fluoro-substituted or perfluoro-substituted group such as a trifluoromethoxy group.

A yet more preferable compound represented by Structural Formula (II) is represented by the following structural formula:

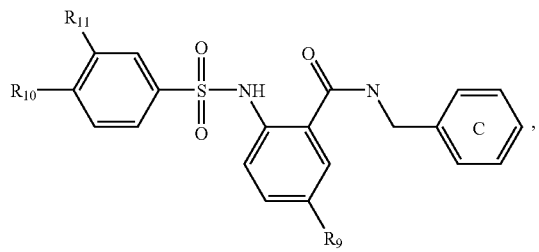

(XXI)

where $R_{11}$ is hydrogen, a halogen, an alkoxy group, a substituted alkoxy group or —$NO_2$; and Ring C is optionally substituted, as above. Typical substituents for Ring C include halogens, hydroxyl groups, substituted or unsubstituted alkyl and substituted or unsubstituted alkoxy groups. Preferably, Ring C is substituted with a halogen (e.g., bromine, fluorine), a hydroxyl group or a substituted or unsubstituted alkoxy group (e.g., methoxy, trifluoromethoxy). At least one Ring C substituent is typically ortho or para to the amide group, preferably ortho. Ring C typically has one or two substituents that are often ortho and para to the amide group.

Preferred compounds represented by Structural Formula (VI) are represented by the following structural formula:

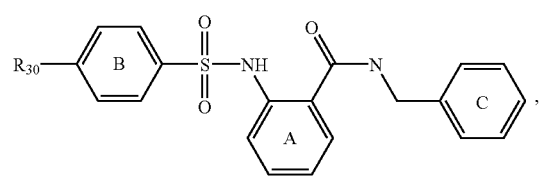

(XXII)

where Rings A and C are optionally substituted; and Ring B optionally comprises one or more substituents other than $R_{30}$. More preferably, the compound is represented by the structural formula:

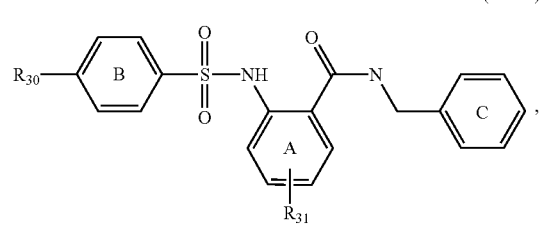

(XXIII)

where $R_{31}$ is a halogen; Ring C is optionally substituted; and Rings A and B optionally comprise one or more substituents other than $R_{30}$ and $R_{31}$. Even more preferably, the compound is represented by the following structural formula:

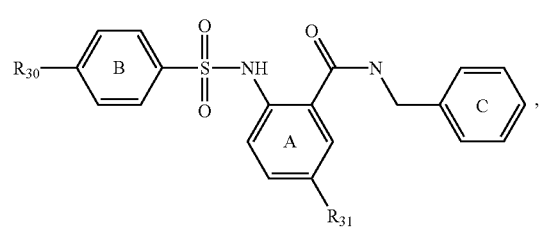

(XXIV)

where Ring C is optionally substituted; and Rings A and B optionally comprise one or more substituents other than $R_{30}$ and $R_{31}$. Rings A and B typically do not have substituents other than $R_{30}$ and $R_{31}$. More preferably, Ring A is monosubstituted with $R_{31}$ and Ring B is monosubstituted with $R_{30}$ or disubstituted with $R_{30}$ and a nitro group ortho to the sulfonamide moiety. Ring C is typically substituted with a halogen (e.g., bromine, fluorine), a hydroxyl group or a substituted or unsubstituted alkoxy group (e.g., methoxy, trifluoromethoxy). At least one Ring C substituent is typically ortho or para to the amide group, preferably ortho. Ring C typically has one or two substituents that are often ortho and para to the amide group.

When X in Structural Formula (I) is —NHC(O)NH—, $Ar_2$ is preferably represented by a structural formula selected from:

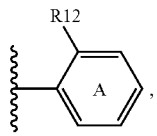
(XXV)

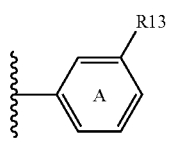
(XXVI)

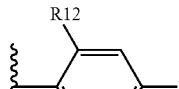
(XXVII)

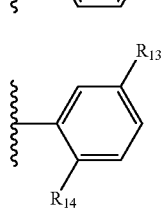
(XXVIII)

$R_{12}$ and $R_{13}$ are independently a hydrogen, a halogen, a lower alkyl group, a substituted lower alkyl group, a cycloalkyl group, a substituted cycloalkyl group, an alkoxy group, a substituted alkoxy group, —C(O)$NR_4R_5$, —C(O)$OR_6$, —P(O)(OR$_6$)$_2$, —NO$_2$, —SO$_3$, —S(O)$_2R_6$, —C(O)$R_7$ or —CR$_7$=NR$_4$. Preferably, $R_{12}$ is —C(O)NR$_4$R$_5$, —C(O)OR$_6$, —P(O)(OR$_6$)$_2$, —NO$_2$, SO$_3$, —S(O)$_2$R$_6$, —C(O)R$_7$ or —CR$_7$=NR$_4$. $R_{12}$ is more preferably —P(O)(OR$_6$)$_2$. $R_{13}$ is more preferably a hydrogen, a halogen, a lower alkyl group, a substituted lower alkyl group, an alkoxy group or a substituted alkoxy group or —NO$_2$.

$R_{14}$ is —H or an electron withdrawing group, preferably —H or a halogen. When $R_{13}$ is a halogen (e.g., chlorine) or a substituted alkyl group (e.g., a haloalkyl group such as trifluoromethyl), $R_{14}$ is advantageously hydrogen or a chloro group.

$R_4$—$R_7$ are as defined above.

Ring A is optionally substituted with one or more substituents other than $R_{12}$ and $R_{13}$.

When X is —NHC(O)NH— and $Ar_2$ is represented by Structural Formula (XXV), (XXVI), (XXVII) or (XXVIII), then $Ar_1$ is represented by a structural formula selected from:

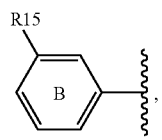
(XXIX)

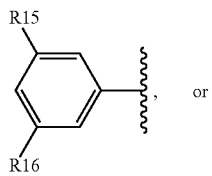
(XXX)

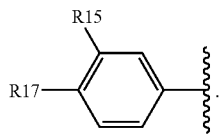
(XXXI)

$R_{15}$ is a hydrogen, a halogen, a lower alkyl group, a substituted lower alkyl group, an alkoxy group or a substituted alkoxy group or —NO$_2$.

$R_{16}$ and $R_{17}$ are independently hydrogen, a halogen, a lower alkyl group, a substituted lower alkyl group, an alkoxy group, a substituted alkoxy group or —NO$_2$. When $R_{15}$ is a haloalkyl or nitro group, preferably a fluoroalkyl or nitro group, then $R_{16}$ and $R_{17}$ are advantageously independently hydrogen, a halogen or a haloalkyl group, preferably hydrogen, a fluoro group or a trifluorometyl group.

Ring B is optionally substituted with one or more substituents other than $R_{15}$.

When X is represented by Structural Formula (IX) or (X), then $Ar_2$ is preferably represented by the following structural formula:

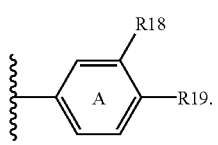
(XXXII)

$R_{18}$ and $R_{19}$ are independently, a hydrogen or a halogen.

When X is represented by Structural Formula (IX) or (X) and $Ar_2$ is represented by Structural Formula (XXXII), then $Ar_1$ is represented by the following structural formula:

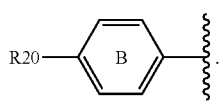
(XXXIII)

R20 is a hydrogen or OR$_{21}$; and $R_{21}$ is a hydrogen, an alkyl group, or an aryl group.

When X is represented by Structural Formula (VII), $R_1$ and $R_2$ are preferably —H or a lower alkyl group. More preferably, $R_1$ and $R_2$ are —H or a lower alkyl group and $Ar_1$ and $Ar_2$ are independently represented by a structural formula selected from:

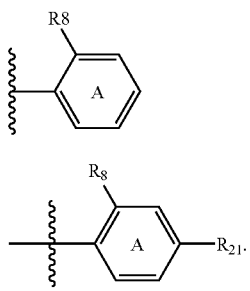

(XXXIV)

(XXXV)

R8 is a hydrogen or —SO$_3$.

R21 is a hydrogen, a hydroxy group, —NR$_4$R$_5$, —NR$_4$SO$_2$R$_5$, —N=N—R$_4$, or —N=C=S; and R$_4$ and R$_5$ are as described above.

When X is —S(O$_2$)—, Ar$_2$ is preferably an optionally substituted monocyclic heteroaryl ring fused to an optionally substituted phenyl ring, more preferably a nitrogen-containing heteroaryl ring fused to a phenyl ring, i.e., a bicyclic nitrogen-containing heteroaryl group. The bicyclic heteroaryl group can be substituted or unsubstituted. Examples of preferred bicyclic nitrogen-containing heteroaryl groups include indolyl, benzpyrazolyl, benzimidazolyl and benztriazolyl. When X is —S(O$_2$)— and Ar$_2$ is a nitrogen-containing heteroaryl ring fused to a phenyl ring, then Ar$_1$ is preferably a substituted or unsubstituted phenyl group.

In one preferred embodiment, Ar$_1$ is a substituted or unsubstituted aryl group (preferably phenyl) and Ar$_2$ is an optionally substituted five member or six membered non-aromatic heterocyclic group fused to an optionally substituted monocyclic aryl group (preferably phenyl), i.e., a bicyclic ring system. When Ar$_2$ has this value, X is preferably —S(O$_2$)— or can take on a new value of —C(O)NH—. Preferred non-aromatic heterocyclic groups are nitrogen containing. Examples of bicyclic ring systems for Ar$_2$ include the following:

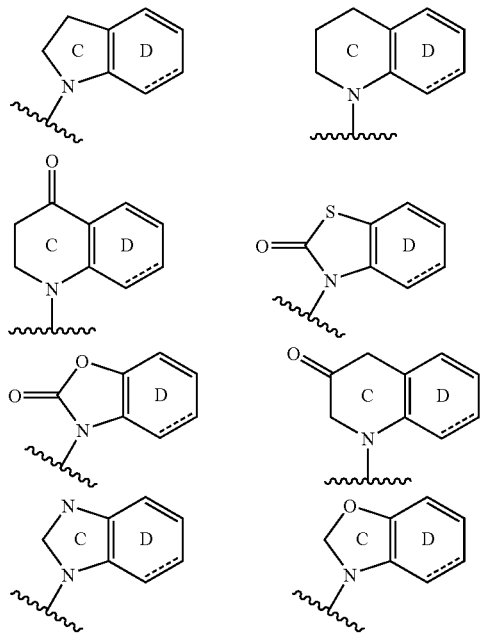

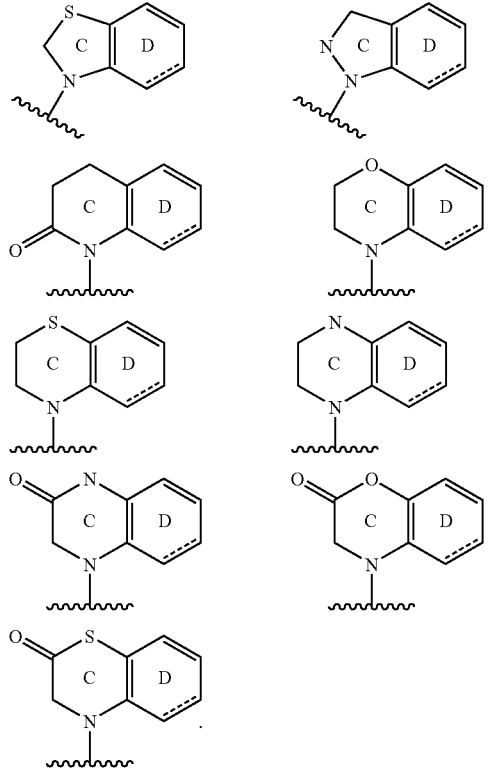

Rings C and D are independently substituted or unsubstituted.

In another preferred embodiment, X is —NR$_1$C(NR$_3$)NR$_2$—. R$_1$, R$_2$ and R$_3$ are as defined above, but are preferably each hydrogen. In this embodiment, Ar$_1$ is typically represented by structural formulas:

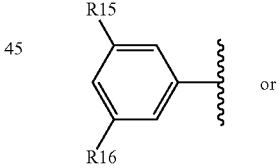

(XXXVI)

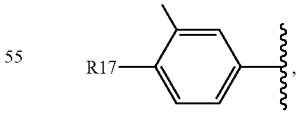

(XXXVII)

where R$_{15}$, R$_{16}$ and R$_{17}$ are as defined above. Preferably, R$_{15}$, R$_{16}$ and R$_{17}$ are each independently a halogen or a substituted alkyl group, such as bromine, chlorine and a trifluoromethyl group.

When X is —NR$_1$C(NR$_3$)NR$_2$— and Ar$_1$ is represented by Structural Formula (XXXVI) or (XXXVII), Ar$_2$ is typically represented by structural formula:

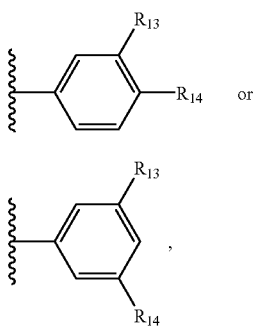

where $R_{13}$ and $R_{14}$ are as defined above. Preferably, $R_{13}$ and $R_{14}$ are each independently a halogen or a substituted alkyl group. In this embodiment, $R_{13}$, $R_{14}$, $R_{15}$ and $R_{16}$ are advantageously each a halogen or a haloalkyl group. Typical examples of these groups include chlorine, bromine and trifluoromethyl groups.

In another embodiment, the compound is represented by Structural Formula (III) or (IV). In one example, the compound is represented by one of the following structural formulas:

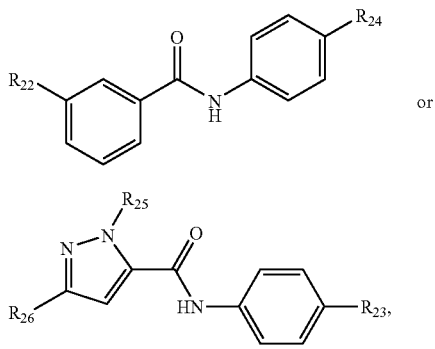

where $R_{24}$, $R_{25}$ and $R_{26}$ are each independently hydrogen or a substituted or unsubstituted alkyl group. Typically, the alkyl groups are substituted alkyl groups, such as, in order of increasing specificity, haloalkyl groups, fluoroalkyl groups, perfluoroalkyl groups and trifluoromethyl groups.

In another embodiment of the invention, the method of inhibiting phosphate transport in a subject comprises the step of administering a compound represented by the structural formula:

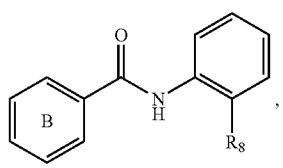

where $R_8$ is $-P(O)(OR_6)_2$, $R_6$ is hydrogen or a lower alkyl group, and Ring B is optionally substituted as described above. In a preferred embodiment, the compound is represented by the structural formula:

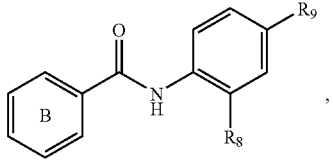

where $R_9$ is hydrogen or an electron-withdrawing group, such as a halogen.

In yet another embodiment, the phosphate transport inhibitor compound is represented by Structural Formula (V). Ring A can be substituted with one or more electron-withdrawing groups, such as a haloalkyl (e.g., trifluoromethyl) group. Ring E is optionally substituted with one or more halogens or substituted or unsubstituted alkyl or alkoxy groups. One example of a compound falling within Structural Formula (V) is represented by the structural formula:

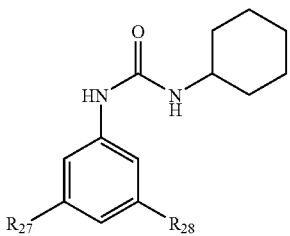

where $R_{27}$ and $R_{28}$ are independently hydrogen or a substituted alkyl group. Preferred substituted alkyl groups include haloalkyl groups such as fluoroalkyl groups (e.g., trifluoromethyl).

Also included in the present invention are physiologically acceptable salts of the compounds described herein. Compounds disclosed herein which possess a sufficiently acidic, a sufficiently basic functional group or both, can react with any of a number of organic or inorganic bases, and inorganic and organic acids to form a salt.

Salts of compounds containing an amine or other basic group can be obtained, for example, by reacting those compounds with a suitable organic or inorganic acid. Salts of compounds containing a carboxylic acid or other acidic functional group can be prepared by reacting them with a suitable base.

Base addition salts include those derived from inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, and the like.

Acids commonly employed to form acid addition salts from compounds with basic groups are inorganic acids such as hydrochloric acid, hydrobromic acid, hydroiodic acid, sulfuric acid, phosphoric acid, and the like, and organic acids such as p-toluenesulfonic acid, methanesulfonic acid, oxalic acid, p-bromophenyl-sulfonic acid, carbonic acid, succinic acid, citric acid, benzoic acid, acetic acid, and the like. Examples of such salts include the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, gamma-hydroxybutyrate, glycolate, tartrate, methanesulfonate, propanesulfonate, naphthalene-1-sulfonate, naphthalene-2-sulfonate, mandelate, and the like.

A "lower alkyl group" as used herein, is a saturated straight chained or branched hydrocarbon. Typically, lower alkyl groups have from one to eight carbons. Preferably, lower alkyl groups have from one to six carbon atoms.

A "heteroalkyl group" as used herein, is a lower alkyl group in which at least one methylene group has been replaced with a heteroatom, such as nitrogen, oxygen, or sulfur.

A "cycloalkyl group" as used herein, is a non-aromatic carbocyclic ring system that has 3 to 10 atoms. A cycloalkyl group can optionally be fused to a carbocyclic non-aromatic ring, carbocyclic aromatic ring, a heterocyclic aromatic ring, non-aromatic heterocyclic ring, or another non-aromatic carbocyclic ring. Examples of a cycloalkyl group include cyclopropyl, cyclobutyl, cyclopentyl, cyclohexyl, cycloheptyl, cyclooctyl, cyclononyl, cyclodecyl, 1,2,3,4-tetrahydronaphthyl, and 1,2,3-tetrahydroindanyl.

A "heterocycloalkyl group" or a "non-aromatic heterocyclic group", as used herein, is a non-aromatic ring system that has 3 to 10 atoms and includes at least one heteroatom, such as nitrogen, oxygen, or sulfur. A heterocycloalkyl group is optionally fused to a carbocyclic non-aromatic ring, carbocyclic aromatic ring, a heterocyclic aromatic ring, or another non-aromatic heterocyclic ring. Examples of heterocycloalkyl groups include piperazinyl, piperidinyl, homopiperazinyl, quinuclidinyl, azetidinyl, morpholinyl, thiomorpholinyl, thiazolidinyl, 1,2,3,4-tetrahydroquinolinyl, 1,2,3-tetrahydroindolyl, indolyl, furanyl or imidazolyl.

The term "aryl group", as used herein, includes both carbocyclic and heterocyclic aromatic ring systems. An aryl group is optionally fused to a carbocyclic non-aromatic ring, a heterocyclic non-aromatic ring, a heterocyclic aromatic ring or another carbocyclic aromatic ring. A carbocyclic aromatic system consists only of carbon ring atoms, preferably up to ten.

Examples of carbocyclic aryl groups include phenyl, naphthyl and 5,6,7,8-tetrahydronaphthyl or 5,6,7-tetrahydroindanyl.

A "heteroaryl group" or an "aromatic heterocyclic group", as used herein, is an aryl group that has 3 to 10 ring atoms including one or more ring heteroatoms such as nitrogen, oxygen and sulfur. A heteroaryl group can be monocyclic. Alternatively, a monocyclic heteroaryl group is fused to one or more other monocyclic heteroaryl groups or monocyclic carbocyclic aryl groups. Preferably a heteroaryl group has 1 to 3 heteroatoms. A heteroaryl group is optionally fused to a carbocyclic aromatic ring, carbocyclic non-aromatic ring or another heteroaryl ring. Examples of a heteroaryl group include thienyl, pyridyl, pyrazolyl, isoxazolyl, thiadiazolyl, oxadiazolyl, indazolyl, furyl, pyrrolyl, imidazolyl, pyrazolyl, triazolyl, pyrimidinyl, pyridazinyl, pyrazinyl, thiazolyl, isoxazolyl, isothiazolyl, tetrazolyl, oxazolyl, oxadiazolyl, quinolinyl, carbazolyl, benzocarbazolyl, benzotriazolyl, benzimidazole, benzothiophene, benzofuran or indolyl.

An "aralkyl group", as used herein, is an aryl group that is linked to a compound by an alkyl group having from one to about six carbon atoms.

A "heteroaralkyl group", as used herein, is a heteroaryl group that is linked to a compound by an alkyl group having from one to about six carbon atoms.

A "halogen" as used herein, includes fluorine, chlorine, bromine and iodine atoms.

An "olefin group" as used herein, is a group containing a double bond. The double bond may be an E- or Z-isomer. Preferably the double bond is an E-isomer.

An "alkylene group", as used herein, is represented by $-(CH_2)_n-$. n is an integer from 1–10, preferably 1–4.

A "heteroatom containing functional group", as used herein, is a functional group containing one or more heteroatoms such as nitrogen, oxygen or sulfur. Examples include $-NR_1-$, $-NR_1R_2-$, $-O-$, $-S-$, $-C(O)-$, $-C(O)O-$, $-OC(O)-$, $-P(O)(OH)-$, $-CR_1=N-$, $-N=CR_1-$, $-S(O)_2NR_1-$, $-NR_1S(O)_2-$, $-S(O)_2-$, $-S(O)_2CR_1R_2-$, $-CR_1R_2S(O)_2-$, $-S(O)_2NR_1S(O)_2-$, $-NR_1C(O)-$, $-C(O)NR_1-$, $-C(O)NR_1C(O)-$, $-NR_1C(O)NR_2-$, $-NR_1C(S)NR_2-$, or $-NR_1C(NR_3)NR_2-$. $R_1$ and $R_2$ are as defined above.

Two rings are "fused" when they share two adjacent ring atoms.

Suitable substituents on a substituted lower-alkyl group, substituted heteroalkyl group, substituted cycloalkyl group, substituted heterocycloalkyl group, substituted aryl group, substituted heteroaryl group, substituted aralkyl group, substituted heteroaralkyl group, substituted alkoxy group or substituted aryloxy group include for example, a hydrogen, a halogen, an electron withdrawing group, a hydroxy group, an alkoxy group, a lower alkyl group, a cycloalkyl group, a heterocycloalkyl group, an aryl group, a heteroaryl group, an aryloxy group, an aralkyl group, a heteroaralkyl group, $-C(O)NR_4R_5$, $-C(O)OR_6$, $-P(O)(OR_6)_2$, $-NR_4R_5$, $-NCR_7(PO_3)_2$, $-NO_2$, $-SO_3$, $-S(O)_2R_6$, $-C(O)R_7$, $-SR_4$, $-CR_7=NR_4$, $-NR_4SO_2R_5$, $-N=N-R_4$, $-CN$, $-N_3$ or $-N=C=S$. $R_4$, $R_5$, $R_6$ and $R_7$ are as defined above. A substituted lower-alkyl group, substituted heteroalkyl group, substituted cycloalkyl group, substituted heterocycloalkyl group, substituted aryl group, substituted heteroaryl group, substituted aralkyl group, substituted heteroaralkyl group, substituted alkoxy group or substituted aryloxy group can have more than one substituent.

The term "electron withdrawing group", as it is used herein, has the meaning commonly afforded the term in the art. Specifically, an electron withdrawing group is a functional group which withdraws electron density from the moiety to which it is attached. For example, an electron withdrawing group results in a phenyl ring that has less electron density when the group is present than when it is absent. Electron withdrawing groups may withdraw electron density by inductive or resonance effects. Electron withdrawing groups have a Hammet sigma value greater than zero (see, for example, C. Hansch, A. Leo and D. Hoeckman, "Exploring QSAR Hydrophobic, Electronic and Steric Constants", American Chemical Society (1995), pages 217–32). Examples of electron withdrawing groups include halogens, alkylimines, alkylsulfonyl, carboxamido, carboxylic alkyl esters, $-CH=NH$, $-CN$, and $-NO_2$.

In the structural formulas depicted herein, the single or double bond by which a chemical group or moiety is connected to the remainder of the molecule or compound is indicated by the following symbol:

In the structural formulas depicted herein, a bond which is optionally a single or double bond is indicated by the following symbol:

It will be understood that the structures depicted herein will be read form left to right. For example, when X is —S(O)$_2$NH—, sulfur is the point of attachment to W and nitrogen is the point of attachment to Y.

A "subject" is preferably a human, but can also be an animal in need of treatment with a phosphate transport inhibitor, e.g., companion animals (e.g., dogs, cats, and the like), farm animals (e.g., cows, pigs, horses and the like) and laboratory animals (e.g., rats, mice, guinea pigs and the like).

Subjects "in need of treatment" with a compound of the present invention, or subjects "in need of phosphate transport inhibition" include subjects with diseases and/or conditions that can be treated with phosphate transport inhibitors to achieve a beneficial therapeutic and/or prophylactic result. A beneficial outcome includes a decrease in the severity of symptoms or delay in the onset of symptoms, increased longevity and/or more rapid or more complete resolution of the disease or condition. For example, a subject in need of treatment typically has elevated serum phosphate levels, hyperphosphatemia, resulting from, for example, impaired kidney function or hypoparathyroidism. Lower serum phosphate levels can be achieved, for example, by inhibiting phosphate transport in the intestines. A subject "in need of treatment" also includes a subject with chronic renal failure who may have serum phosphate levels within the normal range. Inhibition of phosphate transport in the intestine or kidneys can slow rate of renal deterioration in these subjects, and decrease the risk of cardiovascular events. Other examples of subjects in need of phosphate transport inhibitors include patients with a disease associated with disorders of phosphate metabolism or a disease medicated by impaired phosphate transport function. Examples of diseases and/or disorders of this type include soft tissue calcification, such as cardiovascular calcification, hyperparathyroidism, uremic bone disease, renal bone disease and osteoporosis.

An "effective amount" of a compound disclosed herein, is a quantity that results in a beneficial clinical outcome of the condition being treated with the compound compared with the absence of treatment. The amount of phosphate transport inhibiting compound administered will depend on the degree, severity, and type of the disease or condition, the amount of therapy desired, and the release characteristics of the pharmaceutical formulation. It will also depend on the subject's health, size, weight, age, sex and tolerance to drugs. Typically, the compound is administered for a sufficient period of time to achieve the desired therapeutic effect. Typically between about 5 g per day and about 0.001 g per day of compound (preferably between about 1 g per day and about 0.001 g per day) is administered to the subject in need of treatment.

The compound can be administered by any suitable route. The compound is preferably administrated orally (e.g., dietary) in capsules, suspensions, tablets, pills, dragees, liquids, gels, syrups, slurries, and the like. Methods for encapsulating compositions (such as in a coating of hard gelatin or cyclodextran) are known in the art (Baker, et al., "Controlled Release of Biological Active Agents", John Wiley and Sons, 1986). The compounds can be administered to the subject in conjunction with an acceptable pharmaceutical carrier as part of a pharmaceutical composition. The formulation of the pharmaceutical composition will vary according to the route of administration selected. Suitable pharmaceutical carriers may contain inert ingredients which do not interact with the compound. The carriers should be biocompatible, i.e., non-toxic, non-inflammatory, non-immunogenic and devoid of other undesired reactions at the administration site. Examples of pharmaceutically acceptable carriers include, for example, saline, commercially available inert gels, or liquids supplemented with albumin, methyl cellulose or a collagen matrix. Standard pharmaceutical formulation techniques can be employed, such as those described in Remington's Pharmaceutical Sciences, Mack Publishing Company, Easton, Pa.

Pharmaceutical preparations for oral use can be obtained by combining a compound of the present invention with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents can be added, such as the cross-linked polyvinyl pyrrolidone, agar, or alginic acid or a salt thereof such as sodium alginate.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include push-fit capsules made of a suitable material, such as gelatin, as well as soft, sealed capsules made of a suitable material, for example, gelatin, and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

It will be understood that, certain compounds of the invention may be obtained as different stereoisomers (e.g., diastereomers and enantiomers) and that the invention includes all isomeric forms and racemic mixtures of the disclosed compounds and a method of treating a subject with both pure isomers and mixtures thereof, including racemic mixtures. Stereoisomers can be separated and isolated using any suitable method, such as chromatography.

The activity of compounds of the present invention can be assessed using suitable assays, such as the $^{33}PO_4$ Uptake In Rabbit Intestinal BBMV High Throughput Screening (HTS) assay, as described in the Example 66, and $^{33}PO_4$ uptake in isolated rabbit intestinal rings, as described in Example 91. Compounds of the present invention can also be identified by virtue of their ability to inhibit the absorption of phosphate in vivo, for example, in the gastrointestinal tract of a laboratory animal.

The compounds disclosed herein can be prepared accordingly as shown in Examples 1–65 and 67–90. The schemes are described in greater detail below.

In certain instances it may be advantageous to co-administer one or more additional pharmacologically active agents along with a phosphate transport inhibitor. Examples include pharmaceutically active calcium, aluminum or lanthanum-containing phosphate binders or pharmaceutically active phosphate-binding polymers such as those disclosed in U.S. Pat. Nos. 5,496,545, 5,667,775 and 6,083,495; the contents of which are incorporated herein by reference in their entirety. Preferably the pharmacologically active agent is a polyallylamine phosphate-binding polymer. More preferably, the pharmacologically active agent is an epichlorohydrin-cross-linked poly(allylamine hydrochloride) resin, also referred to as sevelamer hydrochloride or sevelamer, and marketed as RENAGEL® (GelTex Pharmaceuticals, Inc., Waltham, Me.).

Another embodiment of the present invention is one of the compounds disclosed herein. Yet another embodiment is a pharmaceutical composition comprising a pharmaceutically acceptable carrier or diluent and one of the compounds disclosed herein.

The invention is illustrated by the following examples which are not intended to be limiting in any way.

EXEMPLICATION

EXAMPLE 1

Methyl 5-bromo-2-[(4'-trifluoromethoxyphenyl) sulfonyl]amino benzoate

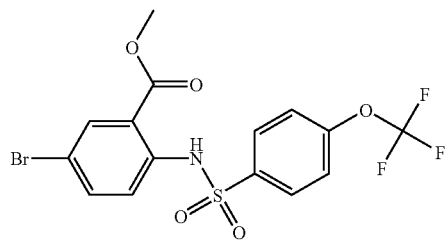

Methyl 2-amino-5-bromo benzoate (2.78 g, 0.012 mol) was dissolved in pyridine (3 mL). The mixture was cooled in an ice bath below 5° C. and 4-trifluoromethoxy benzene sulfonyl chloride (3.5 g, 0.013 mol, 1.1 equivalents) was added slowly to the mixture. The mixture was warmed to room temperature, and stirred for 1 hour. The solvent was removed and the resulting solid was suspended in HCl (1M, 40 mL) for 30 minutes. The mixture was filtered, the solid suspended in hexane (40 mL) and stirred for 30 minutes. The mixture was filtered and the solid was washed with hexane (2×20 mL). Solid was dried in a vacuum oven at 40° C. Recovery=4.63 g (85% yield).

EXAMPLE 2

5-Bromo-2-[(4'-trifluoromethoxyphenyl)sulfonyl] amino benzoic acid

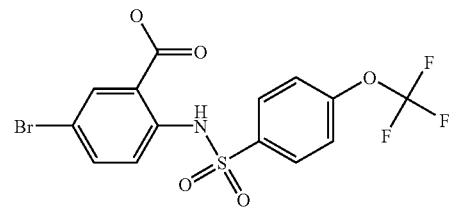

Methyl 5-bromo-2-[(4'-trifluoromethoxyphenyl)sulfonyl] amino benzoate (0.854 g, 0.019 mmol) was dissolved in a mixture of tetrahydrofuran (20 mL)/water (10 mL). A solution of sodium hydroxide (50%, 5 mL) was added and the mixture was heated to reflux for 2–3 hours. The tetrahydrofuran was removed by rotary evaporation and the mixture was acidified with HCl (2 M). The mixture was extracted with ethyl acetate (20 mL). The organic solvent was removed to dryness and then dissolved in ethyl acetate (3×15 mL), and solvent removed. The oil was triturated in hexane (20 mL) until a solid formed. The mixture was filtered and the solid was dried in a vacuum oven at 40° C. Recovery=0.691 g (83% yield). M/Z of (M–H)$^-$=432, $^1$H NMR (DMSO) δ=7.42–7.48 (1H), 7.55–7.6 (2H), 7.74–7.8 (1H), 7.92–8.0 (3H), 11.2 (br, 1H).

EXAMPLE 3

5-Bromo-2-[(4'-trifluoromethoxyphenyl)sulfonyl] amino benzoyl chloride

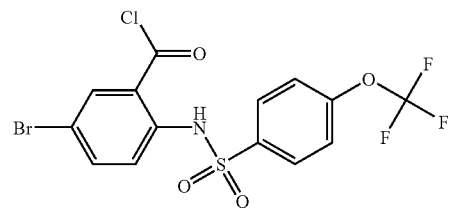

5-bromo-2-[(4'-trifluoromethoxyphenyl)sulfonyl]amino benzoic acid (3.27 g, 7.4 mmol) was suspended in thionyl chloride (30 mL) and the mixture was heated to reflux for 4 hours. The solvent was removed to dryness and the residue was dissolved in anhydrous ethyl acetate (2×20 mL), and solvent removed. The solid was dried at 40° C. in vacuum oven overnight.

EXAMPLE 4

5-Bromo-2-[(4'-trifluoromethoxyphenyl)sulfonyl]amino-N-(2''-methoxybenzyl)benzamide

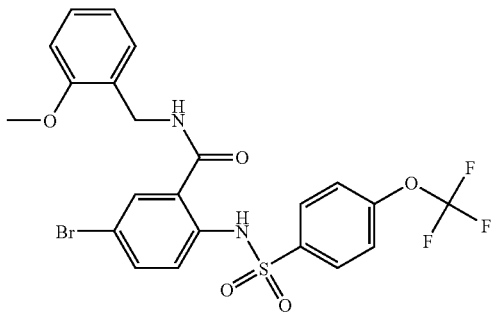

5-Bromo-2-[(4'-trifluoromethoxyphenyl)sulfonyl]amino benzoyl chloride (5.124 g, 11.6 mmol) was dissolved in tetrahydrofuran (100 mL) and the mixture was cooled in an ice bath below 5° C. 2-Methoxybenzyl amine (1.8 mL, 13.8 mmol, 1.2 equivalents) and triethyl amine (1.9 mL, 13.6 mmol, 1.2 equivalents) were added to the mixture keeping the temperature below 10° C. The mixture was warmed to room temperature and the solvent was removed to dryness. The residue was partitioned between HCl (1M, 50 mL) and ethyl acetate (100 mL). The organic solvent was collected and concentrated to dryness. The resulting solid was dissolved in ethyl acetate (2×25 mL) and the solvent removed. The mixture was purified by column chromatography using 20% ethyl acetate in hexane. The solid was suspended in a mixture of 5% ethyl acetate in hexane (90 mL). The mixture was centrifuged and the solid dried at 40° C. overnight in vacuum oven. Recovery=4.85 g (75% yield). M/Z of [M–H]$^-$=557, $^1$H NMR (CDCl$_3$) δ=3.85 (s, 3H), 4.5 (sd, 2H), 6.5–6.6 (1H), 6.9–7.05 (4H), 7.3–7.4 (2H), 7.45 (1H), 7.5 (1H), 7.6 (1H), 7.8 (2H), 10.8 (br, 1H).

EXAMPLE 5

5-Bromo-2-[(4'-trifluoromethoxyphenyl)sulfonyl]amino-N-(4''-fluorobenzyl)benzamide

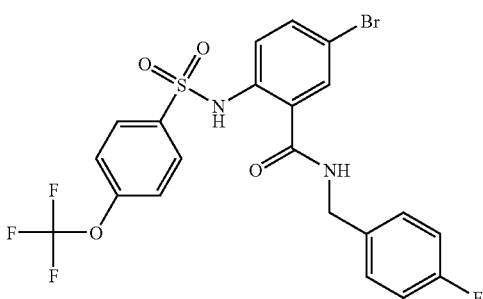

This compound was prepared using the procedure described in Example 4, using 4-fluorobenzyl amine instead of 2-methoxy benzyl amine: M/Z of [M–H]$^-$=545. $^1$H NMR (DMSO) δ=4.4 (sd, 2H), 7.15–7.23 (2H), 7.3–7.4 (2H), 7.4–7.5 (3H), 7.65–7.7 (1H), 7.8–7.9 (2H), 7.9–8.0 (1H), 9.4 (br, 1H), 11.5 (br, 1H).

EXAMPLE 6

5-Bromo-2-[(4'-chlorophenyl)sulfonyl]amino-N-(4''-fluorobenzyl)benzamide

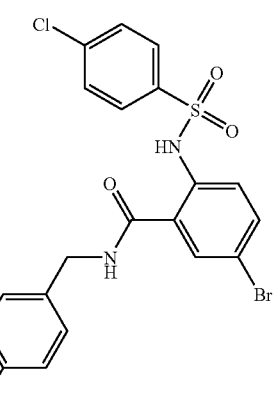

This compound was prepared using the procedure described in Example 4, using 4-fluoro benzyl amine instead of 2-methoxy benzyl amine and 5-bromo-2-[(4'-chlorophenyl)sulfonyl]amino benzoyl chloride instead of 5-bromo-2-[(4'-trifluoromethoxyphenyl)sulfonyl]amino benzoyl chloride: M/Z of [M–H]$^-$=495. $^1$H NMR (DMSO) δ=4.4 (sd, 2H), 7.15–7.25 (2H), 7.3–7.4 (2H), 7.45–7.5 (1H), 7.55–7.6 (2H), 7.65–7.75 (3H), 7.9–7.95 (2H), 9.4 (1H), 11.4 (br, 1H).

EXAMPLE 7

5-Bromo-2-[(4'-chlorophenyl)sulfonyl]amino-N-(3''-bromophenyl)benzamide

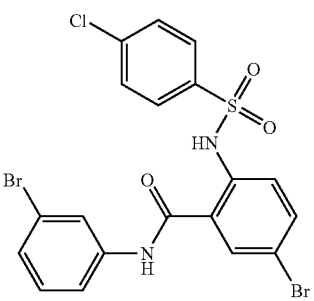

This compound was prepared using the procedure described in Example 4, using 3-bromo aniline instead of 2-methoxy benzyl amine and 5-bromo-2-[(4'-chlorophenyl)sulfonyl]amino benzoyl chloride instead of 5-bromo-2-[(4'-trifluoromethoxyphenyl)sulfonyl]amino benzoyl chloride. M/Z of [M–H]$^-$=541. $^1$H NMR (DMSO) δ=7.2–7.4 (1H), 7.27–7.32 (2H), 7.45–7.52 (2H), 7.52–7.6 (1H), 7.62–7.7 (2H), 7.8–7.84 (1H), 7.88–7.9 (1H), 10.2 (1H), 10.4 (1H).

EXAMPLE 8

5-Bromo-2-[(4'-chlorophenyl)sulfonyl]amino-N-(2''-methoxybenzyl)benzamide

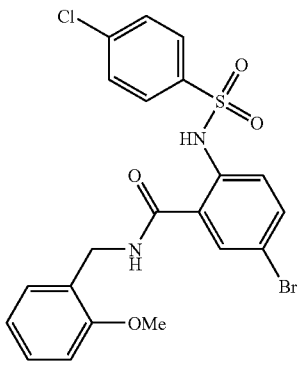

This compound was prepared using the procedure described in Example 4, using 5-bromo-2-[(4'-chlorophenyl)sulfonyl]amino benzoyl chloride instead of 5-bromo-2-[(4'-trifluoromethoxyphenyl)sulfonyl]amino benzoyl chloride. M/Z of [M−H]⁻=507. ¹H NMR (CDCl₃) δ=3.85 (s, 3H), 4.45 (sd, 2H), 6.45 (br, 1H), 6.8–7.0 (2H), 7.15–7.2 (2H), 7.3–7.5 (3H), 7.55–7.6 (1H), 7.6–7.65 (2H), 10.65 (1H).

EXAMPLE 9

5-Bromo-2-[(4'-trifluoromethoxyphenyl)sulfonyl]amino-N-(4''-methylbenzyl)benzamide

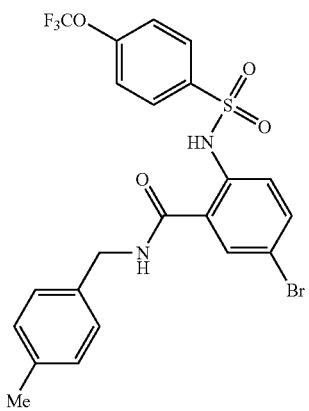

This compound was prepared using the procedure described in Example 4, using 4-methyl benzyl amine instead of 2-methoxy benzyl amine. M/Z for [M−H]⁻=541. ¹H NMR (DMSO) δ=2.3 (s, 3H), 4.35 (sd, 2H), 7.1–7.2 (4H), 7.4–7.5 (3H), 7.65–7.7 (1H), 7.8–7.85 (2H), 7.9–8.0 (1H), 9.4 (1H), 11.6 (1H).

EXAMPLE 10

5-Bromo-2-[(4'-chlorophenyl)sulfonyl]amino-N-(2''-trifluoromethoxybenzyl)benzamide

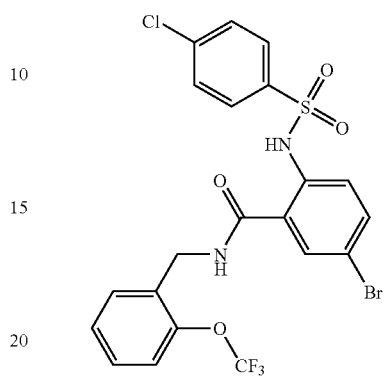

This compound was prepared using the procedure described in Example 4, using 2-trifluoromethoxy benzyl amine instead of 2-methoxy benzyl amine and 5-bromo-2-[(4'-chlorophenyl)sulfonyl]amino benzoyl chloride instead of 5-bromo-2-[(4'-trifluoromethoxyphenyl)sulfonyl]amino benzoyl chloride. M/Z for [M−H]⁻=561. ¹H NMR (DMSO) δ=4.4 (sd, 2H), 7.38–7.5 (5H), 7.55–7.62 (2H), 7.7–7.8 (3H), 7.95–8.0 (1H), 9.4 (br, 1H), 11.4 (br, 1H).

EXAMPLE 11

N-[5-Bromo-2-(4'-trifluoromethoxy-benzenesulfonylamino)-phenyl]-2-(3''-methoxy phenyl)-acetamide

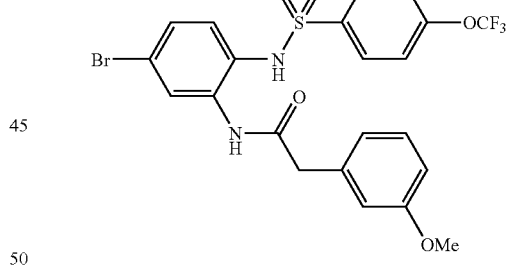

N-(2-amino-4-bromo phenyl)-4-(trifluoromethoxy)-benzene sulfonamide (0.042 g, 0.1 mmol) was dissolved in tetrahydrofuran (1 mL). The mixture was cooled below 5° C. in an ice bath. 3-Methoxy phenyl acetyl chloride (55 μL, 0.3 mmol) and triethyl amine (45 μL, 0.32 mmol) were added to the mixture. The mixture was warmed to room temperature and the solvent was removed to dryness. The resulting residue was partitioned between HCl (1M, 1 mL) and ethyl acetate (2 mL). The organic solvent was collected. The solvent was removed to dryness and the resulting solid was dissolved in ethyl acetate (2×5 mL). The crude product was purified by column chromatography using a 50/50 mixture of hexane and ethyl acetate. M/Z of [M−H]⁻=559. ¹H NMR (CDCl₃) δ=3.7 (s, 2H), 3.85 (s, 3H), 6.6–6.7 (1H), 6.8–7.0 (4H), 7.1–7.15 (1H), 7.2–7.3 (2H), 7.3–7.4 (1H), 7.6–7.65 (2H), 7.8–7.9 (2H).

EXAMPLE 12

5-Bromo-2-[(4'-chlorophenyl)sulfonyl]amino-N-(2'-chlorophenyl)benzamide

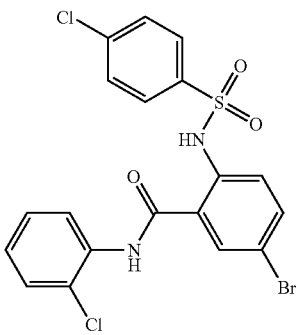

This compound was prepared using the procedure described in Example 4, using 2-chloro aniline instead of 2-methoxy benzyl amine and 5-bromo-2-[(4'-chlorophenyl)sulfonyl]amino benzoyl chloride instead of 5-bromo-2-[(4'-trifluoromethoxyphenyl)sulfonyl]amino benzoyl chloride. M/Z of [M−H]⁻=497. ¹H NMR (CDCl₃) δ=7.15–7.2 (1H), 7.25–7.3 (2H), 7.35–7.4 (1H), 7.45–7.5 (1H), 7.6–7.7 (5H), 8.0 (br, 1H), 8.25–8.30 (1H), 101.1 (1H).

EXAMPLE 13

5-Bromo-2-[(4'-chloro-3'-nitrophenyl)sulfonyl]amino-N-(2'-methoxyphenyl)benzamide

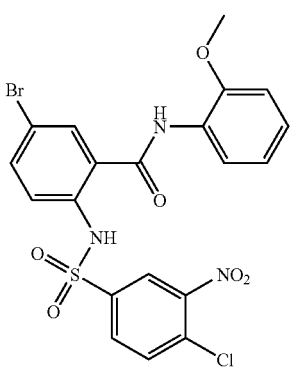

This compound was prepared using the procedure described in Example 4, using 2-methoxy aniline instead of 2-methoxy benzyl amine and 5-bromo-2-[(4'-chloro-3'-nitrophenyl)sulfonyl]amino benzoyl chloride instead of 5-bromo-2-[(4'-trifluoromethoxyphenyl)sulfonyl]amino benzoyl chloride. M/Z of [M−H]⁻=538, ¹H NMR (DMSO) δ=3.8 (s, 3H), 6.85–6.95 (1H), 7.0–7.08 (1H), 7.1–7.2 (2H), 7.6–7.78 (2H), 7.82–7.96 (3H), 8.3 (1H).

EXAMPLE 14

5-Bromo-2-[(4'-methoxy-3'-nitrophenyl)sulfonyl]amino benzoic acid

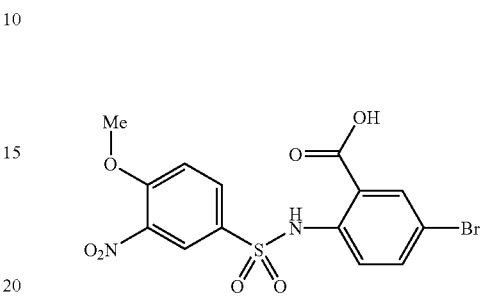

This compound was prepared by hydrolysis of methyl 5-bromo-2-[(4'-chloro-3'-nitrophenyl)sulfonyl]amino benzoate using the procedure described in Example 2 using a mixture of methanol (3)/water(1) instead of tetrahydrofuran/water. M/Z of [M−H]⁻=429.

EXAMPLE 15

5-Bromo-2-[(4'-methoxy-3'-nitrophenyl)sulfonyl]amino-N-(3'-bromophenyl)benzamide

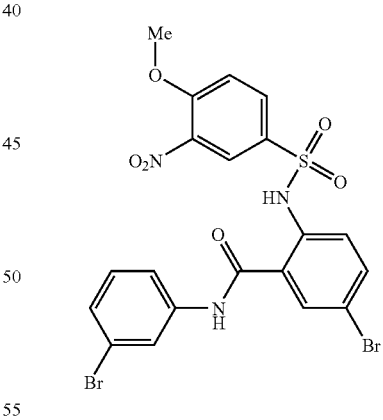

This compound was prepared using the procedure described in Example 4, using 3-bromo aniline instead of 2-methoxy benzyl amine and 5-bromo-2-[(4'-methoxy-3'-nitrophenyl)sulfonyl]amino benzoyl chloride instead of 5-bromo-2-[(4'-trifluoromethoxyphenyl)sulfonyl]amino benzoyl chloride. M/Z of [M−H]⁻=582, ¹H NMR (DMSO) δ=3.8 (s, 3H), 7.24–7.28 (3H), 7.32–7.38 (1H), 7.48–7.54 (1H), 7.62–7.68 (1H), 7.78–7.82 (1H), 7.86–7.92 (2H), 8.14 (1H), 10.2 (1H), 10.4 (1H).

EXAMPLE 16

5-Bromo-2-[(4'-methoxy-3'-nitrophenyl)sulfonyl]amino-N-(2'-fluorophenyl)benzamide

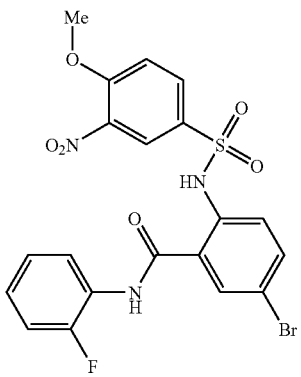

This compound was prepared using the procedure described in Example 4, using 2-fluoro aniline instead of 2-methoxy benzyl amine and 5-bromo-2-[(4'-methoxy-3'-nitrophenyl)sulfonyl]amino benzoyl chloride instead of 5-bromo-2-[(4'-trifluoromethoxyphenyl)sulfonyl]amino benzoyl chloride M/Z of [M−H]⁻=522, ¹H NMR (DMSO) δ=3.95 (s, 3H), 7.14–7.3 (4H), 7.4–7.44 (1H), 7.56–7.7 (2H), 7.9–7.96 (2H), 8.2 (1H), 10.4 (1H), 10.8 (1H).

EXAMPLE 17

5-Bromo-2-[(3'-nitrophenyl)sulfonyl]amino-N-(3',4'-dichlorophenyl)benzamide

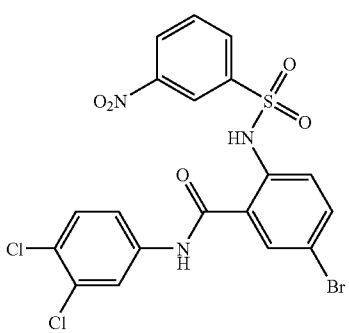

This compound was prepared using the procedure described in Example 4, using 3,4-dichloro aniline instead of 2-methoxy benzyl amine and 5-bromo-2-[(3'-nitrophenyl)sulfonyl]amino benzoyl chloride instead of 5-bromo-2-[(4'-trifluoromethoxyphenyl)sulfonyl]amino benzoyl chloride. ¹H NMR (DMSO) δ=7.22–7.28 (1H), 7.44–7.5 (1H), 7.58–7.62 (1H), 7.68–7.82 (3H), 7.94 (1H), 8.06–8.1 (1H), 8.32–8.36 (1H), 8.42 (1H).

EXAMPLE 18

5-Bromo-2-[(4'-chloro-3'-nitrophenyl)sulfonyl]amino-N-(2',5'-dichlorophenyl) benzamide

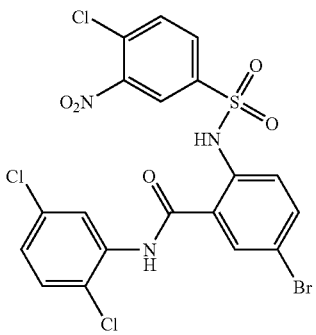

This compound was prepared using the procedure described in Example 4, using 2,5-dichloro aniline instead of 2-methoxy benzyl amine and 5-bromo-2-[(4'-chloro-3'-nitrophenyl)sulfonyl]amino benzoyl chloride instead of 5-bromo-2-[(4'-trifluoromethoxyphenyl)sulfonyl]amino benzoyl chloride. ¹H NMR (DMSO) δ=7.2–7.25 (1H), 7.3–7.4 (1H), 7.58–7.62 (1H), 7.6–7.7 (1H), 7.8–8.9 (4H), 8.32–8.36 (1H).

EXAMPLE 19

2-[(4'-Chloro-3'-nitrophenyl)sulfonyl]amino benzoic acid

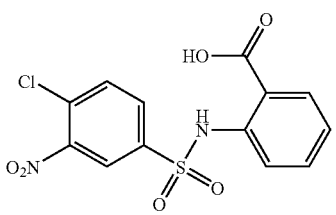

This compound was prepared using the procedures described in Examples 1 and 2 using methyl anthralinate instead of methyl 5-bromo-2-amino benzoate and 4-chloro-3-nitrobenzene sulfonyl chloride instead of 4-trifluoromethoxybenzene sulfonyl chloride. M/Z of [M−H]⁻=355.

EXAMPLE 20

5-Bromo-2-[(2',5'-dichloro thiophene)-3-sulfonyl]amino benzoic acid

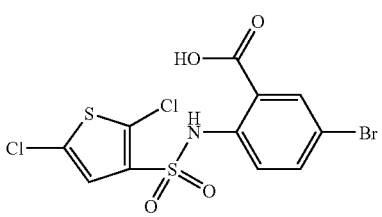

This compound was prepared using the procedures described in Examples 1 and 2 using 2,5-dichloro thiophene-3-sulfonyl chloride instead of 4-trifluoromethoxybenzene sulfonyl chloride. M/Z for [M–H]⁻=427.

EXAMPLE 21

5-Bromo-2-[benzothiophene-3-sulfonyl]amino benzoic acid

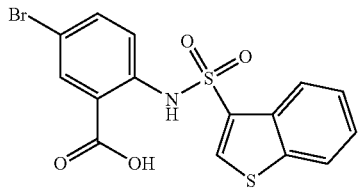

This compound was prepared using the procedures described in Examples 1 and 2 using benzothiophene-3-sulfonyl chloride instead of 4-trifluoromethoxybenzene sulfonyl chloride. M/Z for [M–H]⁻=410.

EXAMPLE 22

5-Bromo-2-[(4-pentyl phenyl)sulfonyl]amino benzoic acid

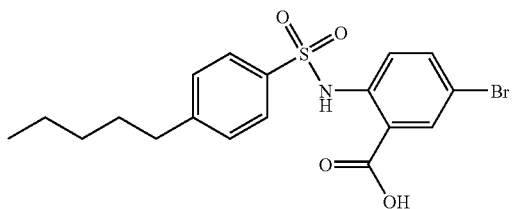

This compound was prepared using the procedures described in Examples 1 and 2 using 4-pentyl phenylsulfonyl chloride instead of 4-trifluoromethoxybenzene sulfonyl chloride. M/Z for [M–H]⁻=424.

EXAMPLE 23

5-Bromo-2-[quinoline-8-sulfonyl]amino benzoic acid

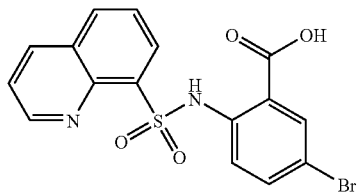

This compound was prepared using the procedures described in Examples 1 and 2 using 8-quinoline-sulfonyl chloride instead of 4-trifluoromethoxybenzene sulfonyl chloride. M/Z for [M–H]⁻=405.

EXAMPLE 24

5-Bromo-2-[(3',5'-dimethyl isoxazole)-4-sulfonyl]amino benzoic acid

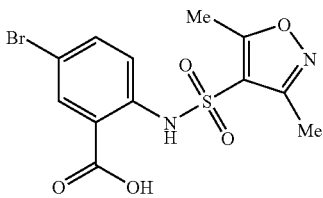

This compound was prepared using the procedures described in Examples 1 and 2 using 3,5-dimethyl isoxazole-4-sulfonyl chloride instead of 4-trifluoromethoxybenzene sulfonyl chloride. M/Z for [M–H]⁻=373.

EXAMPLE 25

5-Bromo-2-[(4'-trifluoromethoxyphenyl)sulfonyl]amino-N-[ethyl-2-(2'-methoxyphenyl)]benzamide

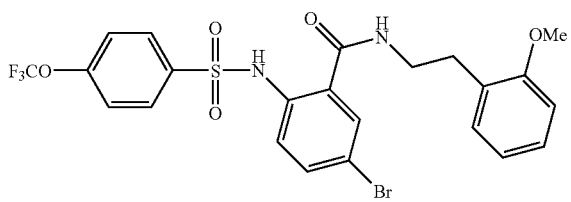

This compound was prepared using the procedure described in Example 4, using 2-methoxy phenyl ethyl amine instead of 2-methoxy benzyl amine. M/Z for [M–H]⁻=571. ¹H NMR (DMSO) δ=2.8 (t, 2H), 3.3 (2H), 3.8 (s, 3H), 6.8–6.9 (1H), 6.95–7.0 (1H), 7.1–7.15 (1H), 7.18–7.23 (1H), 7.41–7.45 (1H), 7.5–7.6 (2H), 7.65–7.75 (1H), 7.8–7.9 (3H). 9.0 (br, 1H), 11.6 (br, 1H).

EXAMPLE 26

N-(4-nitrophenyl)-4(trifluromethoxy)-benzene sulfonamide

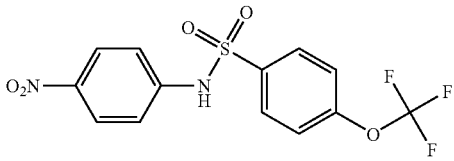

This compound was prepared using the procedure described in Example 1, using 4-nitro aniline instead of methyl 2-amino-5-bromo benzoate. M/Z for [M–H]⁻=362. ¹H NMR (DMSO) δ=7.3–7.4 (2H), 7.55–7.65 (2H), 7.95–8.05 (2H), 8.15–8.25 (2H), 11.4 (H).

EXAMPLE 27

N-(4-methyl benzyl)-4-(trifluoromethoxy)-benzene sulfonamide

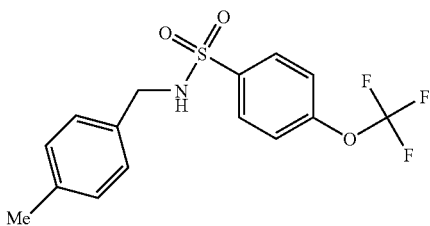

This compound was prepared using the procedure described in Example 1, using 4-methyl benzyl amine instead of methyl 2-amino-5-bromo benzoate. M/Z for [M–H]⁻=344. $^1$H NMR (CDCl$_3$) δ=2.3 (s, 3H), 4.15 (sd, 2H), 7.0–7.15 (4H), 7.2–7.35 (2H), 7.8–7.9 (2H).

EXAMPLE 28

N-[2-Chloro benzyl]-4-(trifluoromethoxy)-benzene sulfonamide

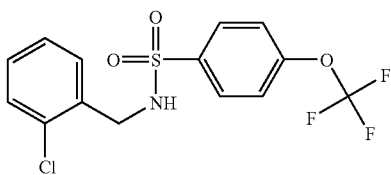

This compound was prepared using the procedure described in Example 1, using 2-chloro benzyl amine instead of methyl 2-amino-5-bromo benzoate. M/Z for [M–H]⁻=364. $^1$H NMR (CDCl$_3$) δ=4.3 (sd, 2H), 5.65 (1H), 7.05–7.3 (6H), 7.7–7.75 (2H).

EXAMPLE 29

N-(4-methylthio)-4-(trifluoromethoxy)-benzene sulfonamide

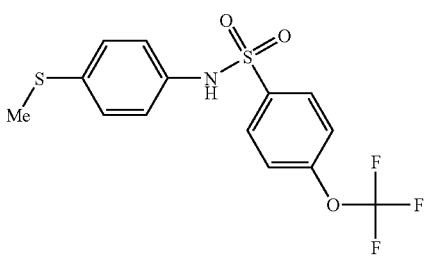

This compound was prepared using the procedure described in Example 1, using 4-methylthio aniline instead of methyl 2-amino-5-bromo benzoate. M/Z for [M–H]⁻=362. $^1$H NMR (CDCl$_3$) δ=2.4 (s, 3H), 6.5 (s, 1H), 6.95–7.05 (2H), 7.15–7.2 (2H), 7.25–7.3 (2H), 7.75–7.8 (2H).

EXAMPLE 30

N-(4-bromo-2-nitro)-4(trifluoromethoxy)-benzene sulfonamide

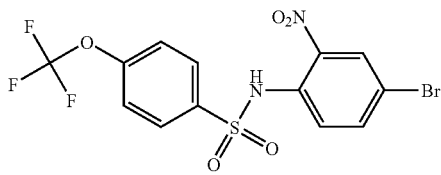

This compound was prepared using the procedure described in Example 1, using 4-bromo-2-nitro aniline instead of methyl 2-amino-5-bromo benzoate. Product was obtained as the minor product in ~10% yield. M/Z for [M–H]⁻=439 $^1$H NMR (CDCl$_3$) δ=7.3–7.35 (2H), 7.38–7.42 (1H), 7.7–7.75 (1H), 7.76–7.8 (1H), 7.88–7.92 (2H), 7.95–8.05 (1H), 8.3 (1H).

EXAMPLE 31

N-(trifluoromethoxy phenyl)-N'-(4-bromo-2-nitro phenyl)-4-(trifluoromethoxy)-benzene sulfonamide

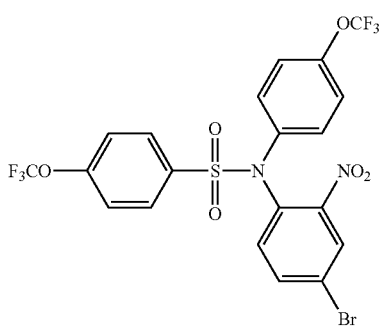

This compound was prepared using the procedure described in Example 1, using 4-bromo-2-nitro aniline instead of methyl 2-amino-5-bromo benzoate. Product was obtained as the main product. M/Z for [M–H]⁻=599. $^1$H NMR (CDCl$_3$) δ=6.98–7.02 (1H), 7.38–7.42 (4H), 7.73–7.78 (1H), 8.0–8.06 (4H), 8.2 (1H).

EXAMPLE 32

N-(2-amino-4-bromo phenyl)-4-(trifluoromethoxy)benzene sulfonamide

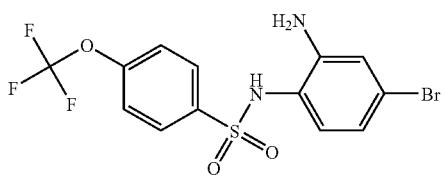

N-(4-bromo-2-nitro)-4(trifluoromethoxy)-benzene sulfonamide (0.406 g, 0.92 mmol) was dissolved in a mixture of tetrahydrofuran (5 mL) and methanol (15 mL). The mixture was cooled below 5° C. using an ice bath. BiCl₃ (0.696 g, 2.2 mmol, 2.2 equivalents) was added. NaBH₄ (0.203 g, 5.4 mmol, 5.5 equivalents) was added slowly to the mixture. A black precipitate formed immediately. The mixture was warmed to room temperature, centrifuged and the solid was discarded. The solution was concentrated to dryness. The resulting residue was purified by column chromatography using 20% ethyl acetate in hexane. ¹H NMR (CDCl₃) δ=4.1–4.3 (br, 2H), 6.0 (1H), 6.2–6.3 (1H), 6.6–6.7 (1H), 6.9–7.0 (1H), 7.36–7.4(2H), 7.72–7.76 (2H).

EXAMPLE 33

N-(4-trifluoromethoxy phenyl)-N'-(2-amino-4-bromo phenyl)-4-(trifluoromethoxy)-benzene sulfonamide

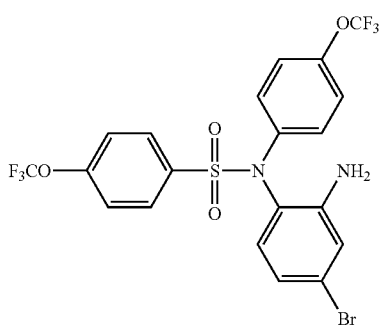

This compound was prepared using the procedure described in Example 32, using N-(trifluoromethoxy phenyl)-N'-(4-bromo-2-nitro phenyl)-4-(trifluoromethoxy)-benzene sulfonamide instead of N-(4-bromo-2-nitro)-4(trifluoromethoxy)-benzene sulfonamide. ¹H NMR (CDCl₃) δ=5.0 (1H), 6.35–6.4 (1H), 6.95–7.05 (1H), 7.2–7.3.5 (1H), 7.38–7.45 (4H), 7.6 (1H), 8.0–8.1 (4H).

EXAMPLE 34

N-(4-phenoxy phenyl)-4-(trifluoromethoxy)benzene sulfonamide

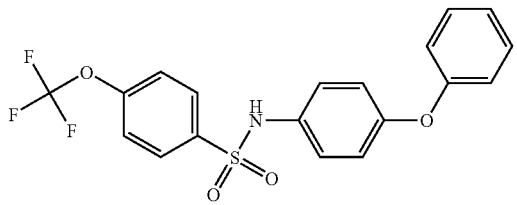

This compound was prepared using the procedure described in Example 1, using 4-phenoxy aniline instead of methyl 2-amino-5-bromo benzoate. M/Z for [M–H]⁻=408, ¹H NMR (CDCl₃) δ=6.8–7.05 (6H), 7.1 (1H), 7.2–7.4 (4H), 7.8 (2H).

EXAMPLE 35

N (4-iodo-2-fluorophenyl)-4-(trifluoromethoxy)benzene sulfonamide

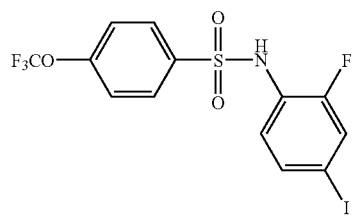

This compound was prepared using the procedure described in Example 1, using 2-fluoro-4-iodo aniline instead of methyl 2-amino-5-bromo benzoate. ¹H NMR (CDCl₃) δ=7.1–7.45 (5H), 7.8 (2H), 9.8 (1H).

EXAMPLE 36

N-(2-methoxy benzyl)-4-trifluoromethoxy benzene sulfonamide

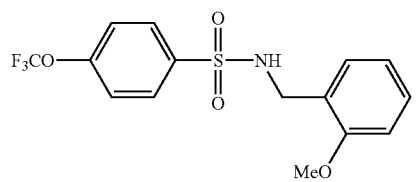

This compound was prepared using the procedure described in Example 1, using 2-methoxy benzyl amine instead of methyl 2-amino-5-bromo benzoate. M/Z for [M–H]⁻=360. ¹H NMR (d-MeOH) δ=3.65 (s, 3H), 4.2 (s, 2H), 6.65–6.8 (2H), 7.05–7.12 (2H), 7.2–7.3 (2H), 7.7 (2H).

EXAMPLE 37

N-(2-trifluoromethyl benzyl)-4-(trifluoromethoxy)benzene sulfonamide

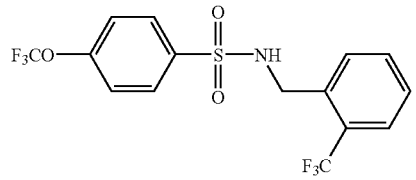

This compound was prepared using the procedure described in Example 1, using 2-trifluoromethyl benzyl amine instead of methyl 2-amino-5-bromo benzoate. M/Z for [M–H]⁻=398.

EXAMPLE 38

3-(3-Fluoro-phenyl)-1-(4-hydroxy-phenyl)-propenone

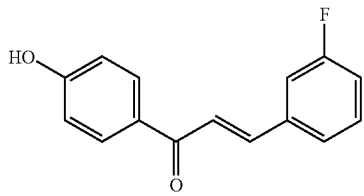

In a vial, 3-fluorobenzaldehyde (1.0 g) and 4-hydroxyacetophenone (0.9 g) were stirred in methanol (30 mL). NaOH (1.4 mL of 50% w/v aqueous solution) was added at room temperature. The reaction mixture was left to stir overnight. The crude material was neutralized with 1 N HCl and extracted with ethyl acetate (100 mL). The organic layer was separated and dried over sodium sulfate. The drying agent was filtered away, and solvent was removed. The crude product was dissolved in acetone. Hexane was added until a precipitate was obtained. The solid was collected by filtration and dried, giving yellow crystals: 1.2 g (67% yield). $^1$H NMR (400 MHz, DMSO) δ=6.8 (d, 2H), 7.2 (m, 1H), 7.4 (m, 1H), 7.6 (s, 1H), 7.6 (d, 1H), 7.75 (d, 1H), 7.9 (d, 1H), 8.0 (d, 2H); MS calculated: m/z=242, found: m/e 242.

EXAMPLE 39

3-Furan-2-yl-1-(4-hydroxy-phenyl)-propenone

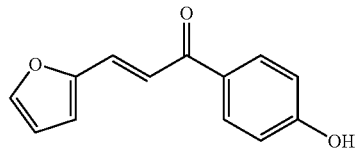

In a vial, 2-furaldehyde (1.0 g) and 4-hydroxyacetophenone (1.2 g) were stirred in methanol (30 mL). NaOH (1.8 mL of 50% w/v aqueous solution) was added at room temperature. The reaction mixture was left to stir overnight. The crude material was neutralized with 1 N HCl and extracted with ethyl acetate (100 mL). The organic layer was separated, dried over sodium sulfate, and solvent was removed. The resulting residue (1.4 g, 75% yield) was pure by $^1$H NMR.

EXAMPLE 40

3-Furan-2-yl-1-(4-methoxy-phenyl)-propenone

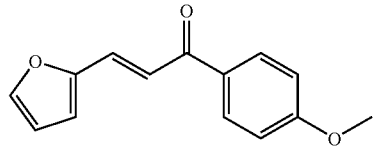

In a vial, 2-furaldehyde (1.0 g) and 4-phenoxyacetophenone (1.3 g) were stirred in methanol (30 mL). NaOH (1.8 mL of 50% w/v aqueous solution) was added at room temperature. The reaction mixture was left to stir overnight. The crude material was neutralized with 1 N HCl and extracted with ethyl acetate (100 mL). The organic layer was separated, dried over sodium sulfate, and solvent was removed. The resulting residue (1.2 g, 69.5% yield) was pure by $^1$HNMR.

EXAMPLE 41

3-Furan-2-yl-1-(4-phenoxy-phenyl)-propenone

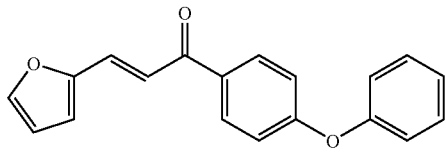

In a vial, 2-furaldehyde (1.0 g) and 4-phenoxyacetophenone (1.8 g) were stirred in methanol (30 mL). NaOH (1.8 mL of 50% w/v aqueous solution) was added at room temperature. The reaction mixture was left to stir overnight. The next day, the crude solid product was collected by filtration and was triturated in methanol. The solid was then dried, giving the desired pure enone in 71% yield (1.8 g).

EXAMPLE 42

3-(3-Fluoro-phenyl)-1-(4-methoxy-phenyl)-propenone

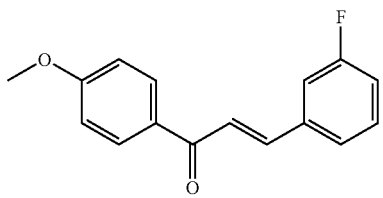

In a vial, 3-fluorobenzaldehyde (1.0 g) and 4-methoxyacetophenone (1.0 g) were stirred in methanol (30 mL). NaOH (1.4 mL of 50% w/v aqueous solution) was added at room temperature. The reaction mixture was left to stir overnight. The next day, the crude solid product was collected by filtration and was triturated in methanol. The solid was then dried, giving the desired enone in 70% yield (1.2 g).

EXAMPLE 43

3-(3-Fluoro-phenyl)-1-(4-phenoxy-phenyl)-propenone

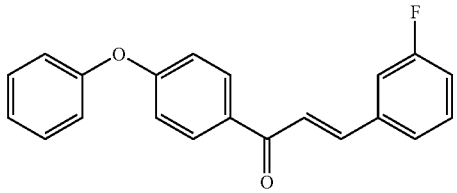

In a vial 3-fluorobenzaldehyde (1.0 g) and 4-phenoxyacetophenone (1.4 g) were stirred in methanol (30 mL). NaOH (1.4 mL of 50% w/v aqueous solution) was added at room temperature. The reaction mixture was left to stir overnight. The next day, the crude solid product was collected by filtration and was triturated in methanol. The solid was then dried, giving the desired pure enone in 75% yield (1.6 g).

EXAMPLE 44

4-[5-(3-Fluoro-phenyl)-1-methyl-1H-pyrazol-3-yl]-phenol

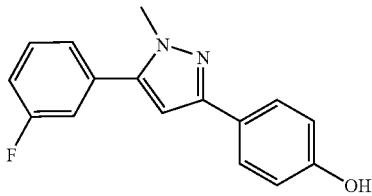

In an open vial, 0.4 g of 3-(3-fluoro-phenyl)-1-(4-hydroxy-phenyl)-propenone was dissolved in dimethylsulfoxide (10 mL), 1 g of methylhydrazine was added and the reaction mixture was heated to 85° C. for 3 days. The disappearance of starting material was monitored by TLC (silica/30% EtOAc-hexanes). TLC also monitored the disappearance of the pyrazoline intermediate. The desired pyrazole has higher Rf-value than the pyrazoline intermediate. The reaction was cooled to room temperature and ethyl acetate (100 mL) and water (50 mL) were added. The organic layer was washed twice with water (25 mL), then separated and dried over sodium sulfate. The solvent was removed after filtering away the drying agent. Purification through a short column of silica (eluted with 30% ethylacetate-hexanes) and crystallization from acetone/hexanes gave the desired pyrazole in moderate yield. (0.15 g, 34% yield). $^1$H NMR (400 MHz, DMSO) δ=3.9 (d, 3H), 6.8 (d, 2 H), 6.8 (s, 1H), 7.3 (m, 1H), 7.45 (m, 2 H), 7.6 (m, 1H), 7.65 (d, 2H); MS calculated: m/e 268, found: m/e 268.

EXAMPLE 45

4-(5-Furan-2-yl-1-methyl-1H-pyrazol-3-yl)-phenol

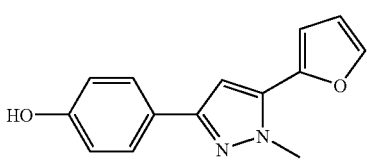

In an open vial, 3-furan-2-yl-1-(4-hydroxy-phenyl)-propenone (0.4 g) was dissolved in dimethylsulfoxide (10 mL). 1 g of methylhydrazine was added and the reaction mixture was heated to 85° C. for 2 days. Following the workup and the purification as described in Example 44, the desired pyrazole was obtained in a moderate yield (0.1 g).

EXAMPLE 46

5-(3-Fluoro-phenyl)-1-methyl-3-(4-phenoxy-phenyl)-1H-pyrazole

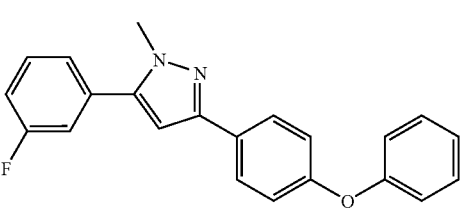

In an open vial, 3-(3-fluoro-phenyl)-1-(4-phenoxy-phenyl)-propenone (0.4 g) was dissolved in dimethylsulfoxide (10 mL). Methylhydrazine (1.0 g) was added and the reaction mixture was heated to 85° C. for 3 days. The reaction mixture was cooled to room temperature and ethyl acetate (100 mL) and water (50 mL) were added. The organic layer was washed twice with water (25 mL), then separated and dried over sodium sulfate. The solvent was removed after filtering away the drying agent. Purification by column chromatography (silica, eluted with ethyl acetate-hexanes, 1:9) gave the desired pyrazole in poor yield (0.075 g).

EXAMPLE 47

5-(3-Fluoro-phenyl)-3-(4-methoxy-phenyl)-1-methyl-1H-pyrazole

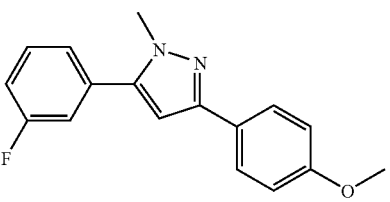

In an open vial, 3-(3-fluoro-phenyl)-1-(4-methoxy-phenyl)-propenone (0.4 g) was dissolved in dimethylsulfoxide (10 mL). Methylhydrazine (1.0 g) was added and the reaction mixture was heated to 85° C. for 3 days. The reaction was cooled to room temperature and ethyl acetate (100 mL) and water (50 mL) were added. The organic layer was washed twice with water (25 mL), then separated and dried over sodium sulfate. The solvent was removed after filtering away the drying agent. Purification by column chromatography (silica eluted with ethyl acetate-hexanes, 1:9) gave the desired pyrazole in moderate yield (0.174 g).

EXAMPLE 48

5-Furan-2-yl-3-(4-methoxy-phenyl)-1-methyl-1H-pyrazole

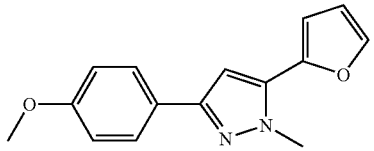

In an open vial, 3-furan-2-yl-1-(4-methoxy-phenyl)-propenone (0.4 g) was dissolved in dimethylsulfoxide (10 mL). Methylhydrazine (1.0 g) was added and the reaction mixture was heated to 85° C. for 3 days. The reaction was cooled to room temperature and ethyl acetate (100 mL) and water (50 mL) were added. The organic layer was washed twice with water (25 mL), then separated and dried over sodium sulfate. The solvent was removed after filtering away the drying agent. Purification by column chromatography (silica, eluted with ethyl acetate-hexanes, 1:9) gave the desired pyrazole in moderate yield (0.096 g).

EXAMPLE 49

5-Furan-2-yl-1-methyl-3-(4-phenoxy-phenyl)-1H-pyrazole

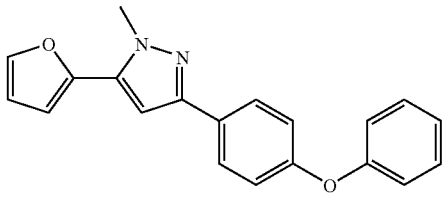

In an open vial, 3-furan-2-yl-1-(4-phenoxy-phenyl)-propenone (0.4 g) was dissolved in dimethylsulfoxide (10 mL). Methylhydrazine (1.0 g) was added and the reaction mixture was heated to 85° C. for 3 days. The reaction mixture was cooled to room temperature and ethyl acetate (100 mL) and water (50 mL) were added. The organic layer was washed twice with water (25 mL), then separated and dried over sodium sulfate. The solvent was removed after filtering away the drying agent. Purification by column chromatography (silica, eluted with ethyl acetate-hexanes, 1:9) gave the desired pyrazole in moderate yield (0.1 g).

EXAMPLE 50

4-(5-Furan-2-yl-isoxazol-3-yl)-phenol

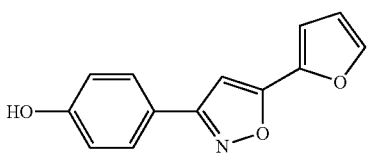

To a mixture of 3-furan-2-yl-1-(4-hydroxy-phenyl)-propenone (0.4 g, 1.9 mmol) and hydroxylamine hydrochloride (0.2 g, 2.85 mmol) was added sodium hydroxide (0.15 g, 2.8 mmol). The reaction mixture was heated to reflux for 3 days. The mixture was then concentrated, and neutralized with diluted HCl. Ethyl acetate and water were then added, and the mixture was shaken. The organic layer was separated and dried over sodium sulfate. The solvent was removed and the residue was purified by column chromatography (eluted with 20% ethyl acetate/hexanes) to give the desired isoxazole in poor yield (50 mg). $^1$H NMR (400 MHz, DMSO) δ=6.65 (d, 1H), 6.85 (d, 2H), 7.05 (d, 1H), 7.15 (s, 1H), 7.75 (d, 2H), 7.85 (d, 1H). MS calculated=m/e 227, found=m/e 227.

EXAMPLE 51

5-Furan-2-yl-3-(4-methoxy-phenyl)-isoxazole

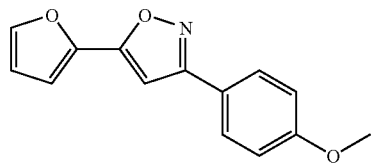

To a mixture of 3-furan-2-yl-1-(4-methoxy-phenyl)-propenone (0.4 g, 1.75 mmol) and hydroxylamine hydrochloride (0.18 g, 2.6 mmol), was added sodium hydroxide (0.14 g, 3.5 mmol). The reaction mixture was heated to reflux for 3 days. The mixture was then concentrated, and neutralized with diluted HCl. Then ethyl acetate and water were added. The organic layer was separated and dried over sodium sulfate. The solvent was removed and the residue was purified by column chromatography (silica, eluted with 20% ethyl acetate/hexanes) to give the desired isoxazole in poor yield (10 mg).

EXAMPLE 52

5-Furan-2-yl-3-(4-phenoxy-phenyl)-isoxazole

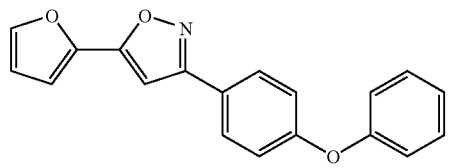

To a mixture of 3-furan-2-yl-1-(4-phenoxy-phenyl)-propenone (0.4 g, 1.4 mmol) and hydroxylamine hydrochloride (0.14 g, 2.1 mmol), was added sodium hydroxide (0.11 g, 2.8 mmol). The reaction mixture was heated to reflux for 3 days. The mixture was then concentrated, and neutralized with diluted HCl. Ethyl acetate and water were added. The organic layer was separated and dried over sodium sulfate. The solvent was removed and the residue was purified by column chromatography (silica, eluted with 20% ethyl acetate/hexanes) to give the desired isoxazole in poor yield (10 mg).

EXAMPLE 53

1,3-Bis-(3-trifluoromethyl-phenyl)-urea

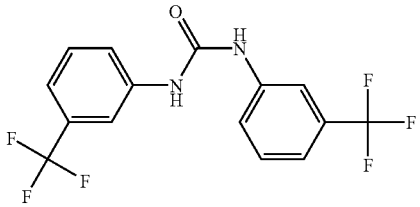

In a round bottom flask under nitrogen, α,α,α-trifluro-m-tolyl isocyanate (3 g, 16 mmol) was dissolved in anhydrous dichloromethane (40 mL). 3-(Trifluoromethyl) aniline (2 g, 12.4 mmol) was added through a syringe at room temperature. A precipitate was formed 15 minutes after the completion of the addition. The reaction was left to stir overnight at room temperature. The next day the white solid was collected by filtration, washed with dichloromethane and dried. This solid corresponds to the desired urea. (4.2 g, 97% yield). $^1$H NMR (400 MHz, DMSO) δ 7.35 (d, 2H), 7.55 (m, 2 H), 7.6 (d, 2H), 8.05 (s, 2H). MS calculated=m/e 348, found=m/e 348.

EXAMPLE 54

2-Iodo-4-bromoacetanilide

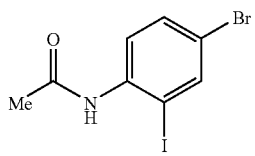

To a mixture of 900 mL of MeOH and 100 mL water 4-bromoaniline (40.0 g, 0.232 mol) was added and the resulting solution was cooled in an ice bath. To this 35 mL of concentrated $H_2SO_4$ was added followed by a 1 M solution of ICl (255 mL 0.232 mol) in $CH_2Cl_2$. The bath was then removed and the reaction was stirred overnight. The volatiles were then removed by rotary evaporation, 200 mL of ice water was added to the product along with 500 mL $CH_2Cl_2$. The mixture was made strongly basic with 1 M NaOH and then extracted (3×$CH_2Cl_2$). The combined extracts were dried with $Na_2SO_4$ and then concentrated and dried in vacuo to give 2-iodo-4-bromoaniline. $^1$H-NMR (400 MHz, $CDCl_3$): δ 4.1 (s, 2H, NH), 6.60 (m, 1H, NCH), 7.22 (m, 1H, CHCH), 7.77 (s, 1H, ICCHCBr). The crude product was then added to a mixture of acetyl chloride (36.0 g, 0.472 mol) and pyridine (56.0 g, 0.708 mol) in 1 L of dry THF cooled in an ice bath. The bath was then removed and the resulting mixture was stirred at room temperature overnight. THF was removed by rotary evaporation and then 400 mL of ice water was added. The product was extracted with $CH_2Cl_2$ (3×300 mL) and then the layers were combined and dried with $Na_2SO_4$. Silica column chromatography using mixtures of EtOAc and hexanes gave 12 g of 2-Iodo-4-bromoacetanilide. $^1$H-NMR (400 MHz, $CDCl_3$): δ=2.24 (s, 3H, CH$_3$), 7.39 (s, 1H, NH), 7.46 (d, 8.4 Hz, 1H, BrCCH), 7.90 (s, 1H, ICCHCBr), 8.13 (d, 8.0 Hz, 1H, NCCH).

EXAMPLE 55

2-Diethylphosphono-4-bromoacetanilide

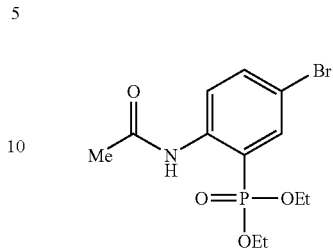

To a 30 mL vial, 2-Iodo-4-bromoacetanilide (3.25 g, 9.23 mmol) was added along with triethylphosphite (2.31 g, 13.8 mmol) and $PdCl_2$ (113 mg, 0.641 mmol). The vial was flushed with $N_2$ sealed and then heated at 130° C. while stirring for 30 h. The resulting solution was cooled to room temperature, dissolved in a 1:1 mixture of EtOAc/hexane and then purified on a silica column using mixtures of EtOAc/hexanes to give 2.70 g of 2-Diethylphosphono-4-bromoacetanilide as a white solid. $^1$H-NMR (400 MHz, $CDCl_3$): δ=1.36 (s, 6H, 6.8 Hz, $CH_2CH_3$), 2.20 (s, 3H, CH$_3$), 4.10 (m, 4H, CH$_2$), 7.66 (m, 2H, CHBrCCH), 8.54 (m, 1H, NCCH), 10.6 (s, 1H, NH).

EXAMPLE 56

2-Diethylphosphono-4-bromoaniline

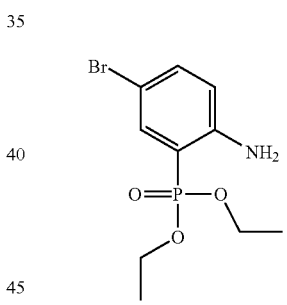

To an oven dried 250 mL round bottom flask, Na (1.2 g, 52.2 mmol) was added along with a stirring bar. The flask was flushed with $N_2$ and then cooled in an ice bath. The flask was sealed with a rubber septum containing a $N_2$ inlet, then 100 mL of anhydrous EtOH was added slowly by syringe. The resulting mixture was stirred until all the Na dissolved and then 2.8 mL of this solution was added to an oven dried vial containing a stirring bar and 2-Diethylphosphono-4-bromoacetanilide (0.400 g, 0.114 mmol) which was dried in vacuo/$P_2O_5$. The vial was flushed with $N_2$, sealed and then heated at 65° C. for 5 h. The resulting solution was cooled to room temperature and then concentrated to dryness by rotary evaporation. The residue was dissolved with 3 mL of $CHCl_3$ and then purified by silica column chromatography using EtOAc as the eluting solvent. This gave 220 mg (63%) of a tan solid. $^1$H-NMR (400 MHz, $CDCl_3$): δ=1.30 (t, 6.8 Hz, 6H, CH$_3$), 4.1 (m, 4H, CH$_2$), 6.50 (m, 1H, NCCH), 7.28 (m, 1H, BrCCHCH), 7.5 (m, 1H, PCCHBr). $^{31}$P (400 MHz, $CDCl_3$) 19.95 (s).

EXAMPLE 57

2-Phosphono-4-bromoaniline disodium salt

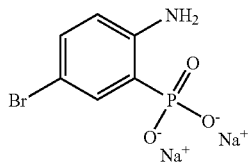

2-Diethylphosphono-4-bromoacetanilide was treated with 20 mL of 6 N HCl in a 30 mL vial containing a stirring bar. The resulting mixture was heated at 100° C. with stirring for 18 hours and was then cooled to room temperature and diluted with 200 mL water. The resulting solution was concentrated by rotary evaporation and then diluted again with 20 mL water and concentrated. The product was recrystallized from a minimum amount of water and then the solid was redissolved in a small amount of water and then this was made basic with 1 N NaOH (pH 10–11). The disodium salt was precipitated by adding isopropanol and the product was dried in vacuo/$P_2O_5$. This gave 0.97 g of 2-phosphono-4-bromoaniline disodium salt as a white solid. $^1$H-NMR (400 MHz, $D_2O$): δ=6.48 (m, 1H, C$\underline{H}$NH), 6.48 (d, 7.6 Hz, 1H, BrC$\underline{H}$CH), 7.44 (d, 1H, BrCC$\underline{H}$CP).

EXAMPLE 58

1-(2-Iodo-4-bromophenyl)-3-(3-trifluoromethylphenyl)urea

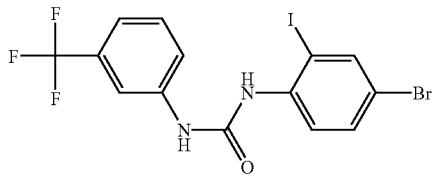

To a 100 mL of anhydrous THF in a 250 mL round bottom flask containing a stirring bar, 2-iodo-4-bromoaniline (2.00 g, 6.70 mmol) was added along with 3-trifluoromethylphenylisocyanate (1.51 g, 7.00 mmol) and 52 mg of pyridine. The resulting solution was heated at 65° C. overnight. THF was removed by rotary evaporation and the product was recrystallized from ethyl acetate to give 3.0 g (92%) of 1-(2-iodo-4-bromophenyl)-3-(3-trifluoromethylphenyl)urea as a white solid.

EXAMPLE 59

1-(2-Diethylphosphono-4-bromophenyl)-3-(3-trifluoromethylphenyl)urea

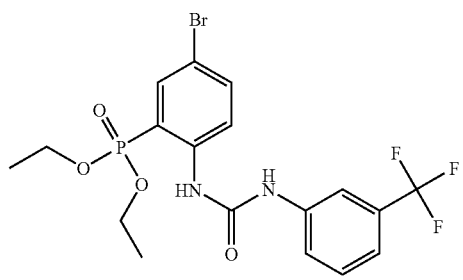

To a 30 mL vial, 1-(2-iodo-4-bromophenyl)-3-(3-trifluoromethylphenyl)urea (2.00 g, 4.12 mmol) was added along with triethylphosphite (1.03 g, 6.0 mmol) and $PdCl_2$ (49 mg, 0.278 mmol). The vial was flushed with $N_2$ sealed and then heated at 130° C. while stirring overnight. The resulting solution was cooled to room temperature, dissolved in a 1:1 mixture of EtOAc/hexane and then purified on a silica column using mixtures of EtOAc/hexanes to give 1.25 g of 1-(2-diethylphosphono-4-bromophenyl)-3-(3-trifluoromethylphenyl)urea as a white solid.

EXAMPLE 60

Parallel Synthesis: 1-(2-diethylphosphono-4-bromophenyl)-3-(3,5-bistrifluoromethylphenyl)urea

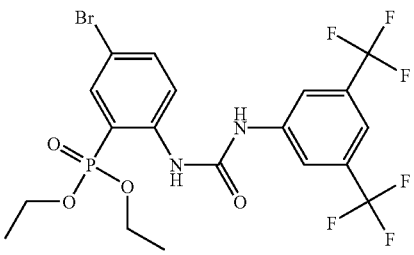

To an oven dried 30 mL vial containing a stirring bar 2 mL of pyridine was added followed by 3,5-bistrifluorometylphenylisocyanate (35 mg, 0.125) and 2-Diethylphosphono-4-bromoaniline (32 mg, 0.104 mmol). The resulting solution was stirred at 65° C. for 3 hours. Pyridine was removed by rotary evaporation and then the product was purified by silica column chromatography using mixtures of EtOAc and hexanes to give 1-(2-diethylphosphono-4-bromophenyl)-3-(3,5-bistrifluoromethylphenyl)urea. $^1$H-NMR (400 MHz, $CDCl_3$): δ=1.32 (t, 6.8 Hz, 6H C$\underline{H}_3$), 4.10 (m, 4H, C$\underline{H}_2$), 7.52 (s, 1H, $CCF_3C\underline{H}CCF_3$), 7,64 (m, 2H, C$\underline{H}$CBRC$\underline{H}$), 8.03 (s, 2H, $CCF_3C\underline{H}CNH$), 8.30 (m, 1H, CPCNC$\underline{H}$), 8.62 (s, 1H, N$\underline{H}$), 9.82 (s, 1H, PCCN$\underline{H}$). $^{31}$P (400 Mz, $CDCl_3$) δ=18.19 (s)

EXAMPLE 61

1-(2-Phosphono-4-bromophenyl)-3-(3-trifluoromethylphenyl)urea

Method A

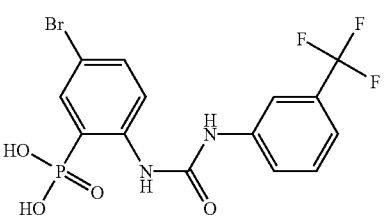

To a 40 mL vial containing a stirring bar, 1-(2-Diethylphosphono-4-bromophenyl)-3-(3-trifluoromethylphenyl)urea (1.2 g, 2.42 mmol) was added along with 15 mL of $CHCl_3$. This was cooled in an ice bath and then bromotrimethylsilane (5.0 g, 32.7 mmol) was added slowly under $N_2$ while stirring. The bath was removed after the addition and then the vial was sealed and heated at 40° C. for 2 days. The resulting solution was cooled in an ice bath and water was added dropwise (5 mL) followed by 10 mL of isopropanol. After 10 minutes the bath was removed and the reaction was stirred at room temperature for one day. The mixture was then diluted with 50 mL water and concentrated until a precipitate formed. The precipitate was filtered and then recrystallized from ethyl acetate to give 750 mg of 1-(2-Phosphono-4-bromophenyl)-3-(3-trifluoromethylphenyl) urea as a white solid. $^1$H-NMR (400 MHz, DMSO-D$_6$): δ=7.27 (d, 8.0 Hz, 1H, CHCHCCF$_3$), 7.43 (m, 1H, CHCHCCF$_3$), 7.60 (m, 2H, CHCBrCH), 7.70 (dd, 15 Hz, 2H$_2$, 1H, BsCCHCP) 7.90 (s, 1H, CHCF$_3$), 8.05 (m, 1H). $^{31}$P (400 Mz, CDCl$_3$) δ=13.41 (s).

EXAMPLE 62

Parallel Synthesis: 1-(2-phosphono-4-bromophenyl)-3-(3,5-bistrifluoromethylphenyl)urea disodium salt Method B

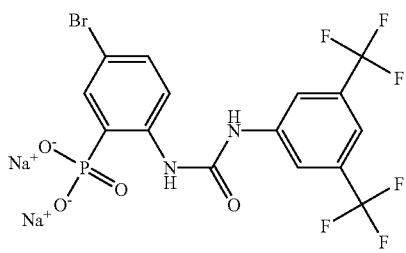

To a 30 mL vial containing a stirring bar DMSO-D$_6$ (0.5 mL), pyridine-D$_5$ (1 drop), 3-trifluoromethylphenylisocyanate (14 mg, 0.080 mol) and 2-Phosphono-4-bromoaniline disodium salt (10 mg, 0.036 mmol) were added. The resulting mixture was stirred at 65° C. for 3 hours, resulting in a DMSO solution of the desired urea.

EXAMPLE 63

N-(4-Bromo-2-iodo-phenyl)-4-trifluoromethoxy-benzamide

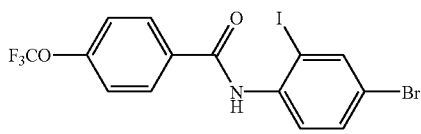

To a cooled 30 mL vial containing a stirring bar and 4-trifluoromethoxybenzoylchloride (0.70 g, 3.12 mmol), 2-iodo-4-bromoaniline (0.837 g, 2.81 mmol) in 3 mL of anhydrous pyridine was added. The bath was then removed. The reaction solution was stirred at room temperature overnight and 50 mL of EtOAc was added. The resulting solution was poured into 100 mL of 10% aq. HCl. The layers were stirred and then the organic layer was separated and washed with water (2×50 mL), dried with Na$_2$SO$_4$ and concentrated, revealing the desired product. $^1$H-NMR (400 MHz, CDCl$_3$): δ=7.37 (d, 8.4 Hz, 2HCF$_3$OCCH), 7.53 (m, 1H, ICNCCH), 7.96 (d, 1.6 Hz, 1H, BrCCHCl), 8.8 (d, 8.8 Hz, 2H, CHCCOCF$_3$), 8.21 (s, 1H, NH), 8.34 (d, 8.8 Hz, 1H, ICNCCHCH). MS (electrospray) 486 (MH$^+$), 488 (MH$^+$+2).

EXAMPLE 64

2-Diethylphosphono-4-bromo-(4-trifluoromethoxy-benzoyl)anilide

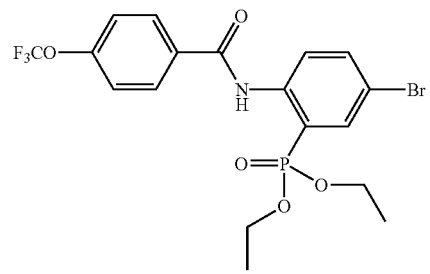

To a 30 mL vial, 2-iodo-4-bromo-(4-trifluoromethoxy-benzoyl)anilide (0.700 g, 1.56 mmol) was added along with triethylphosphite (0.776 g, 4.68 mmol) and PdCl$_2$ (14 mg, 0.078 mmol). The vial was flushed with N$_2$, sealed and then heated at 130° C. while stirring overnight. The resulting solution was cooled to room temperature and then purified by silica chromatography using a 1:1 mixture of EtOAc/hexane to give 0.45 g of the desired anilide as a white solid. $^1$H-NMR (400 MHz, CDCl$_3$): δ=1.36 (t, 6.8 Hz, 6H, CH$_3$), 4.15 (m, 4H, CH$_2$), 7.34 (d, 9.2 Hz, CF$_3$OCCH), 2H, 7.70 (m, 2H, CHCBRCH), 8.15 (d, 8.8 Hz, 2H, OCCCH), 8.78 (m, 1H, PCCNCH), 11.61 (s, 1H, NH). $^{31}$P (400 Mz, CDCl$_3$) δ=18.60 (s).

EXAMPLE 65

2-Diethylphosphono-4-bromo-(4-bromobenzoyl)anilide

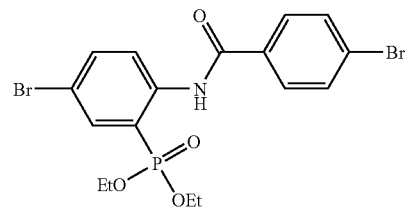

To a 30 mL vial containing a stirring bar, THF (1 mL) was added along with 5-methylbenzoxazoline-2-thione (10 mg, 0.033 mmol) and 4-bromobenzoyl chloride. The reaction mixture was stirred at room temperature for 0.5 hour and then 2-diethylphosphono-4-bromoaniline (10 mg, 0.033 mmol) was added. The resulting solution was heated at 50° C. overnight. Solvent was removed under a flow of N$_2$ and then 0.5 mL of DMSO-D$_6$ was added. Preparative TLC using silica plates and 2:1 hexane/Ethyl Acetate as the eluting solvent gave the desired anilide as a white solid. $^1$H-NMR (400 MHz, CDCl$_3$): δ=1.36 (t, 7.6 Hz, 6H CH$_3$), 4.10 (m, 4H, CH$_2$), 7.70 (m, 4H, ArH), 7.96 (m, 2H, ArH), 8.77 (m, 1H, CHNH), 11.60 (s, 1H, NH). $^{31}$P (400 Mz, CDCl$_3$) δ=18.57 (s).

EXAMPLE 66

Phosphate Transporter Inhibition In Vitro Testing

The following example outlines the procedures required for in vitro measurement of the inhibition of phosphate uptake by rabbit intestinal Brush Border Membrane Vesicles (BBMV).

Buffer Solution Preparation

| 300 MET | 50 mL |
|---|---|
| 300 mM mannitol | 2.73 g |
| 5 mM EGTA | 117 mg |
| 12 mM Tris base | 73 mg |
| pH 7.1 (w/HCl) | |
| 60 MET | 250 mL |
| 60 mM mannitol | 2.73 g |
| 5 mM EGTA | 585 mg |
| 12 mM Tris base | 363 mg |
| pH 7.1 (w/ HCl) | |
| Na Uptake buffer | 50 mL |
| 100 mM NaCl | 292 mg |
| 50 mM HEPES | 596 mg |
| 100 mM mannitol | 911 mg |
| 100 uM $KH_2PO_4$ | 50 mL 0.1 M stock |
| pH 7.4 (w/NaOH) | |
| STOP buffer | 1000 mL |
| 100 mM mannitol | 18.22 g |
| 20 mM HEPES:Tris | 20 mL total of 1 M stocks |
| 20 mM $MgSO_4$ | 4.93 g |
| 100 mM choline Cl | 13.96 g |
| 5 mM $KH_2PO_4$ | 681 mg |
| 280 MH | 250 mL |
| 280 mM mannitol | 12.75 g |
| 20 mM HEPES | 5 mL of 1 M stock |
| pH 7.4 (w/KOH) | |
| K Uptake buffer | 50 mL |
| 100 mM KCl | 373 mg |
| 50 mM HEPES | 596 mg |
| 100 mM mannitol | 911 mg |
| 100 mM $KH_2PO_4$ | 50 mL 0.1 M stock |
| PH 7.4 (w/KOH) | |

BBMV Isolation

Rabbit Intestinal Brush Border Membrane Vesicles (BBMV) were isolated from mucosal scrapings of the upper small intestine (duodenum) of male New Zealand White rabbits. The scrapings were divided into 2 g aliquots in cryopreservation vials, frozen in liquid nitrogen, and stored at −80° C.

The following procedure was performed for each 2 g sample of BBMV mucosal scraping. Buffer volumes and container sizes were adjusted appropriately for the number of 2 g samples used. The entire preparation was performed on ice, unless otherwise stated.

Mucosal scrapings (2 g per tube) were thawed in a 37° C. water bath for 3 minutes and then placed on ice. The scrapings were suspended with a total of 7.5 ml of 300 MET, and transferred to a 250 mL Coming tube on ice. To the suspension was added 30 mL cold (4° C.) deionized water ($dH_2O$). The suspension was homogenized with a tissue homogenizer (Polytron) on high speed for 2 minutes. A stir bar and $MgCl_2$ (81.3 mg) was added. The suspension was mixed well by inverting the closed tube. The suspension was stirred on ice, ensuring that a good vortex is achieved with the stir bar, for 40 minutes. The suspension was transferred to a chilled centrifuge tube and spun at 4000×g for 15 minutes. The supernatant was transferred to a new chilled centrifuge tube and spun at 32000×g for 30 minutes. The supernatant was discarded and the pellet was re-suspended with 34 mL cold 60 MET. The suspension was homogenized with a Dounce homogenizer with 8 strokes. The suspension was transferred to a fresh 250 mL Coming tube. A stir bar and 69.1 mg $MgCl_2$ were added. The suspension was stirred well on ice for 10 minutes. The suspension was transferred to a chilled centrifuge tube and spun at 4000×g for 15 minutes. The supernatant was transferred to a new chilled centrifuge tube and spun at 32000×g for 30 minutes. The supernatant was discarded. At this stage, the preparation could be continued or this pellet (P4) could be frozen in liquid nitrogen and stored at −80° C. When needed, this pellet could be allowed to thaw at room temperature for 5 minutes. Continuing the preparation, the pellet was re-suspended with 34 mL cold 280 MH. The suspension was homogenized in a Dounce homogenize with 8 strokes. The suspension was transferred to a new chilled centrifuge tube and spun at 32000×g for 30 minutes. The supernatant was discarded. To the pellet was added 500 µL 280 MH and the pellet was re-suspended very carefully with a 1 mL tuberculin syringe with a 25-gauge needle with care not to create bubbles. Once the entire pellet was suspended, the suspension was transferred to a chilled 1.5 mL microfuge tube. The suspension was evenly dispersed by bringing the suspension up into the syringe through the 25-gauge needle, and back out again 8 times with care not to create bubbles. The total protein concentration was determined by performing a Bradford Protein Assay. Using that value, the BBMV were diluted with 280 MH to reach approximately 0.5–2.0 mg/mL. The solution was used as soon as possible for uptake studies.

High Throughput Screening (HTS)

$^{33}PO_4$ Uptake in Rabbit Intestinal BBMV

The following experiment was performed using a Beckman Multimek 96-tip robotic pipettor. The following outlines the preparation required to screen one 96-well plate of compounds. However, multiple plates could be screened in one experiment.

To the "Uptake Buffers" was added $^{33}PO_4$ to reach 200,000 CPM/19 µL. The buffer solutions were stored at room temperature. The following control solutions were prepared and placed into appropriate wells of a polypropylene, 96-well V-bottom plate ("Hot Stock Plate"):

a. Maximum activity (MAX)–Na Uptake buffer+$^{33}PO_4$ at 200,000 CPM/19 µL
   b. Midline activity (MID)–MAX+100 µM $KH_2PO_4$, pH 7.4
   c. Minimum activity (MIN)–K Uptake buffer+$^{33}PO_4$ at 200,000 CPM/19 µL In the remaining wells, used for compound containing reactions, are placed MAX Control Buffer. The Hot Stock Plate was stored at room temperature. To each well of an appropriate 96-well filter plate was added approximately 200 µL Stop Buffer to pre-wet the filters for at least 15 minutes prior to assay. The "Compound Plate" was set-up by loading appropriate wells of a 96-well, polypropylene, V-bottom plate with compound solutions. This could be for testing inhibition at a single "screening" concentration, or to measure the potency of compounds by dose-response analysis at the appropriate concentrations. A "BBMV Plate" was set up by loading a 96-well, polypropylene, V-bottom plate with BBMVs at 0.5–2.0 mg/mL (prepared as described above). The BBMV Plate was kept on ice until just prior to the assay. The reaction was initiated by aspiration of the hot uptake buffers (19 μL), from the Hot Stock Plate, and the compound solutions (2 μL), from the Compound Plate, dispensing into an empty 96-well V-bottom plate (Assay Plate), then immediately aspirating the BBMVs (19 μL), from the BBMV Plate and dispensing into the same Assay Plate. The addition of the BBMVs to the assay plate marked the reaction start time. After 15 minutes, the reaction was quenched by addition of 200 μL of STOP buffer from a reservoir. The Stop Buffer was aspirated by vacuum from the wells, through the filters, of the pre-soaked filter plate using a filter plate manifold. The quenched reactions were aspirated and transferred to the filter plate under vacuum. The filters were washed 2 times with 200 μL STOP buffer under vacuum. The filter plate was removed, dried, and the bottom of the filter plate was sealed. To each well of the filter plate was added 50 μL of scintillant (Microscint-20). A top seal was then applied to the filter plate. The plate was incubated for approximately 20 minutes before reading for $^{33}$P CPM on a scintillation counter (i.e., TopCount—Packard Instruments). Percent inhibition was calculated by comparing the CPM values from compound containing wells to the MAX and MIN controls on the same plate using the following formula.

1−((CPM−MIN)/(MAX−MIN))

IC$_{50}$ values were calculated from non-linear regression analysis within an appropriate software package (i.e., Prism GraphPad).

The results using compounds of the present invention are shown in Tables 1–13. As can be seen, these compounds inhibit phosphate transport in brush border membrane vesicles.

TABLE 1

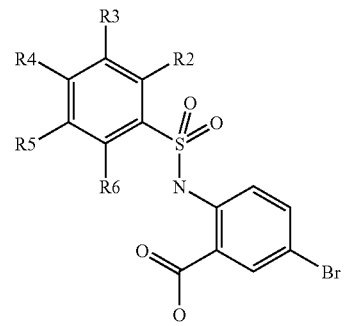

| Compound | R2 | R3 | R4 | R5 | R6 | IC$_{50}$ |
|---|---|---|---|---|---|---|
| 1 | H | H | C6H5 | H | H | a |
| 2 | H | H | CF3O | H | H | a |
| 3 | H | CF3 | H | CF3 | H | b |
| 4 | H | Cl | Cl | H | Cl | b |
| 5 | H | H | NO2 | H | H | b |
| 6 | CH3 | H | CH3 | H | CH3 | b |
| 7 | H | H | CF3 | H | H | b |
| 8 | H | H | C6H5 | H | H | b |
| 9 | H | NO2 | CH3 | H | H | b |
| 10 | H | Cl | H | H | H | c |
| 11 | H | H | C6H5O | H | H | c |

TABLE 1-continued

| Compound | R2 | R3 | R4 | R5 | R6 | IC$_{50}$ |
|---|---|---|---|---|---|---|
| 12 | H | H | Cl | NO2 | H | c |
| 13 | H | H | H | NO2 | H | c |
| 14 | H | H | CF3O | H | H | c |
| 15 | H | H | Cl | NO2 | H | c |
| 16 | H | CF3 | H | H | H | c |
| 17 | —C4H4— | | H | H | H | c |
| 18 | H | H | Br | H | H | c |
| 19 | H | H | H | —C4H4— | | c |
| 20 | H | H | CH3 | NO2 | H | c |
| 21 | H | H | H | CF3 | H | c |
| 22 | H | H | H | Cl | H | c |
| 23 | H | H | C2H3 | H | H | c |
| 24 | H | H | I | H | H | c |
| 25 | F | H | H | H | H | c |
| 26 | H | H | H | H | CF3 | c |
| 27 | H | H | Cl | H | H | c |
| 28 | H | H | C5H11 | H | H | c |
| 29 | H | H | Cl | H | H | c |
| 30 | H | H | C2H3 | H | H | c |
| 31 | H | H | H | H | Cl | c |
| 32 | H | H | H | NO2 | H | c |
| 33 | H | H | NO2 | H | H | c |
| 34 | H | H | H | F | H | c |
| 35 | CH3O | H | H | CH3O | H | c |
| 36 | C3H3N2 | H | H | H | H | d |
| 37 | H | H | CH3O | H | H | d |
| 38 | NO2 | H | H | H | H | e |
| 39 | H | H | Cl | H | H | f |
| 40 | H | H | Cl | NO2 | H | f |
| 41 | H | H | CF3O | H | H | f |
| 42 | H | H | CH3O | NO2 | H | f |
| 43 | H | H | Cl | H | H | f |
| 44 | H | NO2 | HO | H | H | f |
| 45 | H | H | CH3O | NO2 | H | f |
| 46 | H | H | Cl | H | H | f |
| 47 | H | H | CHO2 | H | H | f |
| 48 | H | H | H | H | NO2 | f |
| 49 | H | H | CH4N | H | H | f | a = 0–50 μM
b = 51–100 μM
c = 101–500 μM
d = 501–1000 μM
e = 1000–1500 μM
f = >1500 μM

TABLE 2

| Compound | R2 | R3 | R4 | R5 | R6 | R7 | IC$_{50}$ |
|---|---|---|---|---|---|---|---|
| 50 | H | H | CF3O | H | H | X$_7$-(2-Cl-phenyl) | a |
| 51 | H | H | CF3O | H | H | X$_7$-(4-Br-phenyl) | a |
| 52 | H | H | CF3O | H | H | X$_7$-CH$_2$-(4-F-phenyl) | a |
| 53 | H | H | CF3O | H | H | X$_7$-CH$_2$-(4-Cl-phenyl) | a |
| 54 | H | H | CF3O | H | H | X$_7$-CH$_2$-(3-OCH$_3$-phenyl) | a |
| 55 | H | H | CF3O | H | H | X$_7$-CH$_2$-(2-CF$_3$-phenyl) | a |
| 56 | H | H | CF3O | H | H | X$_7$-(4-OCH$_3$-phenyl) | b |
| 57 | H | H | CF3O | H | H | X$_7$-(4-CH$_3$-phenyl) | b |
| 58 | H | H | CF3O | H | H | X$_7$-CH$_2$-(3-CH$_3$-phenyl) | b |

TABLE 2-continued

| Compound | R2 | R3 | R4 | R5 | R6 | R7 | IC$_{50}$ |
|---|---|---|---|---|---|---|---|
| 59 | H | H | CF3O | H | H | X$_7$-(3,4-dichlorophenyl) | b |
| 60 | H | H | CF3O | H | H | X$_7$-CH$_2$-(4-OCF$_3$-phenyl) | b |
| 61 | H | H | CF3O | H | H | X$_7$-CH$_2$-(2-OCF$_3$-phenyl) | b |
| 62 | H | H | CF3O | H | H | X$_7$-(2-bromophenyl) | b |
| 63 | H | H | CF3O | H | H | X$_7$-CH$_2$-(3,4-dichlorophenyl) | b |
| 64 | H | H | CF3O | H | H | X$_7$-CH$_2$-(2,4-difluorophenyl) | b |
| 65 | H | H | CF3O | H | H | X$_7$-(4-SCH$_3$-phenyl) | b |
| 66 | H | H | CF3O | H | H | X$_7$-CH$_2$-(2,5-difluorophenyl) | b |

TABLE 2-continued
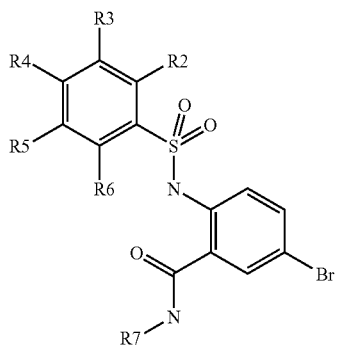
| Compound | R2 | R3 | R4 | R5 | R6 | R7 | IC$_{50}$ |
|---|---|---|---|---|---|---|---|
| 67 | H | H | CF3O | H | H | X$_7$—CH$_2$—(2-methylphenyl) | b |
| 68 | H | H | CF3O | H | H | X$_7$—(2-(1-pyrrolyl)phenyl) | c |
| 69 | H | H | CF3O | H | H | X$_7$—CH$_2$—(3,5-bis(trifluoromethyl)phenyl) | c |
| 70 | H | H | CF3O | H | H | X$_7$—CH$_2$—(2-fluorophenyl) | c |
| 71 | H | H | CF3O | H | H | X$_7$—(4-tert-butylphenyl) | c |
| 72 | H | H | CF3O | H | H | X$_7$—(3-bromophenyl) | c |
| 73 | H | H | CF3O | H | H | X$_7$—(4-biphenyl) | c |

TABLE 2-continued
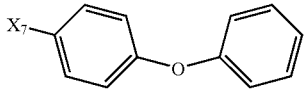
| Compound | R2 | R3 | R4 | R5 | R6 | R7 | IC$_{50}$ |
|---|---|---|---|---|---|---|---|
| 74 | H | H | CF3O | H | H | 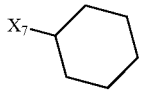 | c |
| 75 | H | H | CF3O | H | H | 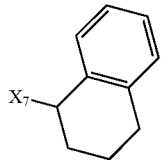 | c |
| 76 | H | H | CF3O | H | H | 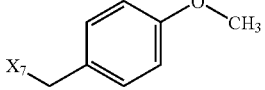 | c |
| 77 | H | H | CF3O | H | H | 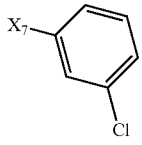 | c |
| 78 | H | H | CF3O | H | H | 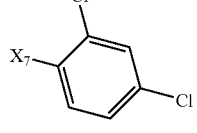 | c |
| 79 | H | H | CF3O | H | H | 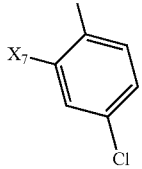 | c |
| 80 | H | H | CF3O | H | H | | d |
| 81 | H | H | CF3O | H | H | 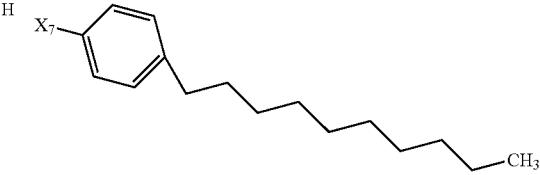 | d |

TABLE 2-continued
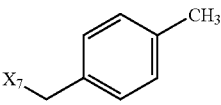
| Compound | R2 | R3 | R4 | R5 | R6 | R7 | IC$_{50}$ |
|---|---|---|---|---|---|---|---|
| 82 | H | H | CF3O | H | H | 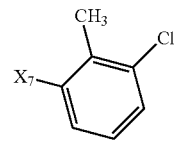 | d |
| 83 | H | H | CF3O | H | H | 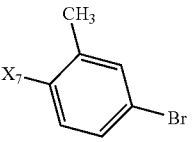 | d |
| 84 | H | H | CF3O | H | H | 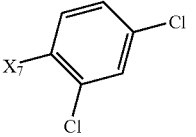 | e |
| 85 | H | H | Cl | H | H | 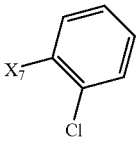 | b |
| 86 | H | H | Cl | H | H | 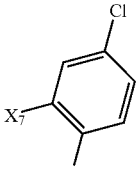 | b |
| 87 | H | H | Cl | H | H | 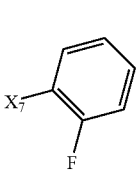 | b |
| 88 | H | H | Cl | H | H | | c |

TABLE 2-continued
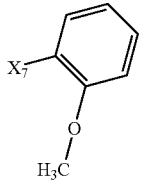
| Compound | R2 | R3 | R4 | R5 | R6 | R7 | IC$_{50}$ |
|---|---|---|---|---|---|---|---|
| 89 | H | H | Cl | H | H | 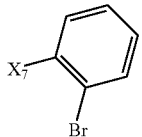 | c |
| 90 | H | H | Cl | H | H | 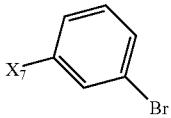 | c |
| 91 | H | H | Cl | H | H | 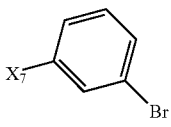 | f |
| 92 | H | H | Cl | H | H | 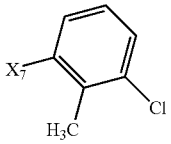 | f |
| 93 | H | H | Cl | H | H | 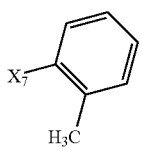 | f |
| 94 | H | H | Cl | H | H | 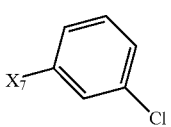 | f |
| 95 | H | H | Cl | H | H |  | f |

TABLE 2-continued

| Compound | R2 | R3 | R4 | R5 | R6 | R7 | IC$_{50}$ |
|---|---|---|---|---|---|---|---|
| 96 | H | H | Cl | H | H | 2-Cl, 5-X$_7$ benzoyl-(4-Cl-phenyl) | f |
| 97 | H | H | Cl | H | H | 4-Cl-phenyl-X$_7$ | f |
| 98 | H | NO2 | CH3O | H | H | 2,5-diCl-phenyl-X$_7$ | b |
| 99 | H | NO2 | CH3O | H | H | 2-Cl-phenyl-X$_7$ | b |
| 100 | H | NO2 | CH3O | H | H | 3-Cl-2-CH$_3$-phenyl-X$_7$ | b |
| 101 | H | NO2 | CH3O | H | H | 3-Cl-phenyl-X$_7$ | b |
| 102 | H | NO2 | CH3O | H | H | 2-F-phenyl-X$_7$ | b |

TABLE 2-continued
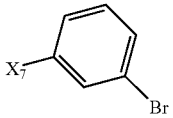
| Compound | R2 | R3 | R4 | R5 | R6 | R7 | IC$_{50}$ |
|---|---|---|---|---|---|---|---|
| 103 | H | NO2 | CH3O | H | H | 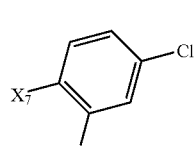 | b |
| 104 | H | NO2 | CH3O | H | H | 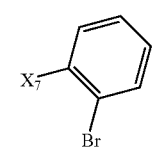 | b |
| 105 | H | NO2 | CH3O | H | H | 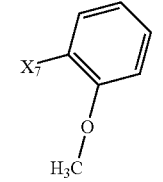 | b |
| 106 | H | NO2 | CH3O | H | H | 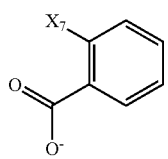 | c |
| 107 | H | NO2 | CH3O | H | H | 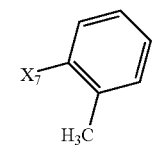 | c |
| 108 | H | NO2 | CH3O | H | H | 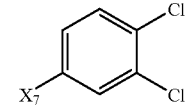 | c |
| 110 | H | NO2 | Cl | H | H |  | a |

TABLE 2-continued

| Compound | R2 | R3 | R4 | R5 | R6 | R7 | IC$_{50}$ |
|---|---|---|---|---|---|---|---|
| 111 | H | NO2 | Cl | H | H | 2,5-dichlorophenyl (X$_7$) | a |
| 112 | H | NO2 | Cl | H | H | 2,5-dichlorophenyl (X$_7$) | a |
| 113 | H | NO2 | Cl | H | H | 3,4-dichlorophenyl (X$_7$) | b |
| 114 | H | NO2 | Cl | H | H | 2-bromophenyl (X$_7$) | b |
| 115 | H | NO2 | Cl | H | H | 2,5-dichlorophenyl (X$_7$) | b |
| 116 | H | NO2 | Cl | H | H | 3-bromophenyl (X$_7$) | c |
| 117 | H | NO2 | Cl | H | H | 2-methoxyphenyl (X$_7$) | c |

TABLE 2-continued
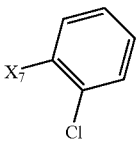
| Compound | R2 | R3 | R4 | R5 | R6 | R7 | IC$_{50}$ |
|---|---|---|---|---|---|---|---|
| 118 | H | NO2 | Cl | H | H | 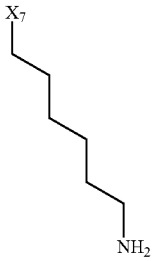 | c |
| 119 | H | NO2 | Cl | H | H | 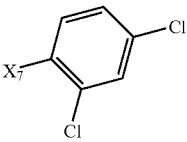 | e |
| 120 | H | NO2 | Cl | H | H | 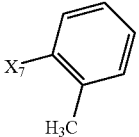 | f |
| 121 | H | NO2 | Cl | H | H | 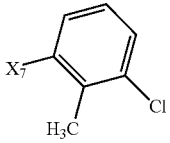 | f |
| 122 | H | NO2 | Cl | H | H | 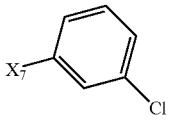 | f |
| 123 | H | NO2 | Cl | H | H | 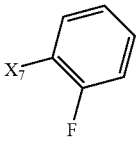 | f |
| 124 | H | NO2 | Cl | H | H |  | f |

TABLE 2-continued

[Structure: substituted benzenesulfonamide with R2, R3, R4, R5, R6 on sulfonyl-bearing ring; N-linked to bromo-substituted benzamide bearing NHR7]

| Compound | R2 | R3 | R4 | R5 | R6 | R7 | IC$_{50}$ |
|---|---|---|---|---|---|---|---|
| 125 | H | NO2 | H | H | H | X7—(3,4-dichlorophenyl) | c | a = 0–50 μM
b = 51–100 μM
c = 101–500 μM
d = 501–1000 μM
e = 1001–1500 μM
f = >1500 μM

TABLE 3

| Compound | Structure | % Inhib. At 100 μM |
|---|---|---|
| 126 | 4-(trifluoromethoxy)-N-(2-fluoro-4-iodophenyl)benzenesulfonamide | 103 |
| 127 | 3,5-bis(trifluoromethyl)-N-(2,4,5-trichlorophenyl)benzenesulfonamide | 101 |
| 128 | 4-(trifluoromethoxy)-N-(4-(methylthio)phenyl)benzenesulfonamide | 88 |

TABLE 3-continued

| Compound | Structure | % Inhib. At 100 μM |
|----------|-----------|--------------------:|
| 129 | 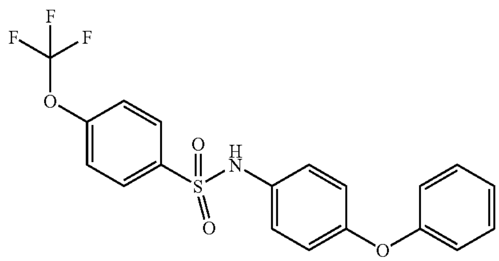 | 84 |
| 130 | 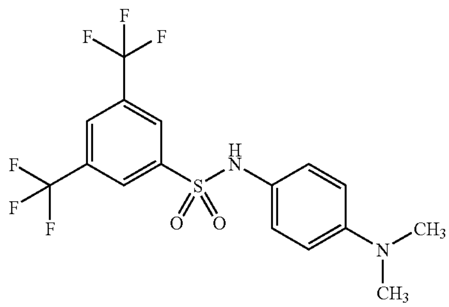 | 81 |
| 131 | 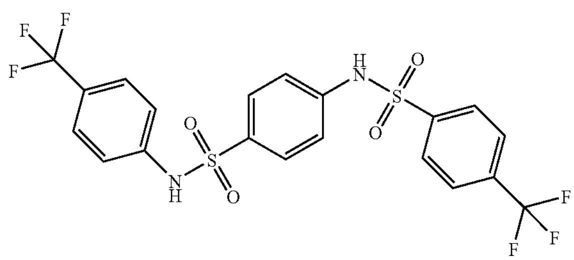 | 80 |
| 132 | 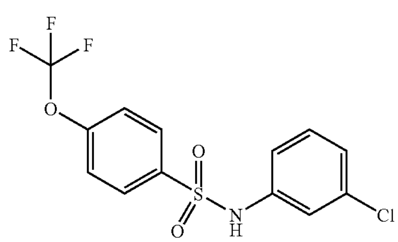 | 79 |
| 133 | 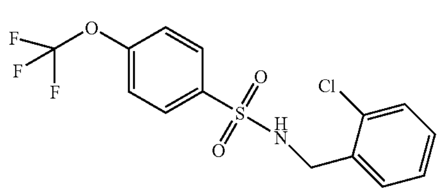 | 77 |
| 134 | 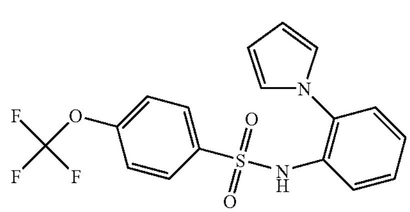 | 76 |

TABLE 3-continued
| Compound | Structure | % Inhib. At 100 μM |
|---|---|---|
| 135 | 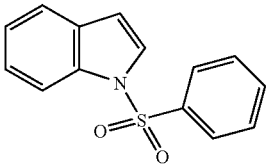 | 76 |
| 136 | 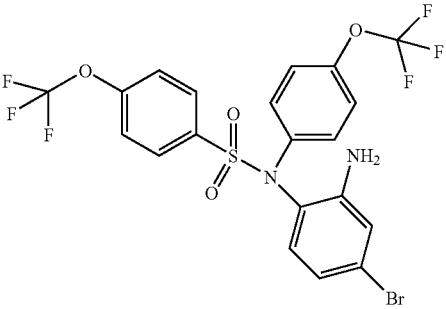 | 76 |
| 137 | 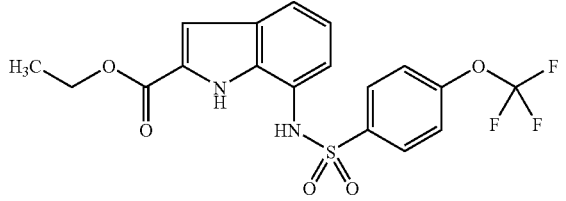 | 74 |
| 138 | 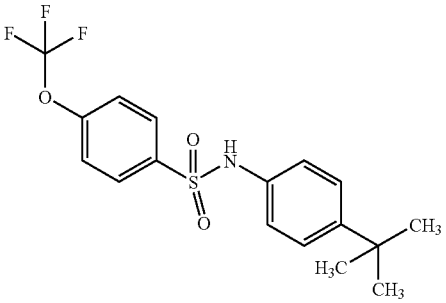 | 71 |
| 139 | 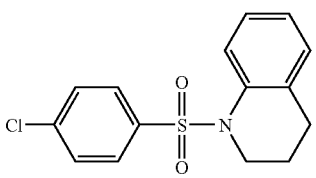 | 70 |
| 140 | 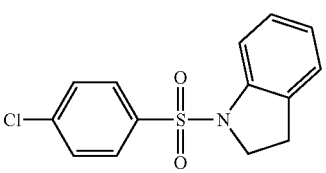 | 69 |

TABLE 3-continued

| Compound | Structure | % Inhib. At 100 µM |
|---|---|---|
| 141 | 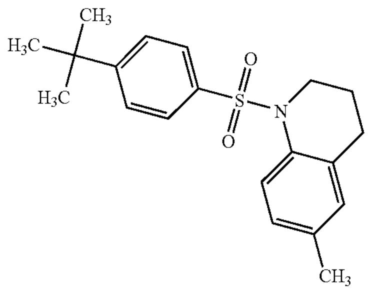 | 68 |
| 142 | 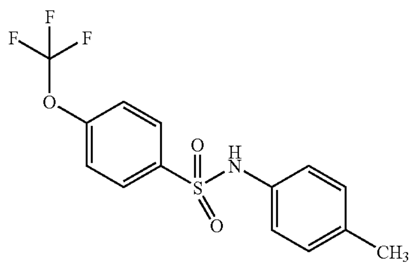 | 67 |
| 143 | 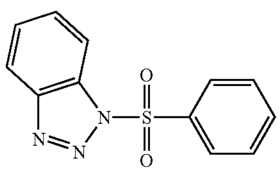 | 64 |
| 144 | 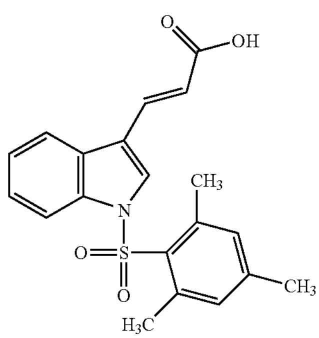 | 64 |
| 145 | 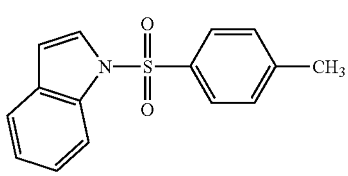 | 62 |
| 146 | 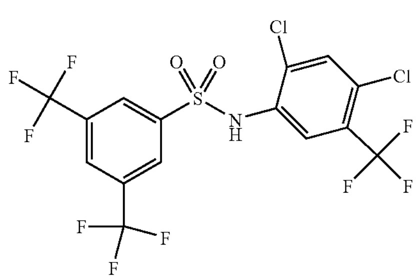 | 62 |

TABLE 3-continued

| Compound | Structure | % Inhib. At 100 μM |
|---|---|---|
| 147 | 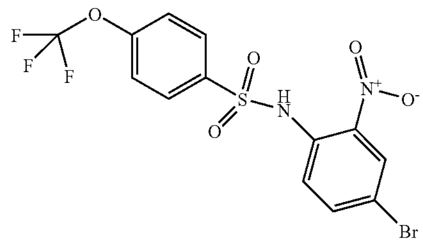 | 61 |
| 148 | 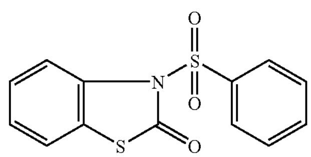 | 60 |
| 149 | 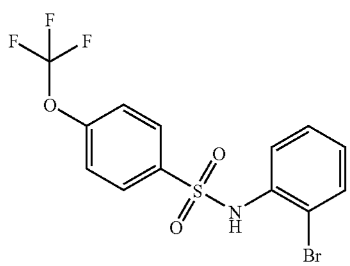 | 57 |
| 150 | 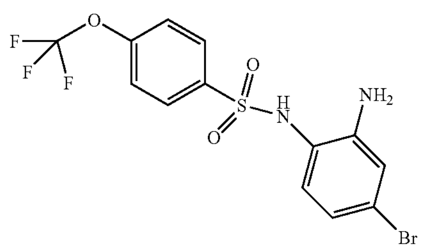 | 57 |
| 151 | 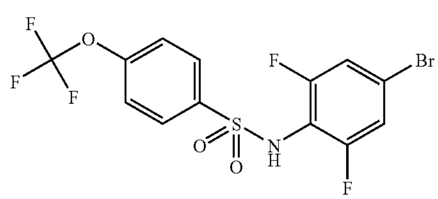 | 54 |
| 152 | 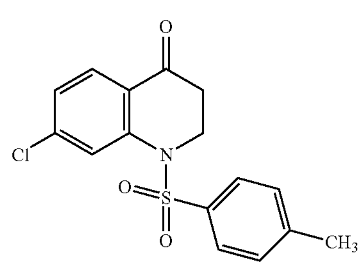 | 54 |

TABLE 3-continued

| Compound | Structure | % Inhib. At 100 μM |
|---|---|---|
| 153 | 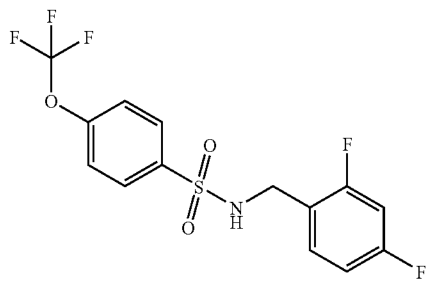 | 53 |
| 154 | 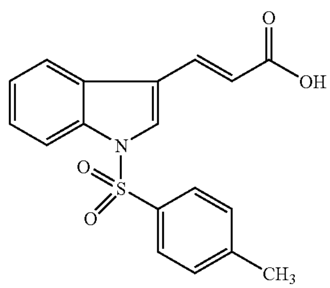 | 52 |
| 155 | 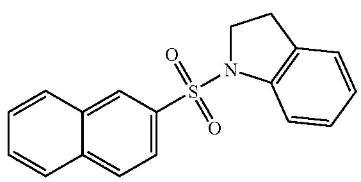 | 51 |
| 156 | 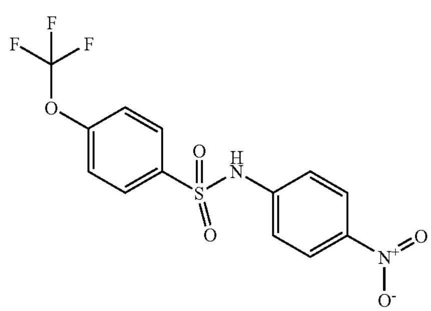 | 46 |
| 157 | 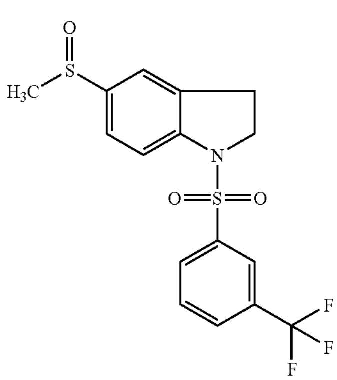 | 37 |

TABLE 3-continued

| Compound | Structure | % Inhib. At 100 μM |
|---|---|---|
| 158 | 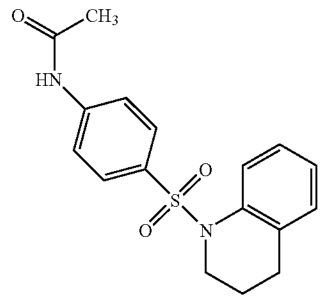 | 37 |
| 159 | 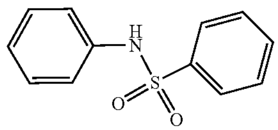 | 36 |
| 160 | 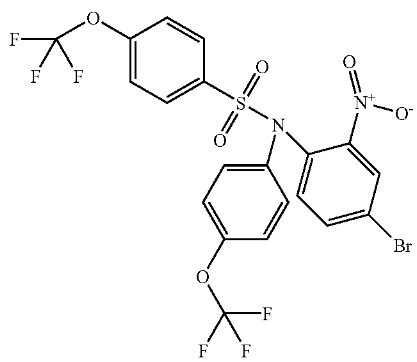 | 34 |
| 161 | 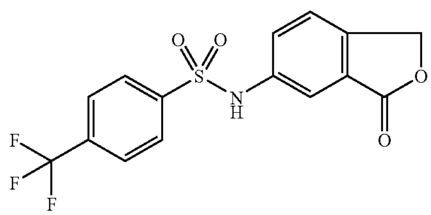 | 29 |
| 162 | 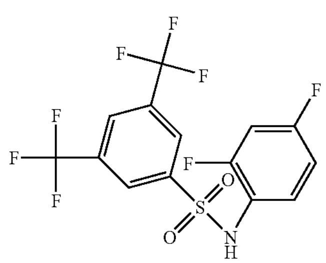 | 29 |
| 163 | 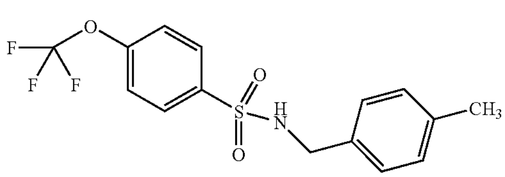 | 26 |

TABLE 3-continued

| Compound | Structure | % Inhib. At 100 μM |
|---|---|---|
| 164 | 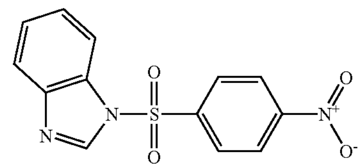 | 26 |
| 165 | 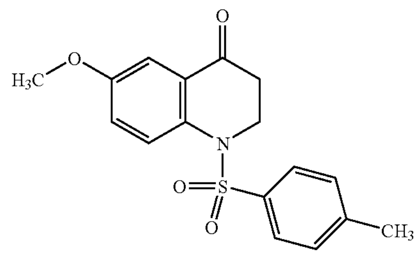 | 25 |
| 166 | 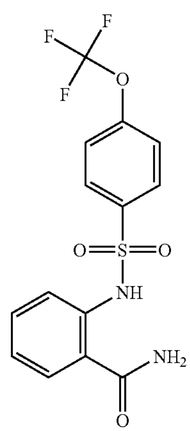 | 22 |
| 167 | 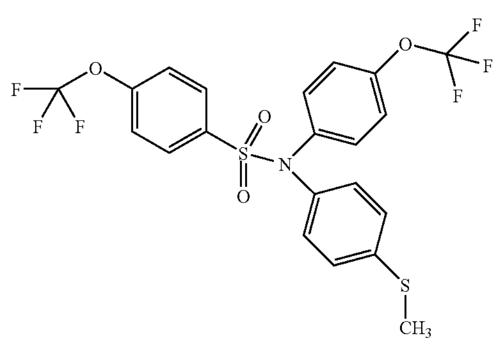 | 21 |
| 168 | 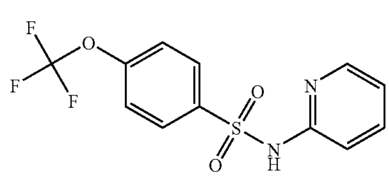 | 16 |

TABLE 3-continued

| Compound | Structure | % Inhib. At 100 μM |
|---|---|---|
| 169 | 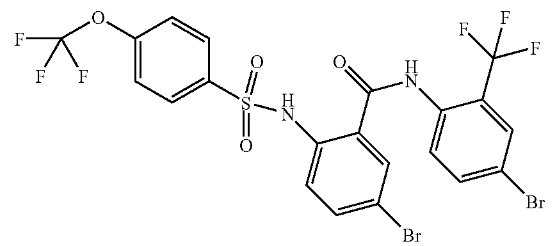 | 106 |
| 170 | 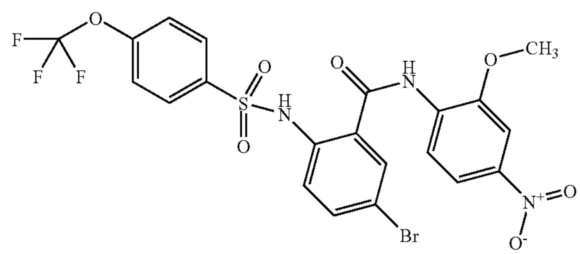 | 103 |
| 171 | 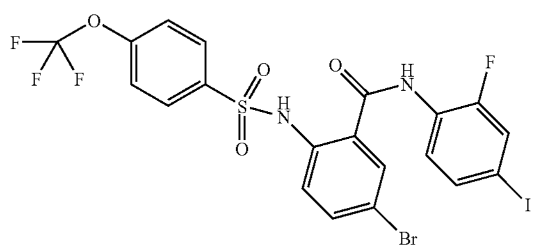 | 100 |
| 172 | 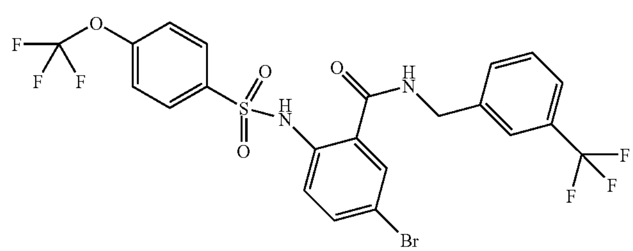 | 96 |
| 173 | 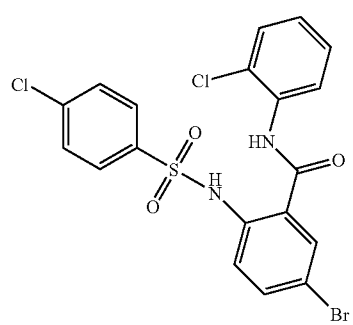 | 95 |
| 174 | 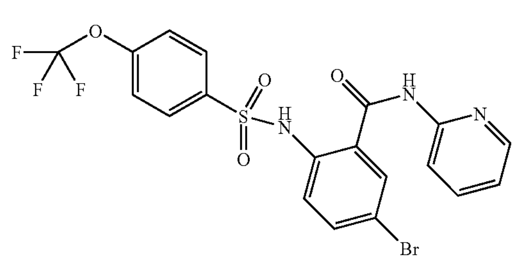 | 84 |

TABLE 3-continued
| Compound | Structure | % Inhib. At 100 μM |
|---|---|---|
| 175 | 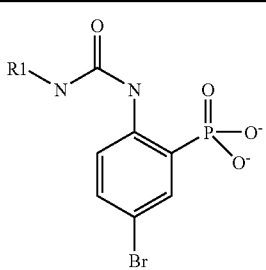 | 78 |
| 176 | 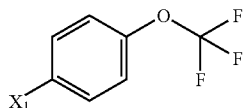 | 36 |
TABLE 4
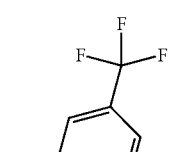
| Compound | R1 | IC$_{50}$ |
|---|---|---|
| 177 | 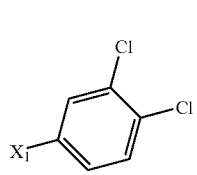 | a |
| 178 | 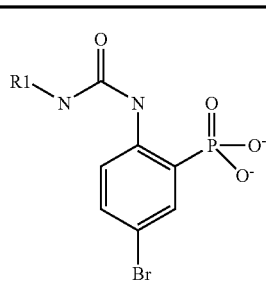 | a |
| 179 | 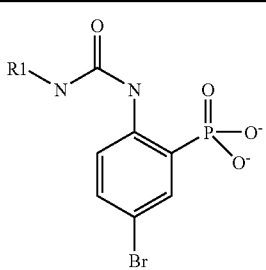 | a |
TABLE 4-continued
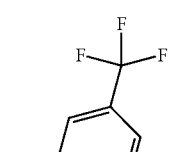
| Compound | R1 | IC$_{50}$ |
|---|---|---|
| 180 | 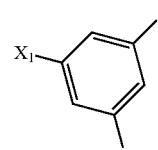 | b |
| 181 | 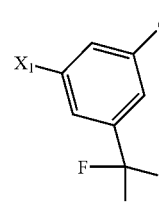 | b |

TABLE 4-continued
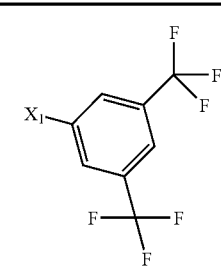
| Compound | R1 | IC$_{50}$ |
|---|---|---|
| 182 | 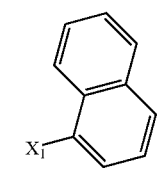 | b |
| 183 | 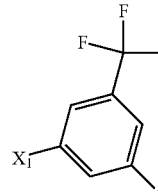 | b |
| 184 | 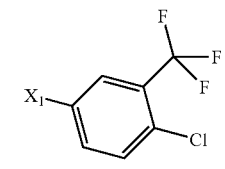 | c |
| 185 | 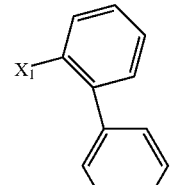 | c |
| 186 | 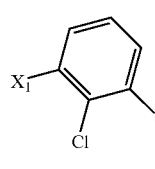 | c |
| 187 | 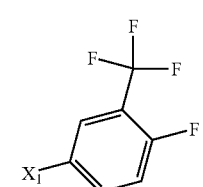 | c |
TABLE 4-continued
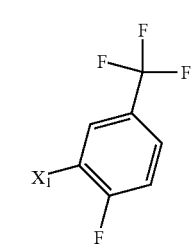
| Compound | R1 | IC$_{50}$ |
|---|---|---|
| 188 | 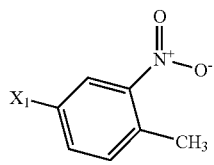 | c |
| 189 | 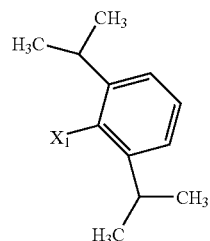 | c |
| 190 | 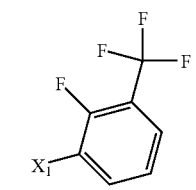 | c |
| 191 | 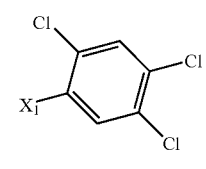 | c |
| 192 | | c |
| 193 | | c |

TABLE 4-continued

[Structure: R1-NH-C(=O)-N(H)- attached to benzene ring with P(=O)(O⁻)(O⁻) ortho and Br para]

| Compound | R1 | IC$_{50}$ |
|---|---|---|
| 194 | 4-fluoro-3-nitrophenyl (X$_1$ attached) | c |
| 195 | 3-chlorophenyl (X$_1$) | d |
| 196 | 2,6-dimethylphenyl (X$_1$) | d |
| 197 | 3-cyanophenyl (X$_1$) | d |
| 198 | 2-chloro-3-(trifluoromethyl)phenyl (X$_1$) | d |
| 199 | 3-acetylphenyl (X$_1$) | d |
| 200 | 2-fluorophenyl (X$_1$) | d |

TABLE 4-continued

[Structure: R1-NH-C(=O)-N(H)- attached to benzene ring with P(=O)(O⁻)(O⁻) ortho and Br para]

| Compound | R1 | IC$_{50}$ |
|---|---|---|
| 201 | benzyl (X$_1$-CH$_2$-phenyl) | d |
| 202 | 4-(trifluoromethyl)phenyl (X$_1$) | d |
| 203 | 3-methoxyphenyl (X$_1$) | d |
| 204 | 2,6-difluorophenyl (X$_1$) | e |
| 205 | phenyl (X$_1$) | e |
| 206 | 3,5-dimethylphenyl (X$_1$) | e |
| 207 | 4-methylphenyl (X$_1$) | e |
| 208 | 3-(ethoxycarbonyl)phenyl (X$_1$) | e |

TABLE 4-continued

| Compound | R1 | IC$_{50}$ |
|---|---|---|
| 209 | 1-(naphthalen-1-yl)ethyl (CH$_3$ on CH attached to X$_1$) | f |
| 210 | 4-isopropylphenyl-X$_1$ | f |
| 211 | 3-bromophenyl-X$_1$ | f |
| 212 | 4-ethoxyphenyl-X$_1$ | f |
| 213 | 4-chlorophenyl-X$_1$ | f | a = 0–50 μM
b = 51–100 μM
c = 101–500 μM
d = 501–1000 μM
e = 1001–1500 μM
f = >1500 μM

TABLE 5

| Compound | Structure | % Inhib. at 100 μM |
|---|---|---|
| 214 | 1,3-bis(3-(trifluoromethyl)phenyl)urea | 100 |
| 215 | 1-(2,3-dichlorophenyl)-3-(3-(trifluoromethyl)phenyl)urea | 96 |
| 216 | 1-(3,4-dichlorophenyl)-3-(3-(trifluoromethyl)phenyl)urea | 95 |

TABLE 5-continued

| Compound | Structure | % Inhib. at 100 μM |
|---|---|---|
| 217 | 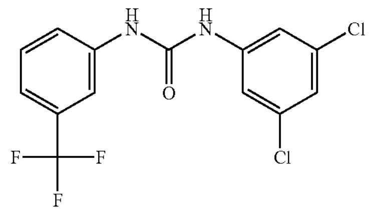 | 95 |
| 218 | 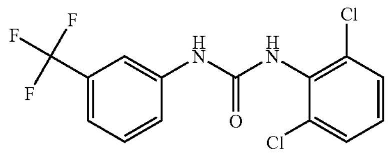 | 93 |
| 219 | 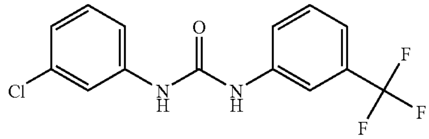 | 92 |
| 220 | 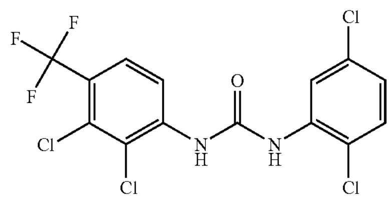 | 92 |
| 221 | 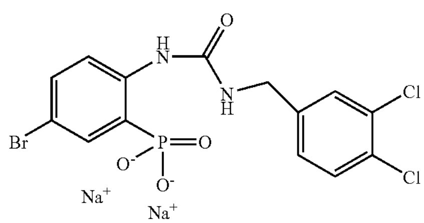 | 91 |
| 222 | 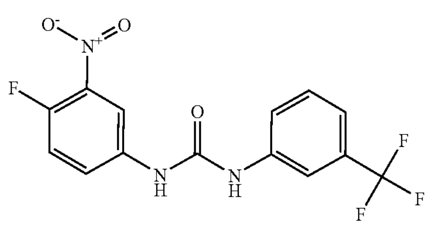 | 88 |
| 223 | 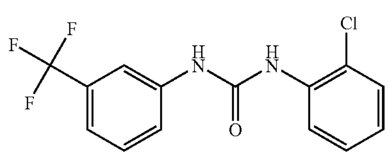 | 85 |
| 224 | 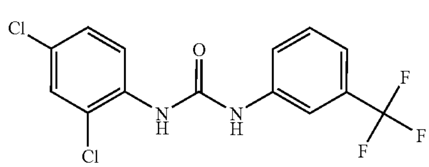 | 85 |

TABLE 5-continued

| Compound | Structure | % Inhib. at 100 μM |
|---|---|---|
| 225 | 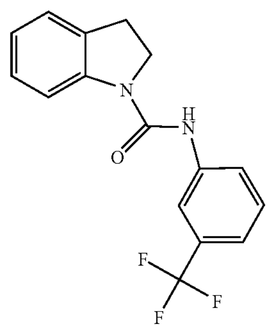 | 80 |
| 226 | 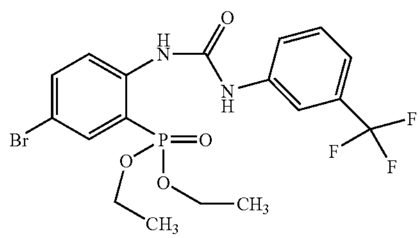 | 77 |
| 227 | 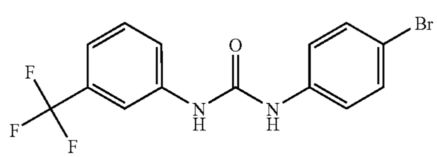 | 75 |
| 228 | 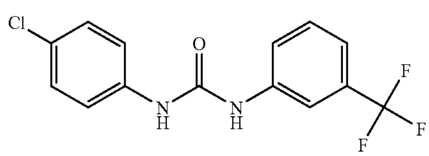 | 74 |
| 229 | 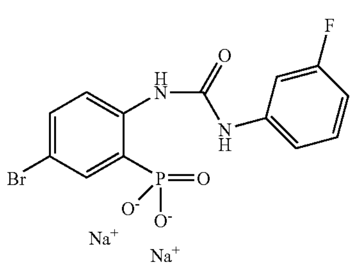 | 73 |
| 230 | 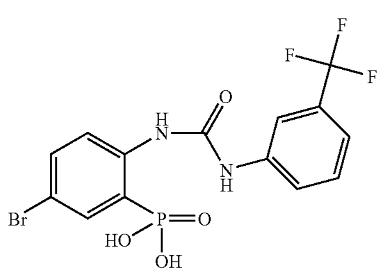 | 49 |

TABLE 6

| Compound | Structure | % Inhib. at 100 μM |
|---|---|---|
| 231 | 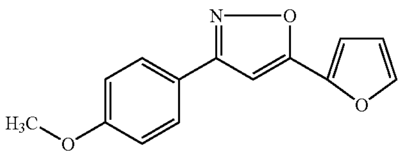 | 74 |
| 232 | 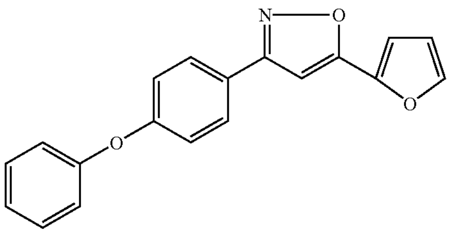 | 72 |
| 233 | 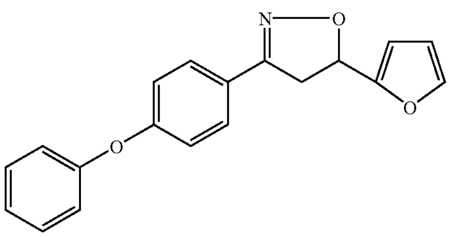 | 68 |
| 234 | 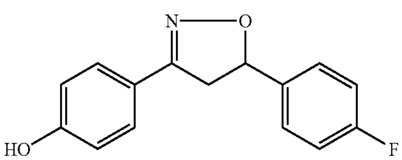 | 62 |
| 235 | 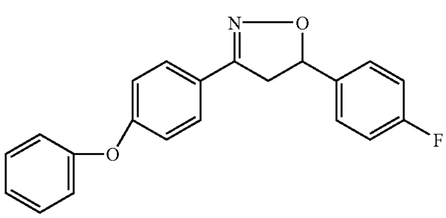 | 54 |
| 236 | 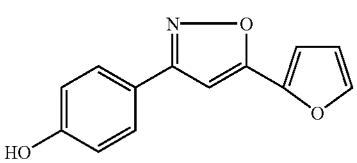 | 41 |
| 237 | 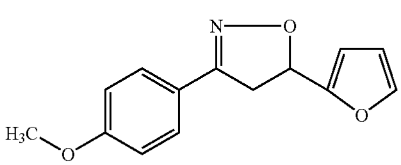 | 40 |

TABLE 6-continued

| Compound | Structure | % Inhib. at 100 μM |
|---|---|---|
| 238 | 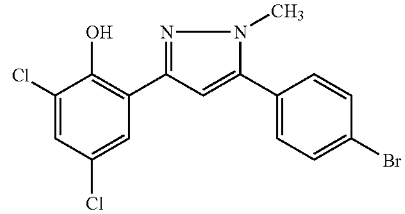 | 16 |

TABLE 7

| Compound | Structure | IC$_{50}$ |
|---|---|---|
| 239 | 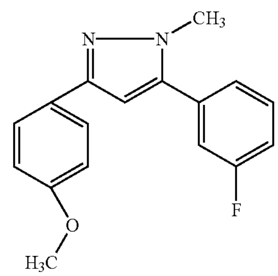 | c |
| 240 | 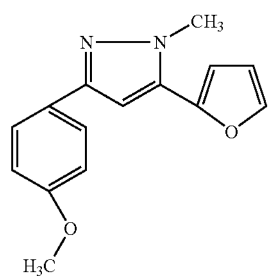 | c |
| 241 | 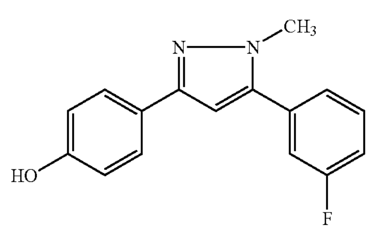 | c |

TABLE 7-continued

| Compound | Structure | IC$_{50}$ |
|---|---|---|
| 242 | [4-hydroxyphenyl-pyrazole(N-CH$_3$)-furan] | f |
| 243 | [(3-phenoxyphenyl)-pyrazole(N-CH$_3$)-(3-fluorophenyl)] | f |

TABLE 7-continued

| Compound | Structure | IC$_{50}$ |
|---|---|---|
| 244 | [(3-phenoxyphenyl)-pyrazole(N-CH$_3$)-furan] | f | a = 0–50 μM
b = 51–100 μM
c = 101–500 μM
d = 501–1000 μM
e = 1001–1500 μM
f = >1500 μM

TABLE 8

| Compound | Structure | % Inhib. at 100 μM |
|---|---|---|
| 245 | [bromo-phenyl, diethyl phosphonate, NH–C(O)–(4-bromophenyl)] | 67 |
| 246 | [bromo-phenyl, diethyl phosphonate, NH–C(O)–(4-butoxyphenyl)] | 57 |
| 247 | [bromo-phenyl, diethyl phosphonate, NH–C(O)–(4-heptylphenyl)] | 53 |

TABLE 8-continued

| Compound | Structure | % Inhib. at 100 μM |
|---|---|---|
| 248 | 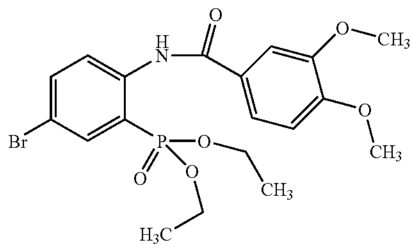 | 48 |

TABLE 9

| Compound | Structure | % Inhib. at 100 μM |
|---|---|---|
| 249 | 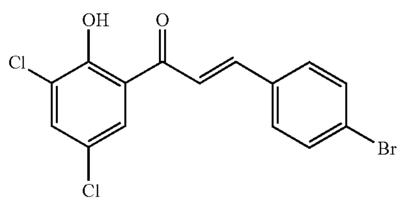 | 50 |

TABLE 10

| Compound | Structure | IC$_{50}$ |
|---|---|---|
| 250 | 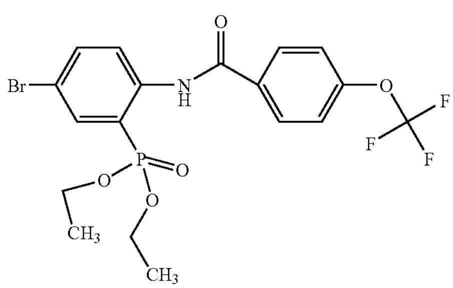 | a |
| 251 | 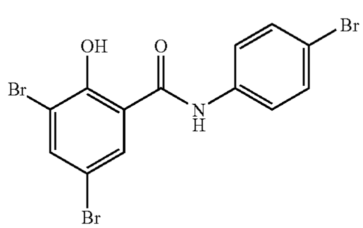 | b |
| 252 | 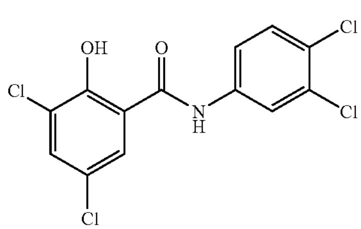 | b |

TABLE 10-continued

| Compound | Structure | IC$_{50}$ |
|---|---|---|
| 253 | 3,5-dibromo-2-hydroxy-N-(4-bromophenyl)benzamide | c |
| 254 | N-[3-chloro-4-(1-bromonaphthalen-2-yloxy)phenyl]-3,5-dibromo-2-hydroxybenzamide | c |
| 255 | 3,5-dibromo-2-hydroxy-N-(4-chlorophenyl)benzamide | c |
| 256 | 3,5-dibromo-2-hydroxy-N-[2,5-bis(trifluoromethyl)phenyl]benzamide | c |
| 257 | N-(4-methoxyphenyl)-8-hydroxy-9H-benzo[a]carbazole-7-carboxamide | c |

TABLE 10-continued

| Compound | Structure | IC$_{50}$ |
|---|---|---|
| 258 | 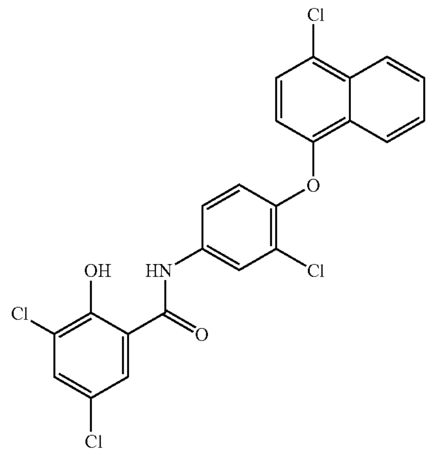 | c |
| 259 | 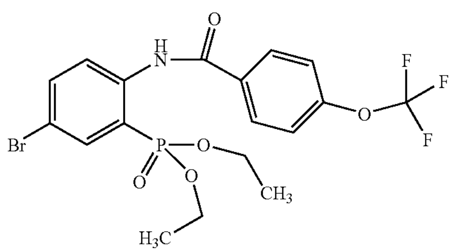 | c |
| 260 | 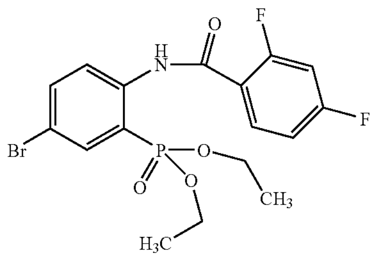 | c |
| 261 | 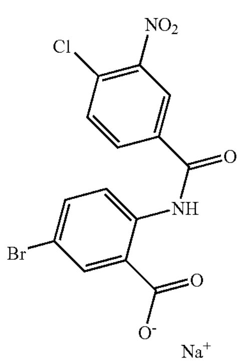 | c |

TABLE 10-continued

| Compound | Structure | IC$_{50}$ |
|---|---|---|
| 262 | 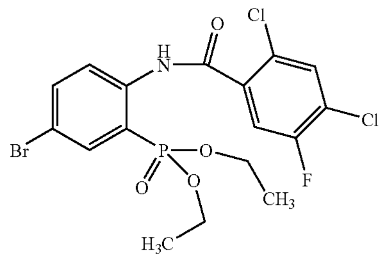 | c |
| 263 | 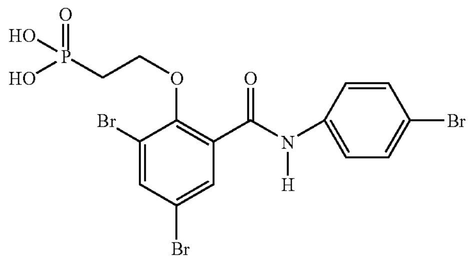 | c |
| 264 | 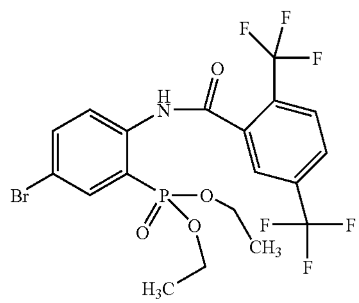 | c |
| 265 | 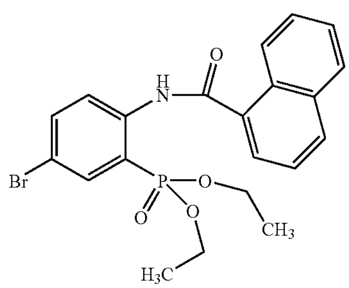 | d |
| 266 | 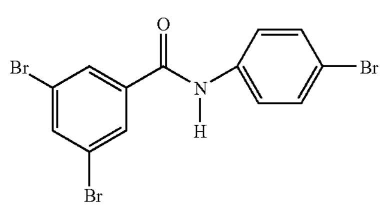 | d |
| 267 | 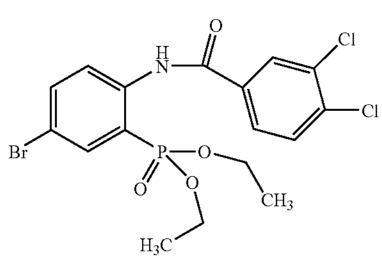 | d |

TABLE 10-continued

| Compound | Structure | IC$_{50}$ |
|---|---|---|
| 268 | 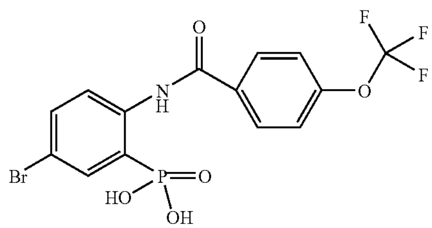 | f |
| 269 | 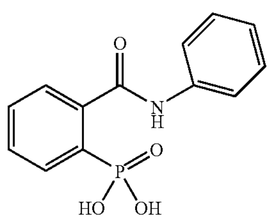 | f |
| 270 | 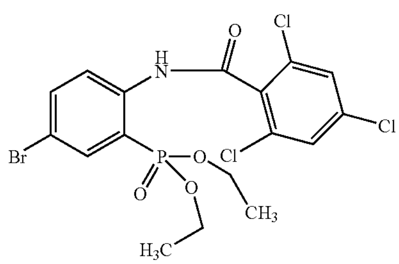 | f |
| 271 | 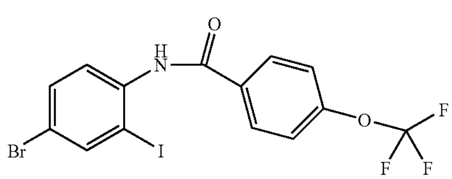 | f |
| 272 | | f | a = 0–50 μM
b = 51–100 μM
c = 101–500 μM
d = 501–1000 μM
e = 1001–1500 μM
f = >1500 μM

TABLE 11

| Compound | Structure | IC$_{50}$ |
|---|---|---|
| 273 | (3-(4-hydroxyphenyl)-1-(2,4,6-trihydroxyphenyl)propan-1-one) | d |
| 274 | (1-(3-hydroxyphenyl)-3-(furan-2-yl)prop-2-en-1-one) | d |
| 275 | (1-(3-methoxyphenyl)-3-(furan-2-yl)prop-2-en-1-one) | d |
| 276 | (1-(3-phenoxyphenyl)-3-(furan-2-yl)prop-2-en-1-one) | d |

TABLE 11-continued

| Compound | Structure | IC$_{50}$ |
|---|---|---|
| 277 | (1-(3-hydroxyphenyl)-3-(3-fluorophenyl)prop-2-en-1-one) | d |
| 278 | (1-(3-methoxyphenyl)-3-(3-fluorophenyl)prop-2-en-1-one) | f |
| 279 | (1-(3-phenoxyphenyl)-3-(3-fluorophenyl)prop-2-en-1-one) | f | a = 0–50 μM
b = 51–100 μM
c = 101–500 μM
d = 501–1000 μM
e = 1001–1500 μM
f = >1500 μM

TABLE 12

| Compound | Structure | % Inhib. at 100 μM |
|---|---|---|
| 280 | 2,4-dichlorobenzyl 3,5-bis(trifluoromethyl)phenyl sulfone | 57 |
| 281 | 2,6-dichlorobenzyl 4-methylphenyl sulfone | 53 |
| 282 | 2-fluoro-3-methylbenzyl 4-chlorophenyl sulfone | 53 |
| 283 | 2,6-dichlorobenzyl 3,5-bis(trifluoromethyl)phenyl sulfone | 51 |
| 284 | 3,4-dichlorobenzyl 2,4-dichloro-5-methylphenyl sulfone | 51 |
| 285 | 2-chloro-4-nitrobenzyl 2,4-difluorophenyl sulfone | 44 |
| 286 | 2-chloro-6-fluorobenzyl 4-chlorophenyl sulfone | 39 |

TABLE 12-continued

| Compound | Structure | % Inhib. at 100 μM |
|---|---|---|
| 287 | (benzyl phenyl sulfone) | 34 |
| 288 | (4-chlorophenyl 2-fluoro-4-bromobenzyl sulfone) | 31 |
| 289 | (4-nitrobenzyl phenyl sulfone) | 27 |
| 290 | (phenyl 4-fluorobenzyl sulfone) | 24 |
| 291 | (4-chlorophenyl 4-trifluoromethylbenzyl sulfone) | 0 |

TABLE 13

| Compound | Structure | IC$_{50}$ |
|---|---|---|
| 292 | (disodium stilbene bis-sulfonate bis-azo-4-hydroxyphenyl) | a |
| 293 | (disodium stilbene bis-sulfonate bis-(4-biphenylsulfonamide)) | b |

TABLE 13-continued

| Compound | Structure | IC$_{50}$ |
|---|---|---|
| 294 | 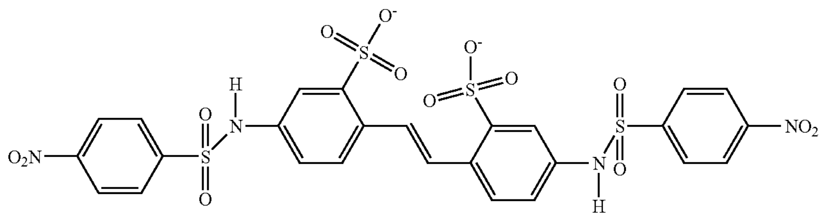 | c |
| 295 | 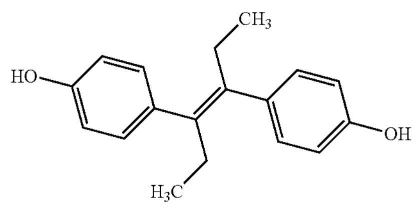 | c |
| 296 | 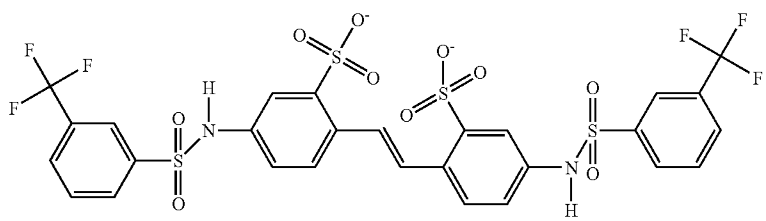 | c |
| 297 | 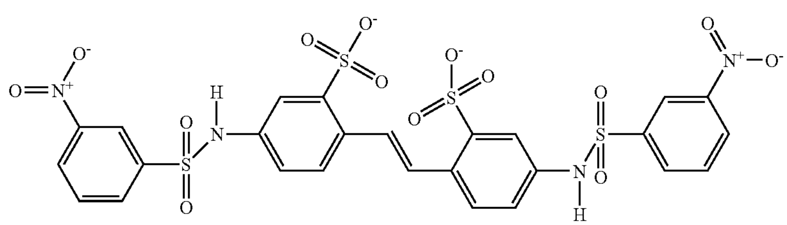 | c |
| 298 | 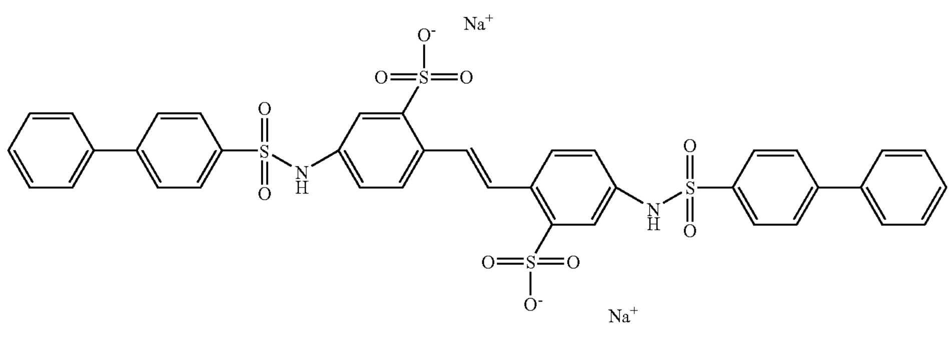 | d |
| 299 | 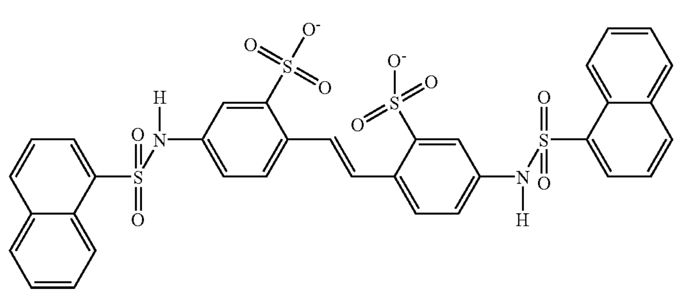 | d |

US 7,119,120 B2
123 124
TABLE 13-continued
| Compound | Structure | IC$_{50}$ |
|---|---|---|
| 300 | 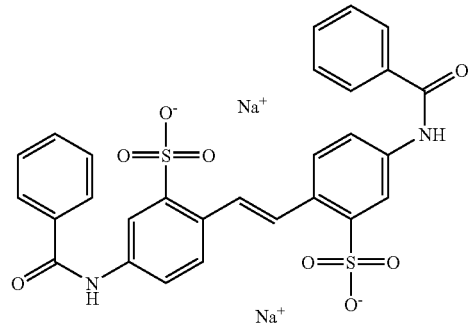 | d |
| 301 | 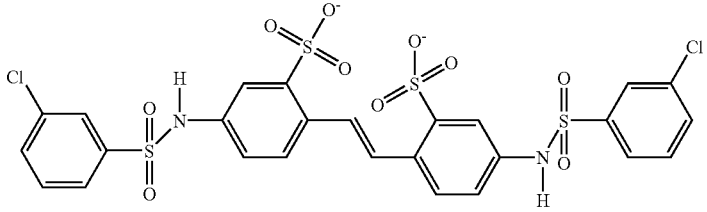 | d |
| 302 | 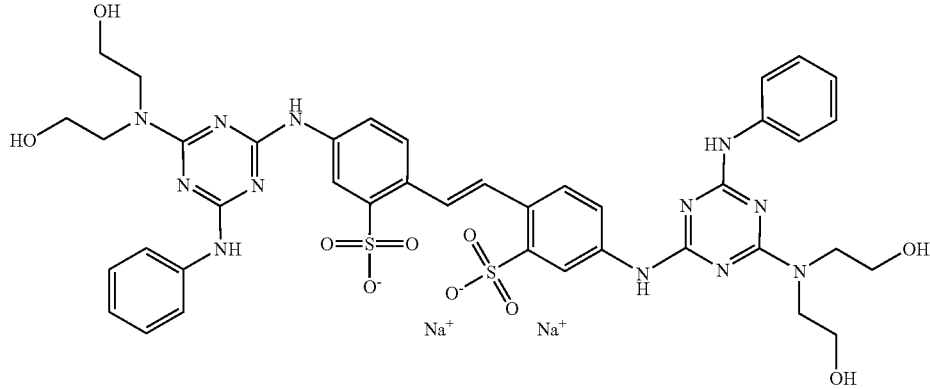 | d |
| 303 | 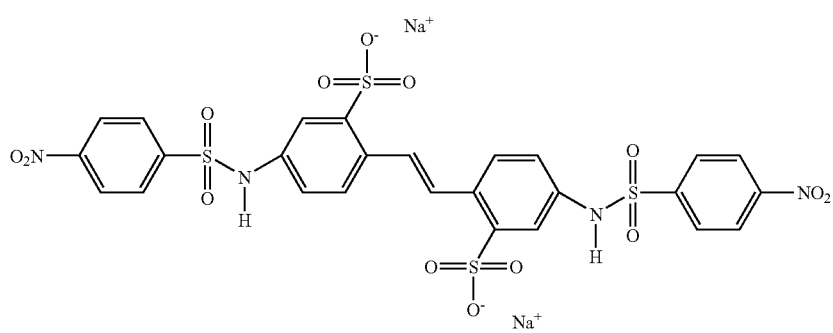 | d |

TABLE 13-continued

| Compound | Structure | IC$_{50}$ |
|---|---|---|
| 304 | 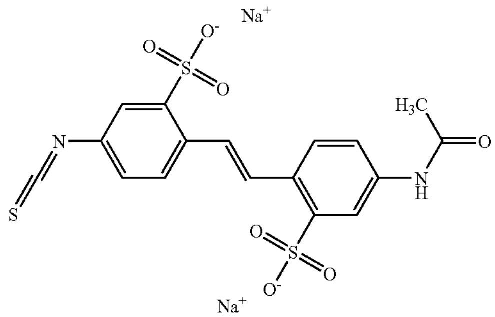 | d |
| 305 | 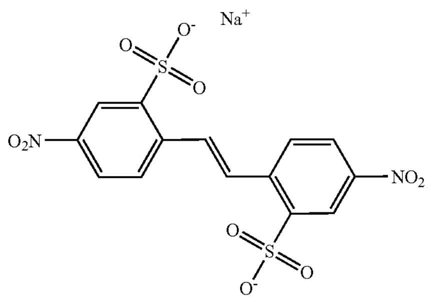 | e |
| 306 | 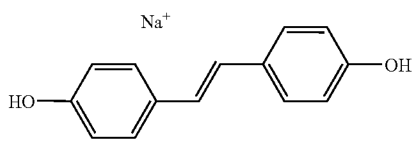 | f |
| 307 | 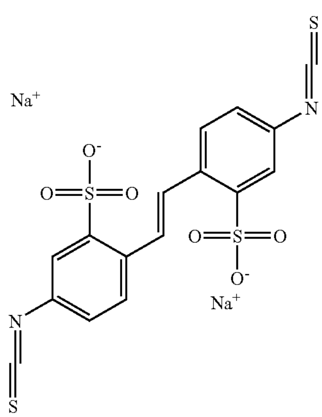 | f |
| 308 | 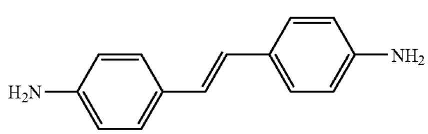 | f |

TABLE 13-continued

| Compound | Structure | IC$_{50}$ |
|---|---|---|
| 309 | 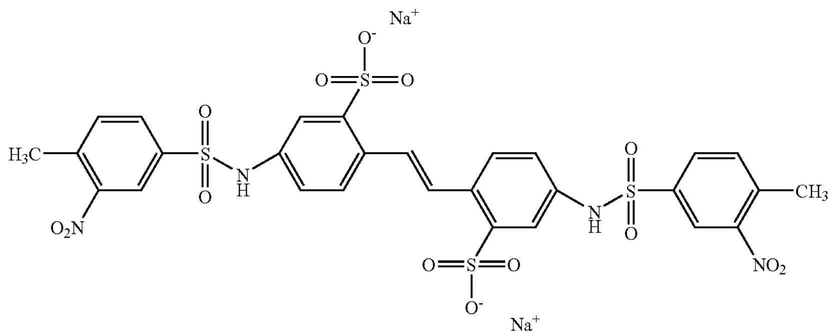 | f |
| 310 | 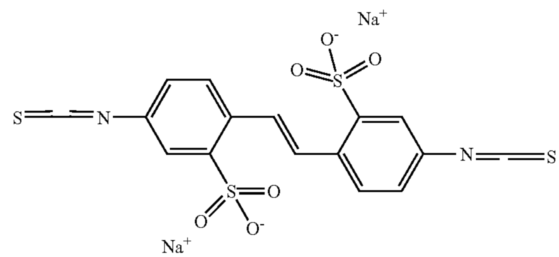 | f |
| 311 | | f | a = 0–50 μM
b = 51–100 μM
c = 101–500 μM
d = 501–1000 μM
e = 1001–1500 μM
f = >1500 μM

EXAMPLE 67

Methyl 5-bromo-2-(4-trifluoromethoxy-benzene-sulfonylamino)benzoate

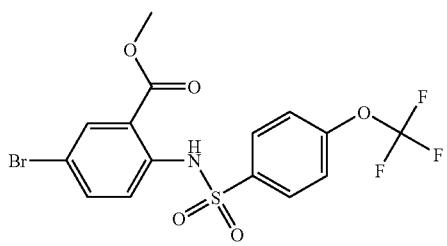

Methyl 2-amino-5-bromo benzoate (2.78 g, 0.012 mol) was dissolved in pyridine (3 mL). The mixture was cooled in an ice bath below 5° C. and 4-trifluoromethoxy-benzene sulfonyl chloride (3.5 g, 0.013 mol, 1.1 equivalents) was added slowly to the mixture. The mixture was warmed to room temperature, and stirred for 1 hour. The solvent was removed and the resulting solid was suspended in HCl (1M, 40 mL) for 30 minutes. The solid was collected by filtration and then suspended in hexane (40 mL) and stirred for 30 minutes. The mixture was filtered and the solid was washed with hexane (2×20 mL). The solid was dried in a vacuum oven at 40° C. Recovery=4.63 g (85% yield).

EXAMPLE 68

5-Bromo-2-(4-trifluoromethoxy-benzenesulfonylamino)-benzoic acid

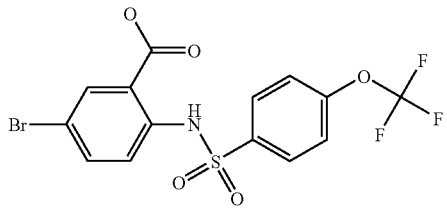

Methyl 5-bromo-2-(4-trifluoromethoxy-benzenesulfonylamino)benzoate (0.854 g, 0.019 mmol) was dissolved in a mixture of tetrahydrofuran (20 mL)/water (10 mL). A solution of sodium hydroxide (50%, 5 mL) was added and the mixture was heated to reflux for 2–3 hours. The tetrahydrofuran was removed by rotary evaporation and the mixture was acidified with aqueous HCl (2 M). The mixture was extracted with ethyl acetate (20 mL). The organic solvent was removed to dryness. The residue was dried azeotropically by dissolution in ethyl acetate followed by evaporation (3×15 mL). This provided an oil, which was triturated in hexane (20 mL) until a solid formed. The solid was collected by filtration and dried in a vacuum oven at 40° C. Recovery=0.691 g (83% yield). M/Z of (M–H)⁻=432, $^1$H NMR (DMSO) δ=7.42–7.48 (1H), 7.55–7.6 (2H), 7.74–7.8 (1H), 7.92–8.0 (3H), 11,2 (br, 1H).

EXAMPLE 69

5-Bromo-2-(4-trifluoromethoxy-benzenesulfonylamino)-benzoyl chloride

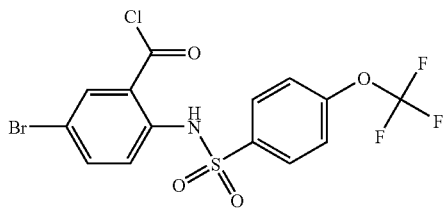

5-Bromo-2-(4-trifluoromethoxy-benzenesulfonylamino)-benzoic acid (3.27 g, 7.4 mmol) was suspended in thionyl chloride (30 mL). The mixture was heated to reflux for 4 hours. The solvent was removed to dryness. The residue was dissolved in anhydrous ethyl acetate and solvent removed (2×20 mL). The solid was dried at 40° C. in vacuum oven overnight.

EXAMPLE 70

5-Bromo-N-(2-methoxy-benzyl)-2-(4-trifluoromethoxy-benzenesulfonylamino)-benzamide

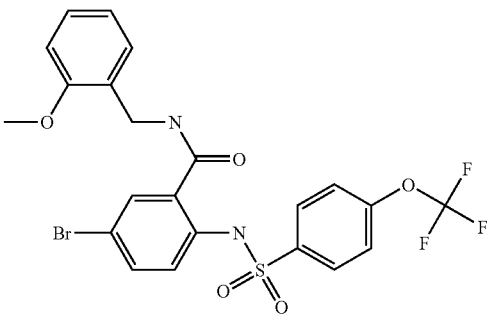

5-Bromo-2-(4-trifluoromethoxy-benzenesulfonylamino)-benzoyl chloride (5.124 g, 11.6 mmol) was dissolved in tetrahydrofuran (100 mL) and the mixture was cooled in an ice bath below 5° C. 2-Methoxy-benzyl amine (1.8 mL, 13.8 mmol, 1.2 equivalents) and triethyl amine (1.9 mL, 13.6 mmol, 1.2 equivalents) were added to the mixture keeping the temperature below 10° C. The mixture was warmed to room temperature and the solvent was removed to dryness. The residue was partitioned between aqueous HCl (1M, 50 mL) and ethyl acetate (100 mL). The organic solvent was collected and concentrated to dryness. The resulting solid was dissolved in ethyl acetate and the solvent removed (2×25 mL). The resulting mixture was purified by column chromatography on silica with an eluent of 20% ethyl acetate in hexane. The solid was suspended in a mixture of 5% ethyl acetate in hexane (90 mL). The mixture was centrifuged and the solid dried at 40° C. overnight in vacuum oven. Recovery=4.85 g (75% yield). M/Z of [M–H]⁻=557, $^1$H NMR (CDCl₃) δ=3.85 (s, 3H), 4.5 (sd, 2H), 6.5–6.6 (1H), 6.9–7.05 (4H), 7.3–7.4 (2H), 7.45 (1H), 7.5 (1H), 7.6 (1H), 7.8 (2H), 10.8 (br, 1H).

EXAMPLE 71

5-Bromo-N-(4-fluoro-benzyl)-2-(4-trifluoromethoxy-benzenesulfonylamino)-benzamide

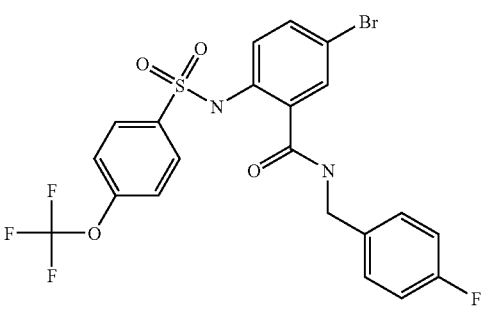

This compound was prepared using the procedure described in Example 70, using 4-fluoro benzyl amine instead of 2-methoxy benzyl amine: M/Z of [M–H]⁻=545. $^1$H NMR (DMSO) δ=4.4 (sd, 2H), 7.15–7.23 (2H), 7.3–7.4

(2H), 7.4–7.5 (3H), 7.65–7.7 (1H), 7.8–7.9 (2H), 7.9–8.0 (1H), 9.4 (br, 1H), 11.5 (br, 1H).

EXAMPLE 72

5-Bromo-2-(4-chloro-benzenesulfonylamino)-N-(2-trifluoromethoxy-benzyl)-benzamide

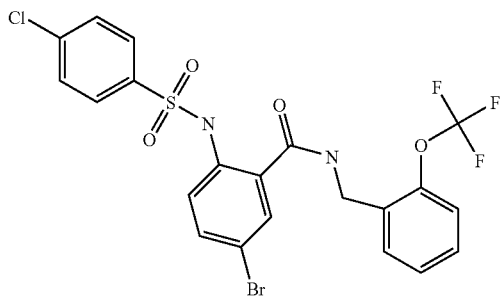

This compound was prepared using the procedure described in Example 70, using 5-bromo-2-(4-chloro-benzenesulfonylamino)-benzoyl chloride instead of 5-bromo-2-(4-trifluoromethoxy-benzenesulfonylamino)-benzoyl chloride, and 2-trifluoromethoxybenzyl amine instead of 2-methoxy benzyl amine. M/Z of [M–H]⁻=563.8. $^1$H NMR (DMSO) δ=4.4 (sd, 2H), 7.3–7.4 (5H), 7.5 (2H), 7.65–7.7 (3H), 7.9–8.0 (1H), 9.4 (br, 1H), 11.5 (br, 1H).

EXAMPLE 73

2-Chloro-N-(2-hydroxy-4-trifluoromethoxy-benzyl)-acetamide

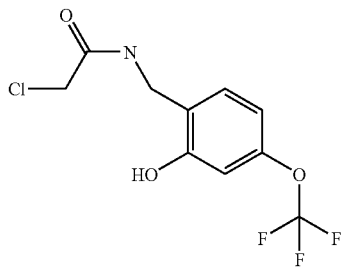

3-(Trifluoromethoxy)phenol (4.827 g, 27 mmol) was dissolved in glacial acetic acid (20 mL). The mixture was cooled in an ice bath between 14–17° C. and concentrated sulfuric acid (2 mL) was slowly added keeping the temperature below 20° C. The mixture was cooled below 10° C. and N-hydroxymethyl-2-chloroacetamide (3.52 g, 28.5 mmol) was added. The mixture was warmed slowly to room temperature and stirred overnight. The mixture was then poured slowly into ice (200 mL) and the pH was adjusted to ~4–5 with KOH pellets, keeping the temperature below 5° C. The reaction mixture was warmed to room temperature and extracted twice with ethyl acetate (150 mL). The organic layer was collected and washed with NaHCO₃ (sat., 30 mL). The organic layer was dried over MgSO₄, filtered and the solvent removed to dryness. The mixture was purified by column chromatography (SiO₂, 700 mL) using an eluent of hexane/ethyl acetate (10/2). Recovery: 2.42 g (33.8% yield).

$^1$H NMR (DMSO) δ=10.23 (1H, s), 8.56 (1H, st), 7.16–7.14 (1H, sd), 6.71–6.70 (2H, br), 4.18–4.17 (2H, d), 4.08 (2H, s).

EXAMPLE 74

2-Aminomethyl-5-trifluoromethoxy-phenol

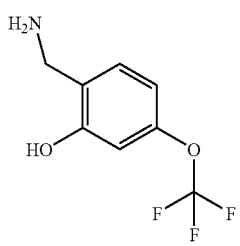

2-Chloro-N-(2-hydroxy-4-trifluoromethoxy-benzyl)-acetamide (9.9 g, 37.4 mmol) was dissolved in a mixture of ethanol (100 mL)/aqueous HCl (12 M, 50 mL). The mixture was refluxed for ~6 hours. The solvent was removed by rotary evaporation and the residue was azeotropically dried by dissolution in ethyl acetate followed by rotary evaporation (6×150 mL). The resulting solid was suspended in ethyl acetate (100 mL), collected by filtration and dried at 65° C. in a vacuum oven overnight. Recovery: 8.68 g (95.3% yield). M/Z (–HCl) of [M–H]⁻=208. $^1$H NMR (D₂O) δ=7.26–7.22 (1H, sd), 6.76–6.75 (2H, br), 4.07 (2H, s).

EXAMPLE 75

5-Bromo-N-(2-hydroxy-4-trifluoromethoxy-benzyl)-2-(4-trifluoromethoxy-benzenesulfonylamino)-benzamide

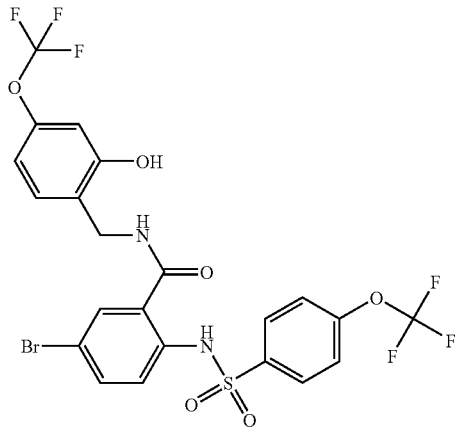

This compound was prepared using the procedure described in Example 70, using 2-hydroxy-4-trifluoromethoxy benzyl amine hydrochloride instead of 2-methoxy benzyl amine: M/Z of [M–H]⁻=629. $^1$H NMR (DMSO) δ=11.51 (1H, s), 10.28 (1H, s), 9.23 (1H, st), 7.95 (1H, sd), 7.81–7.79 (2H, m), 7.67–7.64 (1H, m), 7.45–7.40 (3H, m), 7.16–7.14 (1H, d), 6.73–6.71 (2H, br), 4.29 (2H, sd).

EXAMPLE 76

2-Chloro-N-(5-fluoro-2-methoxy-benzyl)-acetamide

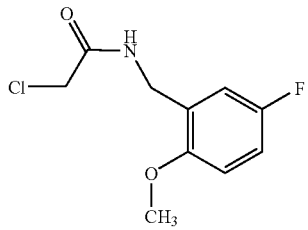

This compound was prepared using the procedure described in Example 73, using 4-fluoro anisole instead of 3-trifluoromethoxy phenol. ¹H NMR (DMSO) δ=8.65 (1H, Br), 7.09–7.03 (1H, dt), 7.02–6.95 (2H, m), 4.26–4.22 (2H, d), 4.1 92H, s).

EXAMPLE 77

5-Fluoro-2-methoxy-benzylamine hydrochloride

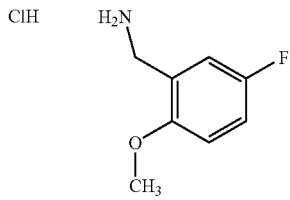

This compound was prepared using the procedure described in Example 74, using 2-chloro-N-(2-methoxy-5-trifluoromethoxy-benzyl)-acetamide, instead of 2-chloro-N-(2-hydroxy-4-trifluoromethoxy-benzyl)-acetamide. ¹H NMR (CD₃OD) δ=7.15–7.11 (2H, m), 7.06–7.03 (1H, m), 4.06 (2H, s), 3.88 (3H, s).

EXAMPLE 78

5-Bromo-N-(5-fluoro-2-methoxy-benzyl)-2-(4-trifluoromethoxy-benzenesulfonylamino)-benzamide

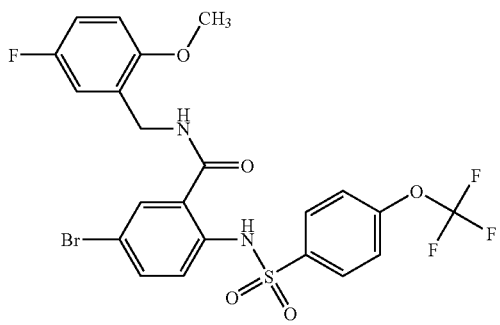

This compound was prepared using the procedure described in Example 70, using 2-methoxy-5-fluoro benzyl amine hydrochloride instead of 2-methoxy benzyl amine: ¹H NMR (DMSO) δ=11.45 (1H, s), 9.22 (1H, st), 7.97–7.96 (1H, sd), 7.82–7.80 (2H, sd), 7.67–7.65 (1H, sdd), 7.47–7.39 (3H, m), 7.09–7.02 (1h, dt), 6.98–6.92 (2H, m), 4.31 (2H, d), 3.31 (3H, s).

EXAMPLE 79

2-Amino-5-bromo-N-(2-methoxy-benzyl)-benzamide

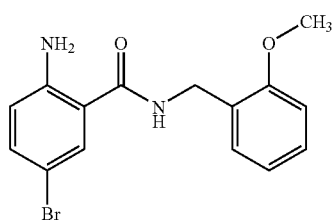

Under a nitrogen atmosphere, 2-methoxy benzylamine (10 g, 73 mmol) was suspended in anhydrous toluene (30 ml). This suspension was cooled down in ice bath and (2 M) trimethyl aluminum solution in hexanes (36 ml, 72 mmol) was added slowly. The reaction mixture was stirred at room temperature for 1 hour after the completion of the addition. The resulting solution was then cooled in an ice bath and methyl-2-amino-5-bromobenzoate was added in small portions. The reaction was allowed to stir at room temperature overnight. This solution was poured into a pre-cooled solution 2N HCl (300 ml). The solid obtained was collected by filtration and triturated in methanol (50 ml). The solid was collected and dried under high vacuum oven at 65° C. overnight. Pure product was recovered (16 g). ¹H NMR (DMSO) δ=3.8 (s, 3H), 4.35 (sd, 2H), 6.5 (2H), 6.6 (1H), 6.85 (1H), 6.9 (1H), 7.1–7.25 (3H), 7.7 (1H), 8.7 (br, 1H).

EXAMPLE 80

5-Bromo-N-(2-methoxy-benzyl)-2-(4-trifluoromethyl-2-nitro-benzenesulfonylamino)-benzamide

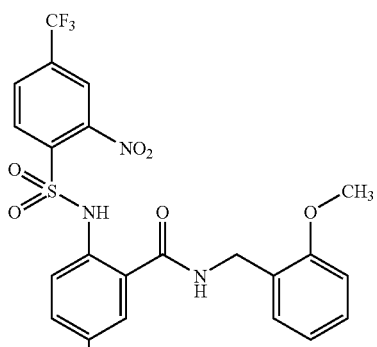

2-Amino-5-bromo-N-(2-methoxy-benzyl)-benzamide (9 g, 28 mmol) was suspended in anhydrous dichloromethane (300 ml) and cooled in ice bath. Pyridine (20 ml) was added with stirring, followed by addition of 2-nitro-4-trifluoromethyl-benzene sulfonyl chloride (15 g, 52 mmol). The reaction mixture was allowed to stir at room temperature for 2 days. The mixture was filtered to remove a solid precipitate and the filtrate was evaporated to dryness. Aqueous HCl (2N, 300 ml) was added, and the resulting solution was extracted with dichloromethane (500 ml). The organic layer was concentrated and the resulting residue was dissolved in ethyl acetate. Addition of hexanes to this solution produced a solid precipitate. This solid was dissolved in ethyl acetate and passed through a short column of silica using an eluent of dichloromethane and ethyl acetate to provide the desired product (7.5 g, 46% yield). M/Z of [M–H]⁻=587.1 ¹H NMR (DMSO) δ=3.8 (s, 3H), 4.35 (sd, 2H), 6.85 (1H), 6.95 (1H), 7.1 (1H), 7.2 (1H), 7.4 (1H), 7.65 (1H), 8 (1H), 8.15 (1H), 8.25 (1H), 8.55 (1H).

EXAMPLE 81

N-(4-Bromo-phenyl)-3-trifluoromethyl-benzamide

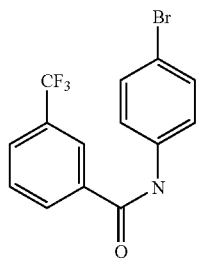

Under a nitrogen atmosphere, 4-bromoaniline (15.75 g, 91.6 mmol) was dissolved in anhydrous dichloromethane (220 ml) in a 500-ml flask. Triethylamine (14.1 ml, 100 mmol) was added to the solution. The mixture was cooled in an ice bath and 3-(trifluoromethyl)benzoyl chloride (21 g, 100 mmol) was added slowly through a syringe. The reaction mixture was allowed to warm to room temperature with stirring overnight. Deionized water was added to the mixture and the solution was transferred to a separatory funnel. The organic layer was separated and washed one more time with deionized water. The water was discarded, and the organic layer contained a suspension that was collected and heated to 40° C. to afford dissolution. After cooling to room temperature, a solid formed. The solid was collected by filtration and was triturated in dichloromethane (100 ml). The solid was then filtered and dried under high vacuum oven at 65° C. Pure product was obtained (28 g, 90% yield). M/Z of [M–H]⁻=343. ¹H NMR (DMSO) δ=7.6 (2H), 7.8 (3H), 7.95 (1H), 8.3(1H), 10.6 (1H).

EXAMPLE 82

1,3 Bis(3-Trifluoromethylphenyl)urea

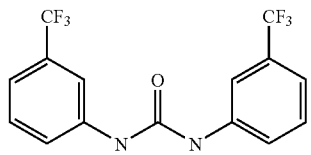

3-(Trifluoromethyl)aniline 10 g (62.1 mmol) was added to 500 ml of anhydrous dichloromethane in a 500 ml round bottomed flask. This stirred solution was cooled to 0° C. using an ice water bath. 3-(Trifluoromethyl)phenyl isocyanate 15 g (80.1 mmol) was added drop-wise over a period of 10 minutes. The reaction mixture was allowed to warm to room temperature and stirred at ambient temperatures for 18 hours. During this time a heavy precipitate was formed. This solid was collected by filtration on a Buchner funnel, and was re-suspended in 250 ml of dichloromethane. After approximately 30 minutes of stirring, the solid was again filtered on a Buchner funnel and then placed under vacuum at 40° C. to dry for a period of 24 hours to give 20 g of a white solid (92.5% yield). ¹H NMR (400 MHz DMSO) δ 9.20 (s 2H) 8.04 (s 2H) 7.61 (m 2H) 7.54 (t 2H) 7.34 (m 2H). MS: M+1 found 349.

EXAMPLE 83

1-Cyclohexyl-3-(3,5-Bis trifluoromethyl-phenyl)-urea

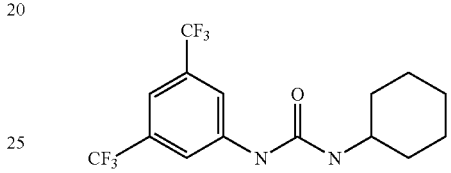

Cyclohexylamine 4.98 g (49.3 mmol) was added to 120 ml of anhydrous dichloromethane in a 500 ml round bottomed flask. This stirred solution was cooled to 0° C. using an ice water bath. 3,5-Bis(trifluoromethyl)phenyl isocyanate 12.33 g (48.3 mmol) was added drop wise over a period of 15 minutes. The reaction mixture was allowed to warm to room temperature and stirred at ambient temperatures for 18 hours. During this time a heavy precipitate was formed. This solid was collected by filtration on a Buchner funnel, and was re-suspended in 250 ml of dichloromethane. After approximately 30 minutes of stirring, the solid was again filtered on a Buchner funnel and then placed under vacuum at 40° C. to dry for a period of 24 hours to give 15.4 g of a white solid (90% yield). ¹H NMR (400 MHz DMSO) δ 9.10 (s 1H) 8.10 (s 2H) 7.53 (s 1H) 6.43 (d 1H) 3.49 (m 1H) 1.81 (t 2H) 1.68 (m 2H) 1.54 (m 1H) 1.25 (m 5H). MS: m/z 355 (M+1).

EXAMPLE 84

5-tert-Butyl-2-methyl-2H-pyrazole-3-carboxylic acid(4-trifluoromethyl-phenyl)-amide

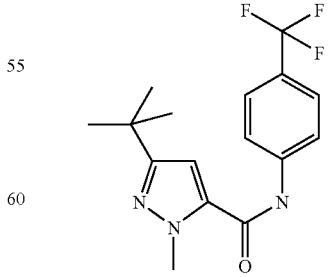

4-Trifluoromethylaniline (19.39 g, 120.3 mmol) and triethylamine (13.4 g ,132 mmol) was added to 400 ml of anhydrous dichloromethane in a 1-liter round bottomed flask. This stirred solution was cooled to 4° C. using an ice water bath. 3-tert-Butyl-1-methyl-1H-pyrazole-5-carbonyl chloride 26.57 g (132 mmol) was added drop wise to this cooled solution. The reaction mixture was allowed to warm to room temperature and then was stirred at ambient temperature for 18 hours. The reaction mixture was then placed in an extraction funnel and then extracted first with 400 ml of 1N HCl and subsequently with 300 ml of water. The extraction with water was repeated. The organic layer was then stirred in a 2 liter Erlenmeyer flask and 500 ml of hexane added. The mixture was stirred for 2 hours and provided a precipitate which was collected by filtration on a Buchner funnel. The white solid was then dried in vacuum oven at 40° C. for 24 hours to give 20.63 g of pure product (52% yield). $^1$H NMR (400 MHz CDCl$_3$) δ: 7.85 (s 1H) 7.74 (s 2H) 7.62 (d 1H) 6.53 (s 1H) 4.16 (s 3H) 1.33 (s 9H). MS: m/z 324.2 (M−1)

EXAMPLE 85

1-(2,5-Dichloro-phenyl)-3-(3-trifluoromethyl-phenyl)-urea

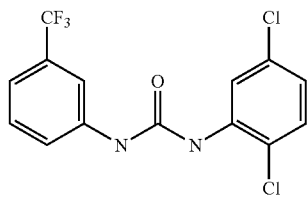

α-Trifluoro m-tolyl isocyanate (15 g, 80.16 mmol) was dissolved in 120 mL of methylene chloride under a nitrogen atmosphere. A solution of 2,5-dichloroaniline (13 g, 80.16 mmol,) dissolved in 30 mL of methylene chloride was added drop-wise. The reaction mixture was left to stir for 12 hours. During this time, an off-white precipitate formed. This solid was collected by filtration and dried under vacuum to give 11.2 g of pure product (40% yield). $^1$H NMR (400 MHz CDCl$_3$) δ: 7.04 (dd, 1H), 7.29 (s, 1H), 7.41–7.49 (m, 3H), 7.98 (s, 1H), 8.25 (d, 1H), 8.47 (s, 1H), 9.81 (s, 1H). MS: m/z 371 (M+Na$^+$).

EXAMPLE 86

1-(4-Fluoro-3-nitro-phenyl)-3-(3-trifluoromethyl-phenyl)-urea

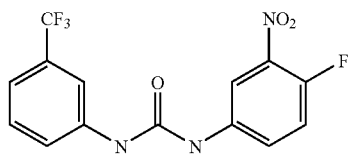

4-Fluoro-3-nitrophenyl isocyanate (15 g, 82.40 mmol) was dissolved in 200 mL of methylene chloride under a nitrogen atmosphere. A solution of 3-trifluoromethyl aniline (13.27 g, 82.40 mmol) dissolved in 50 mL of methylene chloride was added drop-wise. The reaction was left to stir for 12 hours. During this time, a yellow precipitate formed. This solid was collected by filtration and dried under vacuum to give 27.9 g of pure product (98% yield). $^1$H NMR (400 MHz CDCl$_3$) δ: 7.25 (dd, 1H), 7.39–7.46 (m, 2H), 7.55 (d, 1H), 7.63–7.67 (m, 1H), 7.94 (s, 1H), 8.36 (dd, 1H), 9.14 (s, 1H), 9.21 (s, 1H). MS: m/z 366 (M+Na$^+$).

EXAMPLE 87

N,N'-Bis-(4-bromo-3-trifluoromethyl-phenyl)-guanidine Hydrochloride

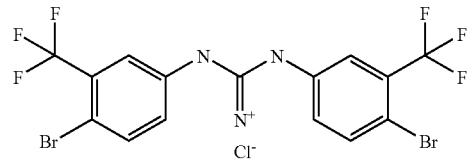

To a 30 mL vial containing a magnetic stirring bar, 3-trifluoromethyl-4-bromoaniline (4.00 g, 16.7 mmol) was added along with anhydrous ethanol (15 mL) and a 5 M solution cyanogen bromide in acetonitrile (1.67 mL, 8.33 mmol). The vial was sealed and the resulting solution was stirred at 90–95° C. for 2 days. The volatiles were removed by rotary evaporation and the residue was dissolved in 50 mL CHCl$_3$. This was then washed with 3 N aqueous NaOH (50 mL) followed by water (50 mL). Drying with Na$_2$SO$_4$ and column chromatographic separation (silica, 3:1 EtOAc/Hexanes) afforded 1.2 g of the guanidine product as a light yellow solid. Electrospray MS (m/z: MH$^+$503, 505, 507). This was dissolved in a small amount of MeOH and titrated with 3 N aqueous HCl. The resulting solution was concentrated slightly by rotary evaporation to cause the precipitation of N,N'-Bis-(4-bromo-3-trifluoromethyl-phenyl)-guanidine hydrochloride as a white solid. This was filtered, washed with rinsed with water and then dried in vacuo. $^1$H-NMR (DMSO-d$_6$) δ 7.52 (d J 8.8 Hz, 2H, NHCHCH), 7.81 (s, 2H, NHCHCF$_3$), 7.89 (d, J 8.8 Hz, 2H, CBrCH), 8.40 (s, 2H, NH, NH), 10.60 (s, 2H, NH$_2$). Electrospray MS (m/z: MH$^+$504, 506, 508), CHN calc. 33.27, 1.86, 7.76, found 33.32, 1.64, 7.58.

EXAMPLE 88

N,N'-Bis-(3,5-bis-trifluoromethyl-phenyl)-guanidine Hydrochloride

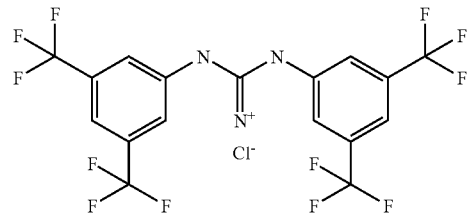

N,N'-Bis-(3,5-bis-trifluoromethyl-phenyl)-guanidine Hydrochloride was prepared as described in example 87 using 3,5-bis-trifluoromethylaniline in place of 3-trifluoromethyl-4-bromoaniline. $^1$H-NMR (DMSO-d$_6$) δ 7.85 (s, 2H, CF$_3$CHCF$_3$), 7.90 (s, 4H, NHCCH), 8.68 (s, 2H, NH, NH), 11.12 (s, 2H, NH$_2$). Electrospray MS (m/z: MH$^+$484).

EXAMPLE 89

N,N'-Bis-(4-chloro-3-trifluoromethyl-phenyl)-guanidine Hydrochloride

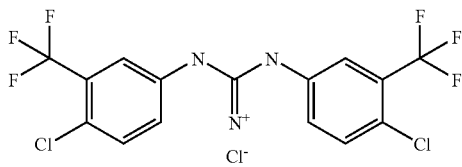

N,N'-Bis-(4-chloro-3-trifluoromethyl-phenyl)-guanidine Hydrochloride was prepared as described in example 87 using 3-trifluoromethyl-4-chloroaniline in place of 3-trifluoromethyl-4-bromoaniline. $^1$H-NMR (DMSO-$d_6$) δ 7.65 (d, 8.4 Hz, 2H, NHCC$\underline{H}$CH), 7.78 (d, 8.4 Hz, 2H, NHCCHC$\underline{H}$), 7.87 (s, 2H, C$\underline{H}$CCF$_3$), 8.44 (s, 2H, N$\underline{H}$, N$\underline{H}$), 10.67 (s, 2H, N$\underline{H}_2$) Electrospray MS (m/z: MH$^+$416, 418) CHN calc. 39.91, 2.23, 9.28, found 39.77, 2.03, 9.27.

EXAMPLE 90

N,N'-Bis-(3,4-bis-trifluoromethyl-phenyl)-guanidine Hydrochloride

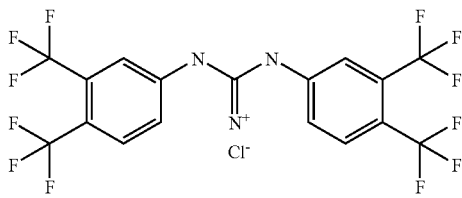

N,N'-Bis-(3,4-bis-trifluoromethyl-phenyl)-guanidine Hydrochloride was prepared as described in example 1 using 3,4-bis-trifluoromethylaniline in place of 3-trifluoromethyl-4-bromoaniline. $^1$H-NMR (DMSO-$d_6$) δ 7.79 (d, J 8.4 Hz, 2H, CNC$\underline{H}$CCH), 7.99 (s, 2H, CNC$\underline{H}$CCF$_3$), 8.04 (d J 8.8 Hz, 2H, CF3CC$\underline{H}$CH), 8.82 (s, 2H, N$\underline{H}$, N$\underline{H}$), 11.13 (s, 2H, N$\underline{H}_2$) Electrospray MS (m/z: MH$^+$484).

EXAMPLE 91

In Vitro and ex Vivo Testing of Phosphate Transport Inhibitors

The phosphate transport inhibitors indicated in Table 14 were tested in both an in vitro and an ex vivo assay to determine their activity. The in vitro assay is identical to the assay described in Example 66, with the exception that the glucose transport inhibiting activity of the compounds was also measured. Results are reported as the IC$_{50}$ value for the various types of inhibition. A preferred compound will have high phosphate transport inhibiting activity, but little or no glucose transport inhibiting activity.

For the ex vivo assay, $^{33}$P uptake into isolated rabbit intestinal rings was measured using a modification of the method described by Crane and Mandelstam [Robert K. Crane and Paul Mandelstam "The active transport of sugars by various preparations of hamster intestine" *Biochim. Biophys. Acta* 45: 460–476, 1960; the contents of which are incorporated herein by reference]. Male New Zealand rabbits 2–3 kg in weight were aeuthinized by an i.v. injection of Fatal Plus®. A midline laparotomy was performed and the duodenum from the pyloric junction to the ligament of Trietz isolated and excised. Segments of bowel were everted, cut into 2–4 mm ring-like pieces and placed into a modified Hepes-Buffered Ringer's solution in which Na$^+$ had been iso-osmotically replaced with N-methyl-D-glucamine. To measure phosphate uptake, six rings were incubated in a 50 ml conical tube containing a 10 ml volume of Ringer's solution, with or without Na$^+$, bubbled with 100% O$_2$ and maintained at 37° C. 0.5 uCi/ml $^{33}$P was then incubated with the rings for a 15-minute period, the tissue harvested, rinsed, blotted dry and weighed. Tissues were then solublized by digesting them in a 5 ml volume of Solvable® tissue solubilizer overnight at 50° C. and $^{33}$P levels determined by scintillation counting. Sodium-dependent uptake of $^{33}$P was calculated by determining the difference in uptake between rings incubated in the presence and absence of Na$^+$ in the Hepes-Buffered Ringer's solution. Results are reported as the percentage inhibition of phosphate and glucose uptake, respectively.

TABLE 14

Biological Testing of Phosphate Transport Inhibitors

| Compound | Phosphate Transport IC$_{50}$ | Glucose Transport IC$_{50}$ | % Phosphate Transport Inhibition | % Glucose Transport Inhibition |
|---|---|---|---|---|
| Example 81 | 10 μM | >100 μM | 22% | 13% |
| Example 84 | 11 μM | 99 μM | 41% | 21% |
| Example 88 | 26 μM | 63 μM | 60% | 0% |
| Example 87 | 35 μM | 94 μM | 71% | 3% |
| Example 89 | 16 μM | 88 μM | 44% | 0% |
| Example 90 | 17 μM | >100 μM | 93% | 0% |
| Example 85 | 10 μM | >100 μM | 58% | 0% |
| Example 86 | 2.8 μM | 34 μM | 30% | 4% |
| Example 82 | 11 μM | 54 μM | 25% | 26% |
| Example 83 | 7.7 μM | 82 μM | 76% | 0% |
| Example 72 | 7 μM | >100 μM | 24% | 6% |
| Example 71 | 13 μM | >100 μM | 53% | 26% |
| Example 75 | 5.2 μM | 80 μM | 56% | 0% |
| Example 78 | 7.8 μM | 100 μM | 45% | 4% |
| Example 70 | 6.3 μM | >100 μM | 48% | 8% |
| Example 80 | 31 μM | >100 μM | 43% | 39% |

Table 14 shows that the compounds tested are effective and potent inhibitors of phosphate transport. Table 14 additionally shows that the compounds tested are selective, in that glucose transport into cells and tissues is generally minimally affected by the compounds.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of inhibiting phosphate transport in a subject in need of phosphate transport inhibition, said method comprising the step of administering an effective amount of a compound represented by the following structural formula:

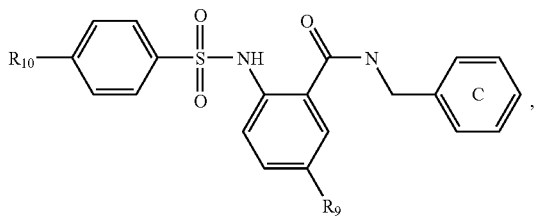

wherein $R_9$ is a halogen, $R_{10}$ is a halogen, a substituted alkyl group, an alkoxy group, a substituted alkoxy group or —$NO_2$; and Ring C is substituted with one or more substituents independently selected from a halogen, a hydroxy group, an alkoxy group, a lower alkyl group, a cycloalkyl group, a heterocycloalkyl group, an aryl group, a heteroaryl group, an aryloxy group, an aralkyl group, a heteroaralkyl group, —$C(O)NR_4R_5$, —$C(O)OR_6$, —$P(O)(OR_6)_2$, —$NR_4R_5$, —$NCR_7(PO_3)_2$, —$NO_2$, $SO_3$, —$S(O)_2R_6$, —$C(O)R_7$, —$SR_4$, —$CR_7=NR_4$, —$NR_4SO_2R_5$, —N=N—$R_4$, —CN, —$N_3$ or —N=C=S, $R_4$, $R_5$ and $R_6$ are independently a hydrogen, lower alkyl group, heteroalkyl group, cycloalkyl group, aralkyl group, or heteroaralkyl group; and $R_7$ is a hydrogen, lower alkyl group, heteroalkyl group, cycloalkyl group, an aryl group, a heteroaryl group, —$OR_6$ or —$NR_4R_5$.

2. The method of claim 1, wherein said subject is in need of treatment for hyperphosphatemia.

3. The method of claim 1, wherein the subject is in need of treatment for chronic renal failure.

4. The method of claim 1, wherein the subject is in need of treatment for disorders of phosphate metabolism or impaired phosphate transport function.

5. The method of claim 1, wherein the subject is in need of treatment for hyperparathyroidism, uremic bone disease, soft tissue calcification or osteoporosis.

6. The method of claim 1, wherein the method further comprises co-administering one or more phosphate sequestrants to the subject.

7. The method of claim 6, wherein the method further comprises co-administering sevelamer to the subject.

8. The method of claim 1, wherein $R_{10}$ is a halogen or a substituted alkoxy group.

9. The method of claim 8, wherein $R_{10}$ is a trifluoromethoxy group.

10. A method of inhibiting phosphate transport in a subject in need of phosphate transport inhibition, said method comprising the step of administering an effective amount of a compound represented by the following structural formula:

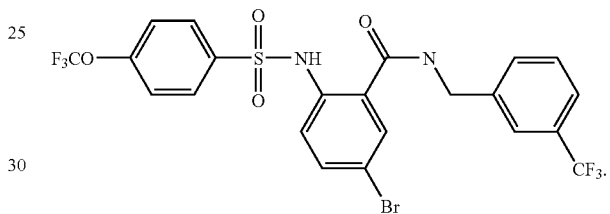

* * * * *

UNITED STATES PATENT AND TRADEMARK OFFICE
CERTIFICATE OF CORRECTION

PATENT NO. : 7,119,120 B2
APPLICATION NO. : 10/327627
DATED : October 10, 2006
INVENTOR(S) : Thomas H. Jozefiak et al.

It is certified that error appears in the above-identified patent and that said Letters Patent is hereby corrected as shown below:

Column 141, lines 1-12, delete

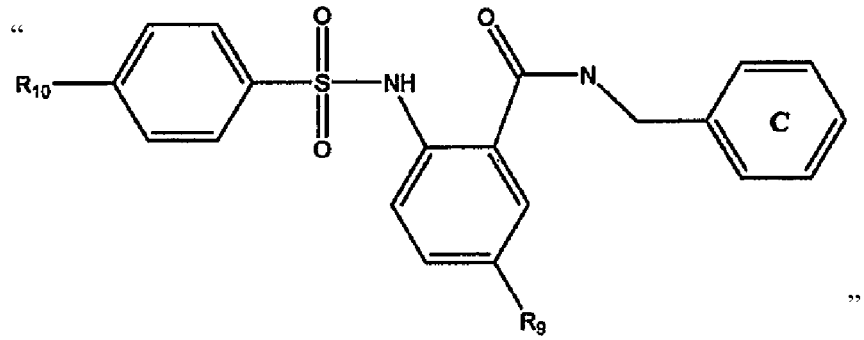

and insert

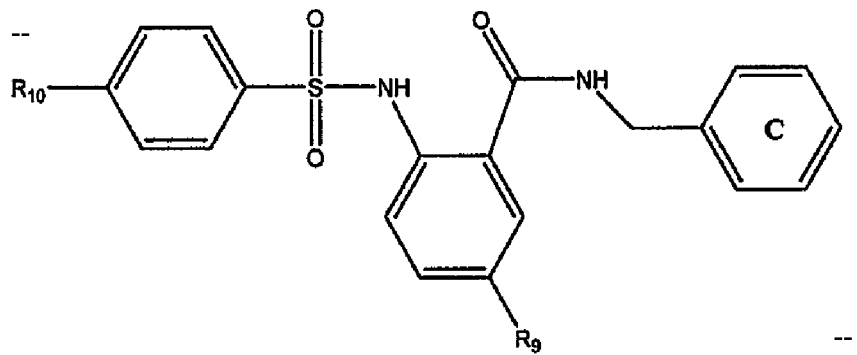

Column 141, line 23, delete "$SO_3$" and insert -- $-SO_3$ --

UNITED STATES PATENT AND TRADEMARK OFFICE
CERTIFICATE OF CORRECTION

PATENT NO. : 7,119,120 B2
APPLICATION NO. : 10/327627
DATED : October 10, 2006
INVENTOR(S) : Thomas H. Jozefiak et al.

It is certified that error appears in the above-identified patent and that said Letters Patent is hereby corrected as shown below:

Column 142, lines 14-34, delete

"

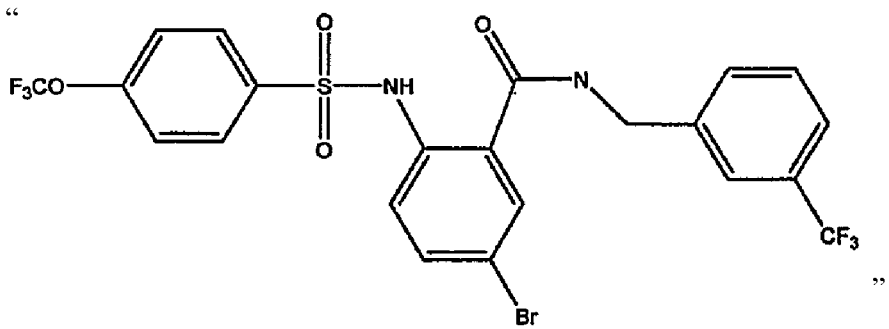

and insert

--

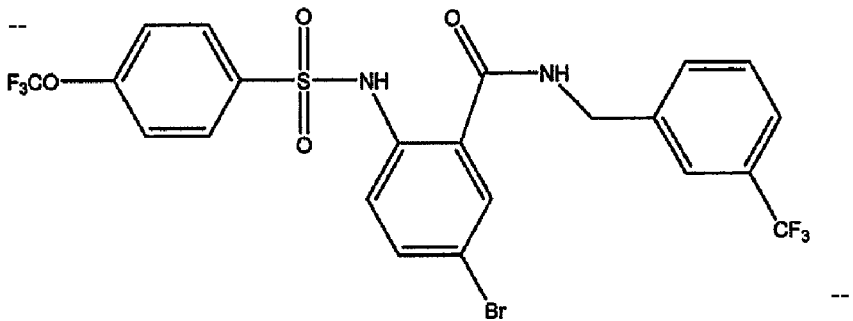

--

Signed and Sealed this

Third Day of April, 2007

JON W. DUDAS
*Director of the United States Patent and Trademark Office*